(12) United States Patent
Powell, Jr. et al.

(10) Patent No.: US 11,484,552 B2
(45) Date of Patent: *Nov. 1, 2022

(54) USE OF TRANS-SIGNALING APPROACH IN CHIMERIC ANTIGEN RECEPTORS

(71) Applicant: THE TRUSTEES OF THE UNIVERSITY OF PENNSYLVANIA, Philadelphia, PA (US)

(72) Inventors: Daniel J. Powell, Jr., Bala Cynwyd, PA (US); Carl H. June, Merion Station, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/148,067

(22) Filed: Oct. 1, 2018

(65) Prior Publication Data

US 2019/0125797 A1    May 2, 2019

Related U.S. Application Data

(63) Continuation of application No. 14/044,569, filed on Oct. 2, 2013, now Pat. No. 10,117,896.

(60) Provisional application No. 61/710,518, filed on Oct. 5, 2012.

(51) Int. Cl.
| | | |
|---|---|---|
| A61K 35/17 | (2015.01) | |
| C07K 16/30 | (2006.01) | |
| A61K 39/395 | (2006.01) | |
| C07K 16/28 | (2006.01) | |
| C12N 5/0783 | (2010.01) | |

(52) U.S. Cl.
CPC .......... *A61K 35/17* (2013.01); *A61K 39/3955* (2013.01); *C07K 16/28* (2013.01); *C07K 16/30* (2013.01); *C12N 5/0636* (2013.01); *C07K 2317/622* (2013.01); *C07K 2319/00* (2013.01); *C07K 2319/33* (2013.01); *C12N 2510/00* (2013.01)

(58) Field of Classification Search
None
See application file for complete search history.

(56) References Cited

U.S. PATENT DOCUMENTS

| | | | |
|---|---|---|---|
| 5,199,942 A | 4/1993 | Gillis et al. | |
| 5,359,046 A | 10/1994 | Capon et al. | |
| 5,686,281 A | 11/1997 | Roberts | |
| 5,858,358 A | 1/1999 | June et al. | |
| 5,883,223 A | 3/1999 | Gray | |
| 5,993,434 A | 11/1999 | Dev et al. | |
| 6,181,964 B1 | 1/2001 | Hofmann et al. | |
| 6,233,482 B1 | 5/2001 | Hofmann et al. | |
| 6,241,701 B1 | 6/2001 | Hofmann et al. | |
| 6,352,694 B1 | 3/2002 | June et al. | |
| 6,516,223 B2 | 2/2003 | Hofmann et al. | |
| 6,534,055 B1 | 3/2003 | June et al. | |
| 6,567,694 B2 | 5/2003 | Hayakawa et al. | |
| 6,678,556 B1 | 1/2004 | Nolan et al. | |
| 6,692,964 B1 | 2/2004 | June et al. | |
| 6,797,514 B2 | 9/2004 | Berenson et al. | |
| 6,867,041 B2 | 3/2005 | Berenson et al. | |
| 6,887,466 B2 | 5/2005 | June et al. | |
| 6,905,680 B2 | 6/2005 | June et al. | |
| 6,905,681 B1 | 6/2005 | June et al. | |
| 6,905,874 B2 | 6/2005 | Berenson et al. | |
| 7,049,136 B2 | 5/2006 | Seed et al. | |
| 7,067,318 B2 | 6/2006 | June et al. | |
| 7,144,575 B2 | 12/2006 | June et al. | |
| 7,171,264 B1 | 1/2007 | Hofmann et al. | |
| 7,172,869 B2 | 2/2007 | June et al. | |
| 7,173,116 B2 | 2/2007 | Fewell et al. | |
| 7,175,843 B2 | 2/2007 | June et al. | |
| 7,232,566 B2 | 6/2007 | June et al. | |
| 7,723,111 B2 | 5/2010 | Hwu et al. | |
| 8,389,282 B2 | 3/2013 | Sadelain et al. | |
| 9,272,002 B2 | 3/2016 | Powell et al. | |
| 10,654,928 B2 * | 5/2020 | Kloss ............. | A61K 39/001188 |
| 2004/0014645 A1 | 1/2004 | Draghia-Akli et al. | |
| 2004/0059285 A1 | 3/2004 | Mathiesen et al. | |
| 2004/0092907 A1 | 5/2004 | Mathiesen et al. | |
| 2004/0101519 A1 | 5/2004 | June et al. | |
| 2005/0052630 A1 | 3/2005 | Smith et al. | |
| 2005/0070841 A1 | 3/2005 | Mathiesen et al. | |
| 2006/0034810 A1 | 2/2006 | Riley et al. | |

(Continued)

FOREIGN PATENT DOCUMENTS

| | | |
|---|---|---|
| EP | 0871495 B1 | 6/2005 |
| EP | 1379670 B1 | 8/2008 |

(Continued)

OTHER PUBLICATIONS

Riley et al., 2009, Immunol. Rev. vol. 229: 114-125.*
Hanada et al., 2013, Nat. Biotech. vol. 31: 33-34.*
Abcam, KD value: a quantitative measurment of antibody affinity, pp. 1-9.*
Rabia et al., 2018, Biochem. Eng. J. vol 137: 365-374.*
Hall et al., 1992, J. Immunol. vol. 149: 1605-1612.*
Lindner et al., 2020, Sci. Adv. vol. 6: 1-8.*
Alvarez-Vallina, et al., Antigen-specific targeting of CD28-mediated T cell co-stimulation using chimeric single-chain antibody variable fragment-CD28 receptors., Eur J Immunol. Oct. 1996;26(10):2304-9. (Abstract).

(Continued)

*Primary Examiner* — Amy E Juedes
(74) *Attorney, Agent, or Firm* — Saul Ewing Arnstein & Lehr LLP; Kathryn Doyle

(57) ABSTRACT

The present invention provides compositions and methods for inducing a CAR mediated trans-signal in a T cell. The trans-signaling CAR T cells comprise a first CAR having a first signaling module and a second CAR having a distinct second signaling module. The present invention also provides cells comprising a plurality of types of CARs, wherein the plurality of types of CARs participate in trans-signaling to induce T cell activation.

5 Claims, 18 Drawing Sheets

Specification includes a Sequence Listing.

(56) References Cited

U.S. PATENT DOCUMENTS

| | | | |
|---|---|---|---|
| 2006/0121005 | A1 | 6/2006 | Berenson et al. |
| 2007/0128708 | A1 | 6/2007 | Gamelin et al. |
| 2013/0121960 | A1 | 5/2013 | Sadelain et al. |

FOREIGN PATENT DOCUMENTS

| | | | |
|---|---|---|---|
| EP | 2141997 B1 | 10/2012 | |
| EP | 2537416 B1 | 11/2014 | |
| WO | 2011041093 A1 | 4/2011 | |
| WO | 2012079000 A1 | 6/2012 | |
| WO | 2012099973 A2 | 7/2012 | |
| WO | 2013185552 A1 | 12/2013 | |
| WO | 2014055668 A1 | 4/2014 | |
| WO | 2014145252 A2 | 9/2014 | |

OTHER PUBLICATIONS

Berge, et al., Selective Expansion of a Peripheral Blood CD8+ Memory T Cell Subset Expressing Both Granzyme B and L-Selectin During Primary Viral Infection in Renal Allograft Recipients., Transplantation Proceedings, 30, 3975-3977 (1998).
Berry, et al., Adoptive immunotherapy for cancer: the next generation of geneengineered immune cells., Tissue Antigens. Oct. 2009;74(4):277-89 (Abstract).
Bierer, et al., Cyclosporin A and FK506: molecular mechanisms of immunosuppression and probes for transplantation biology, Current Opinion in Immunology 1993, 5:763-773.
Bird, et al., Single-chain Antigen-Binding Proteins, 1988, Science 242:423-426.
Brentjens, et al., Treatment of Chronic Lymphocytic Leukemia With Genetically Targeted Autologous T Cells: Case Report of an Unforeseen Adverse Event in a Phase I Clinical Trial, Molecular Therapy 18:666-668.
Carpenito, et al., Control of large, established tumor xenografts with genetically retargeted human T cells containing CD28 and CD137 domains, Proc. Natl. Acad Sci 106:3360-3365.
Chang, et al., Isolation and characterization of a monoclonal antibody, K1, reactive with ovarian cancers and normal mesothelium., Int J Cancer Feb. 1, 1992;50(3):373-81. (Abstract).
Cohen, et al., Suicide gene-mediated modulation of graft-versus-host disease., Leuk Lymphoma. Aug. 1999;34(5-6):473-80. (Abstract).
Cougot, et al., 'Cap-tabolism'., Trends Biochem Sci. Aug. 2004;29(8):436-44. (Abstract).
Dainty, et al., Overexpression of folate binding protein and mesothelin are associated with uterine serous carcinoma., 2007, Gyn Onc 105:563-570.
Distasi, et al., Inducible Apoptosis as a Safety Switch for Adoptive Cell Therapy, N Engl J Med 2011;365:1673-83.
Duong, et al., Enhancing the specificity of T-cell cultures for adoptive immunotherapy of cancer., Immunotherapy. 3(1):33-48 (2011).
Elango, et al., Optimized transfection of mRNA transcribed from a d(A/T)100 tailcontaining vector., Biochem Biophys Res Commun. May 13, 2005;330(3):958-66. (Abstract).
Emtage, et al., Second-Generation Anti Carcinoembryonic Antigen Designer T Cells Resist Activation-Induced Cell Death, Proliferate on Tumor Contact, Secrete Cytokines, and Exhibit Superior AntitumorActivity In vivo: A Preclinical Evaluation, Clin Cancer Res 2008;14:8112-8122.
Ertl, et al., Considerations for the Clinical Application of Chimeric Antigen Receptor T Cells: Observations from a Recombinant DNA Advisory Committee Symposium Held Jun. 15, 2010, Cancer Res 2011;71:3175-3181.
Feugier, et al., Comparison of initial characteristics and long-term outcome of patients with lymphocyte-predominant Hodgkin lymphoma and classical Hodgkin lymphoma at clinical stages IA and IIA prospectively treated by brief anthracycline-based chemotherapies plus extende, Blood, 2004 104: 2675-2681.

Garland, et al., The use of Teflon cell culture bags to expand functionally active CD8+ cytotoxic T lymphocytes., Journal of Immunological Methods 227 (1999) 53-63.
Gilham, et al., Primary Polyclonal Human T Lymphocytes Targeted to Carcino-embryonic Antigens and Neural Cell Adhesion Molecule Tumor Antigens by CD3zeta-Based Chimeric Immune Receptors., 2002, J Immunother 25(2):139-151.
Gross, et al., Expression of immunoglobulin-T-cell receptor chimeric molecules as functional receptors with antibody-type specificity., Proc. Natl. Acad. Sci. USA vol. 86, pp. 10024-10028, Dec. 1989.
Haanen, et al., Selective Expansion of Cross-reacitve CD8+ Memory T Cells by Viral Variants., 1999, J Exp Med 190(9):1319-1328.
Hassan, et al., Localization of Mesothelin in Epithelial Ovarian Cancer, Appl. Immunohistochem Mol Morphol. 13:243-247 (2005) Abstract.
Henderson, et al., Comparison of the effects of FK-506, cyclosporin A and rapamycin on IL-2 production., Immunology (1991) 73:316-321.
Heslop, et al., Saver CARS, Mol. Ther. 18:661-662 (2010).
Holm, et al., The High-Affinity Folate Binding Protein in Normal and Malignant Mammary Gland Tissue, Chemistry and Biology of Pteridines and Folates Advances in Exp. Med. Biol. 338:757-60 (1993).
Hombach, et al., T-Cell Activation by Recombinant Receptors: CD28 Costimulation Is Required for Interleukin 2 Secretion and Receptor-mediated T-Cell Proliferation but Does Not Affect Receptor-mediated Target Cell Lysis1, Cancer Research 61, 1976-1982, Mar. 1, 2001.
Huston, et al., Protein engineering of antibody binding sites: Recovery of specific activity in an anti-digoxin single-chain Fv analogue produced in *Escherichia coli*, 1988, Proc Natl Acad Sci USA 85:5879-5883.
Inman, et al., Costimulation, Coinhibition and Cancer, Current Cancer Drug Targets, 2007, 7, 15-30.
Jena, et al., Redirecting T-cell specificity by introducing a tumor-specific chimeric antigen receptor., Blood, (2010) 116:1035-1044.
Johnson, et al., Gene Transfer of Tumor-Reactive TCR Confers Both High Avidity and Tumor Reactivity to Nonreactive Peripheral Blood Mononuclear Cells and Tumor-Infiltrating Lymphocytes, J Immunol. Nov. 1, 2006; 177(9): 6548-6559.
Junghans, et al., CSotmrrnaetnetargy y Escalation: An emerging paradigm for safe clinical development of T cell gene therapies, Journal of Translational Medicine 2010, 8:55 (8 pages).
Kalli, et al., Folate receptor alpha as a tumor target in epithelial ovarian cancer, Gynecol Oncol. Mar. 2008 ; 108(3):619-626.
Kalos, et al., T Cells with Chimeric Antigen Receptors Have Potent Antitumor Effects and Can Establish Memory in Patients with Advanced Leukemia, Sci Transl Med. Aug. 10, 2011; 3(95): 95ra73 (21 pages).
Kershaw, et al., A Phase I Study on Adoptive Immunotherapy Using Gene-Modified T Cells for Ovarian Cancer., Clin Cancer Res 2006; 12:6106-6115.
Kowolik, et al., CD28 Costimulation Provided through a CD19-Specific Chimeric Antigen Receptor Enhances In vivo Persistence and Antitumor Efficacy of Adoptively Transferred T Cells, Cancer Res 2006; 66: (22). Nov. 15, 2006.
Krause, et al., Antigen-dependent CD28 Signaling Selectively Enhances Survival and Proliferation in Genetically Modified Activated Human Primary T Lymphocytes., J Exp Med (1998) 188(4):619-626.
Kuo, et al., Deformability considerations in filtration of biological cells., Lab Chip. Apr. 7, 2010;10(7):837-42 (Abstract).
Lamers, et al., Treatment of Metastatic Renal Cell Carcinoma With Autologous T-Lymphocytes Genetically Retargeted Against Carbonic Anhydrase IX: First Clinical Experience., 2006, Journal of Clinical Oncology 24(13)e20-e22.
Lanitis, et al., Redirected Antitumor Activity of Primary Human Lymphocytes Transduced With a Fully Human Anti-mesothelin Chimeric Receptor, Molecular Therapy vol. 20 No. 3, 633-643 Mar. 2012.
Levine, et al., Effects of CD28 Costimulation on Long-Term Proliferation of CD4+ T Cells in the Absence of Exogenous Feeder Cells, 1997, The Journal of Immunology 159:5921-5930.

(56) References Cited

OTHER PUBLICATIONS

Liu, et al., Calcineurin Is a Common Target of Cyclophilin-Cyclosporin A and FKBP-FK506 Complexes., Cell, vol. 66, 907-615, Aug. 23, 1991.

Mantovani, et al., Folate binding protein distribution in normal tissues and biological fluids from ovarian carcinoma patients as detected by the monoclonal antibodies MOv18 and MOv19., Eur J Cancer 1994;30A(3):363-9—Abstract.

Milone, et al., Chimeric Receptors Containing CD137 Signal Transduction Domains Mediate Enhanced Survival of T Cells and Increased Antileukemic Efficacy In Vitro, 2009, Molecular Therapy 17(8):1453-1464.

Moon, et al., Expression of a Functional CCR2 Receptor Enhances Tumor Localization and Tumor Eradication by Retargeted Human T cells Expressing a Mesothelin-Specific Chimeric Antibody Receptor, Clin Cancer Res; 17(14);4719-30. (2011).

Moran, et al., Methods for generation of monoclonal antibodies to the very small drug hapten, 5-benzimidazolecarboxylic acid., J Immunol Methods. Dec. 20, 2002;271(1-2):65-75. (Abstract).

Morgan, et al., Adoptive cell therapy: genetic modification to redirect effector cell specificity., 2010, Cancer J. 16(4):336-41 (Abstract).

Nacheva, et al., Preventing nondesired RNA-primed RNA extension catalyzed by T7 RNA polymerase, Eur. J. Biochem. 270, 1458-1465 (2003).

Nishikawa, et al., Nonviral vectors in the new millennium: delivery barriers in gene transfer., Hum Gene Ther. May 20, 2001;12(8):861-70. (Abstract).

Ordonez, et al., Value of Mesothelin Immunostaining in the Diagnosis of Mesothelioma, Mod Pathol 2003;16(3):192-197.

Parker, et al., Folate receptor expression in carcinomas and normal tissues determined by a quantitative radioligand binding assay., 2005 Anal Biochem 338(2):284-293 (Abstract).

PCT/US2013/063083, et al., International Search Report and Written Opinion, dated Jan. 17, 2014.

Pham, et al., Chasing cancer with chimeric antigen receptor therapy., 2012, Immunotherapy 4(4):365-367 (Abstract).

Plaimauer, et al., Cloning, expression, and functional characterization of the vonWillebrand factor-cleaving protease (ADAMTS13), 2002, Blood 100(10):3626-3632.

Porter, et al., Chimeric Antigen Receptor-Modified T Cells in Chronic Lymphoid Leukemia., N Engl J Med 2011;365:725-33.

Pule, et al., Virus-specific T cells engineered to coexpress tumor-specific receptors: persistence and antitumor activity in individuals with neuroblastoma., 2008, Nat Med 14(11):1264-1270.

Rosenberg, et al., Use of Tumor-Infiltrating Lymphocytes and Interleukin-2 in the Immunotherapy of Patients with Metastic Melanoma., 1988, New Eng J of Med 319:1676.

Sadelain, et al., The promise and potential pitfalls of chimeric antigen receptors., 2009, Current Opinion in Immunology 21:215-223.

Savoldo, et al., CD28 costimulation improves expansion and persistence of chimeric antigen receptor-modified T cells in lymphoma patients., 2011, J Clin Invest 121(5):1822-1826.

Schenborn, et al., A novel transcription property of SP6 and T7 RNA polymerases: dependence on template structure, 1985, Nucleic Acids Research 13(17):6223-6236.

Song, et al., CD27 costimulation augments the survival and antitumor activity of redirected human T cells in vivo, 2012, Blood, 119: 696-706.

Song, et al., In vivo persistence, tumor localization and anti-tumor activity of CAR engineered T cells is enhanced by costimulatory signaling through CD137 (4-1BB), Cancer Res. Jul. 1, 2011; 71(13): 4617-4627.

Stepinski, et al., Synthesis and properties of mRNAs containing the novel "anti-reverse" cap analogs 7-methyl(39-O-methyl)GpppG and 7-methyl(39-deoxy)GpppG., RNA (2001), 7:1486-1495.

Straathof, et al., An inducible caspase 9 safety switch for T-cell therapy, 2005, Blood, 105: 4247-4254.

Tey, et al., Inducible caspase 9 suicide gene to improve the safety of allodepleted T cells after haploidentical stem cell transplantation, Biol Blood Marrow Transplant. Aug. 2007; 13(8): 913-924.

Thomis, et al., AFas-based suicide switch in human T cells for the treatment of graft-versus-host disease, Blood. 2001;97:1249-1257.

Till, et al., Adoptive immunotherapy for indolent non-Hodgkin lymphoma and mantle cell lymphoma using genetically modified autologous CD20-specific T cells., 2008, Blood, 112:2261-2271.

Foffoli, et al., Overexpression of Folate Binding Protein in Ovarian Cancers, Int. J. Cancer (Pred. Oncol.): 74, 193-198 (1997).

Urbanska, et al., A Universal Strategy for Adoptive Immunotherapy of Cancer through Use of a Novel T-cell Antigen Receptor., 2012, Cancer Res 72:1844 1852.

Wang, et al., IgE actions on CD4+ T cells, mast cells, and macrophages participate in the pathogenesis of experimental abdominal aortic aneurysms., 2014, EMBO Mol Med 6:752-969.

Weitman, et al., Distribution of the Folate Receptor GP38 in Normal and Malignant Cell Lines and Tissues1., Cancer Research 52, 3396-3401, Jun. 15, 1992.

Wilkie, et al., Dual Targeting of ErbB2 and MUC1 in Breast Cancer Using Chimeric Antigen Receptors Engineered to Provide Complementary Signaling., J Clin Immunol. Oct. 2012;32(5):1059-70.

Zhao, et al., Multiple injections of electroporated autologous T cells expressing a chimeric antigen receptor mediate regression of human disseminated tumor, Cancer Res. Nov. 15, 2010; 70(22): 9053-9061.

Zhong, et al., Chimeric Antigen Receptors Combining 4-1BB and CD28 Signaling Domains Augment PI3kinase/AKT/Bcl-XL Activation and CD8+ T Cell-mediated Tumor Eradication, Molecular Therapy vol. 18 No. 2, 413-420 Feb. 2010.

* cited by examiner

USE OF TRANS-SIGNALING APPROACH IN CHIMERIC ANTIGEN RECEPTORS

CROSS-REFERENCE TO RELATED APPLICATIONS

The present application is a continuation of U.S. patent application Ser. No. 14/044,569, filed Oct. 2, 2013, issued as U.S. Pat. No. 10,117,896, which is entitled to priority under 35 U.S.C. § 119(e) to U.S. Provisional Patent Application No. 61/710,518, filed Oct. 5, 2012, each of which application is hereby incorporated by reference in their entireties herein.

BACKGROUND OF THE INVENTION

The genetic redirection of T cells with chimeric antigen receptors (CARs) that link an antigen-specific single-chain antibody fragment (scFv) to intracellular signaling domains is at the forefront of cancer immunotherapy (Jena et al., 2010, Blood 116:1035-1044; Gross et al., 1989, Proc. Natl. Acad. Sci. USA 86:10024-10028; Porter et al., 2011, N. Engl. J. Med. 365:725-733). CARs can functionally redirect T cells with high specificity to various surface antigens on tumor cells independent of MHC restriction and antigen processing, and therefore bypass major mechanisms by which tumors escape immune recognition. T cells bearing a first generation CAR having only the T cell CD3z intracellular signaling domain either fail to persist or become anergic since tumor cells frequently lack appropriate ligands for costimulatory molecules (Inman et al., 2007, Curr. Cancer Drug Targets 7:15-30). Indeed, incomplete activation of CART cells in vivo appears to limit their expansion and persistence in vivo, and thus hampered their efficacy in clinical trials in subjects with lymphoma (Till et al., 2008, Blood 112:2261-2271), neuroblastoma (Pule et al., 2008, Nat. Med. 14:1264-1270), or ovarian (Kershaw et al., 2006, Clin. Cancer Res. 12:6106-6115) or renal cancer (Lamers et al., 2006, J. Clin. Oncol. 24:e20-22).

To overcome these limitations, second generation CART cells were developed that incorporate the intracellular domain of various costimulatory molecules such as CD28, 4-1BB, OX-40, and CD27, leading to superior expansion, persistence and activity of the CART cells in preclinical mouse models (Carpenito et al., 2009, Proc. Natl. Acad. Sci. USA 106:3360-3365; Song et al., 2012, Blood 119:696-706) and in clinical studies (Porter et al., 2011, N. Engl. J. Med. 365:725-733; Kalos et al., 2011, Sci. Transl. Med. 3:95ra73; Savoldo et al., 2011, J. Clin. Invest. 121:1822-1826). However, the enhanced potency of the CARs can be associated with autoimmunity due to on-target toxicities against normal tissues expressing the lower levels of the tumor associated antigens, with two serious adverse events (SAEs) reported so far.

The first SAE occurred in a clinical trial where administration of anti-ErbB2 CART cells containing the CD28 and 4-1BB costimulatory signaling regions into a patient with refractory colon cancer with metastatic sites in lung and liver led to development of dramatic pulmonary toxicity with lung infiltrates and a cytokine storm followed by cardiac arrest and patient death (Morgan et al., 2010, Cancer J. 16:336-341). In the second report, a lymphodepleted patient with bulky chronic lymphocytic leukemia received autologous T cells engineered with an anti-CD19 second-generation CAR containing the CD28 domain at a total dose of $3\times10^7$ T cells/kg. This patient developed fever, hypotension, and dyspnea 20 hours after infusion, which rapidly progressed. Low grade sepsis was the most likely reason of the patient's death, however the possibility that a cyclophosphamide-induced "cytokine storm" may have enhanced the in vivo activation of modified T cells is well considered (Brentjens et al., 2010, Mol. Ther. 18:666-668). It is therefore clear that the development of strategies limiting potential early or late toxicity is mandatory.

A fully human anti-mesothelin CAR capable of conferring potent in vitro and in vivo effector functions to primary T cells against mesothelin-expressing tumors has previously been generated (Lanitis et al., 2012, Mol. Ther. 20:633-643). However, mesothelin CART cells hold the potential to inflict damage against normal mesothelial cells lining the pleura, peritoneum and peritoneum as well as epithelial cells of the trachea, tonsils, fallopian tube and the rete testis which express low levels of mesothelin (Chang et al., 1992, Int. J. Cancer 50:373-381; Ordonez, 2003, Mod. Pathol. 16:192-197).

There is thus a need in the art for CAR therapies that do not exhibit serious adverse events. The present invention addresses this unmet need in the art.

BRIEF SUMMARY OF THE INVENTION

The invention includes a trans-signaling composition comprising a nucleic acid molecule comprising a sequence encoding a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor.

In one embodiment, the costimulatory molecule is selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof. In another embodiment, the intracellular domain of the T cell receptor is a CD3z signaling domain. In yet another embodiment, at least one of the first and second antigen binding domain is an antibody or antigen-binding fragment thereof. In a further embodiment, antigen-binding fragment is a Fab or a scFv. In another embodiment, the first and second antigen binding domains are different from one another and in a further embodiment, the first and second transmembrane domains are different from one another. In an additional embodiment, the first antigen binding domain binds a first target and the second antigen binding domain binds a second target, wherein the first and second target are each a tumor antigen associated with a solid tumor. In another embodiment, the tumor antigen is selected from the group consisting of folate (FRa), mesothelin, EGFRvIII, IL-13Ra, EGFR, CA-IX, MUC1, HER2, and any combination thereof. In yet a further embodiment, first antigen binding domain binds to a target selected from the group consisting of mesothelin and folate receptor, and wherein the second antigen binding domain binds to a target selected from the group consisting of mesothelin and folate receptor.

The invention also includes a cell comprising a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor. In one embodiment, the cell is a T cell. In another embodiment, the T cell is dependent on the binding of the first CAR to its corresponding target and the binding of the second CAR to its corresponding target. In a further embodiment, the cell exhibits anti-tumor immunity when the first CAR binds to its corresponding target and the second CAR binds to its corresponding target. In an additional embodiment, the cell exhibits heightened tumor specificity.

Also included in the invention is a method for stimulating a T cell-mediated immune response to a target cell population or tissue in a mammal. The method comprises administering to a mammal an effective amount of a cell comprising a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor, thereby stimulating a T cell-mediated immune response to a target cell population or tissue in the mammal.

The invention further includes a method of providing an anti-tumor immunity in a mammal. The method comprises administering to the mammal an effective amount of a cell comprising a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor, thereby providing an anti-tumor immunity in the mammal.

Also included in the invention is a method of treating a mammal having a disease, disorder or condition associated with an elevated expression of a tumor antigen. The method comprises administering to the mammal an effective amount of a cell comprising a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor, thereby treating the mammal.

The invention additionally includes a method of treating a human with cancer. The method comprises administering to the human a T cell comprising a first CAR and a second CAR, wherein the first CAR comprises a first antigen binding domain, a first transmembrane domain, and an intracellular domain of a costimulatory molecule and wherein the second CAR comprises a second antigen binding domain, a second transmembrane domain, and an intracellular domain of a T cell receptor.

The invention further includes a method for enhancing a T cell-mediated immune response in a mammal. The method comprises administering an effective amount of a cell genetically modified to express a CAR comprising an antigen binding domain, a transmembrane domain, and an intracellular domain of a costimulatory molecule, wherein CAR does not comprise an intracellular domain of a T cell receptor.

In one embodiment, the costimulatory molecule is selected from the group consisting of CD27, CD28, 4-1BB, OX40, CD30, CD40, PD-1, lymphocyte function-associated antigen-1 (LFA-1), CD2, CD7, LIGHT, NKG2C, B7-H3, a ligand that specifically binds with CD83, and any combination thereof. In another embodiment, the antigen binding domain of the CAR is an antibody or antigen-binding fragment thereof.

In a further embodiment, the fragment is a Fab or a scFv. In yet another embodiment, the CAR functions with an independent receptor to induce a T cell response. In an additional embodiment, the independent receptor is selected from the group consisting of an endogenous T cell receptor, an exogenous T cell receptor, a CD3z-containing CAR, and any combination thereof.

BRIEF DESCRIPTION OF THE DRAWINGS

The following detailed description of preferred embodiments of the invention will be better understood when read in conjunction with the appended drawings. For the purpose of illustrating the invention, there are shown in the drawings embodiments which are presently preferred. It should be understood, however, that the invention is not limited to the precise arrangements and instrumentalities of the embodiments shown in the drawings.

FIG. 1, comprising FIG. 1A is a schematic representation of the anti-mesothelin (P4) based Chimeric Antigen Receptor (CAR) constructs containing the CD3ζ cytosolic domain alone (P4-z) or in combination with the CD28 costimulatory module (P4-28z). FIG. 1B is a schematic representation of the anti-aFR (F) based CAR constructs containing the scFv (MOV-19) fused through the CD8 hinge and CD28 TM to the CD28 costimulatory module (P4-28z). A truncated anti-aFR with no signaling domains is shown. P4, anti-mesothelin scFv; VL, variable L chain; L, Linker; VH, variable H chain; TM, transmembrane region. FIG. 1C is a series of graphs depicting P4 CAR expression. P4 CAR expression was detected on human CD3-gated cells via recombinant mesothelin protein staining after transduction with lentivirus compared to untransduced T cells. T cells bearing the F-28 CAR were detected via GFP transgene expression. Transduction efficiencies are indicated with the percentage of CAR expression of the transduced populations.

FIG. 2, comprising FIG. 2A is a series of graphs depicting the surface expression of mesothelin and/or FR by genetically modified C30 tumor cells. The native human ovarian cancer cell line C30 which does not express human mesothelin or FRa was engineered to express high surface levels of human mesothelin and/or FRa as shown by flow cytometry; Cells were also stained with proper isotype antibody controls. FIG. 2B is a graph depicting how primary human T cells transduced with P4-z and F-28 CARs exert superior IFN-g secretion compared to P4-z CAR T cells. Transduced T cells ($1 \times 10^5$ T cells) were cultured alone (none) or stimulated overnight with an equal number of antigen-negative C30 cells or C30 cells expressing mesothelin and/or FRa. Cell-free supernatant was harvested after about 20 hours of incubation and the IFN-g levels were measure with ELISA. FIG. 2C is a series of graphs depicting the co-expression of mesothelin and FRa in A1847 ovarian cancer cell line. FIG. 2D is a graph depicting how trans-signaling CART cells secreted higher levels of IFN-γ in response to A1847. Transduced T cells ($1 \times 10^5$ T cells) were cultured alone (none) or stimulated overnight with an equal number of antigen-negative C30 cells or A1857 cells expressing mesothelin and FRa. Cell-free supernatant was harvested after about 20 hours of incubation and the IFN-γ levels were measure with ELISA. Mean IFN-γ concentration±SEM (pg/ml) from duplicate cultures is shown. FIG. 2E is a graph depicting how trans-signaling CART cells secreted higher levels of IL-2 in response to A1847. Cell-free supernatant from three independent cultures was harvested and pooled after 20 hours of incubation and the IL-2 cytokine was quantified using cytometric bead array technology. Values represent cytokine concentration (pg/ml)

FIG. 3, comprising FIG. 3A is a series of graphs depicting how dual CAR T cells exert superior degranulation and express T cell activation markers in response to mesothelin-specific stimulation. First generation, cis or trans costimulated CAR T cells were cultured with the indicated antigen-negative tumor cells or tumor cells expressing FRa or mesothelin or both antigens for 5 hours while being stained by an anti-CD107a, b antibody conjugated with FITC. After the incubation period, T cells were stained for CD8 and CD69 and analyzed by flow cytometry. FIG. 3B is a series of graphs depicting cytolytic function of dual CAR transduced T cells. Primary human T cells transduced to express M-z, M-z/F-28, M-28z, F-28 or GFP were co-cultured with $Cr^{51}$-labeled native C30-F, C30-M and A1847 cancer cell lines for 4 hours at the indicated effector to target ratio. Percent specific target cell lysis was calculated as (experimental−spontaneous release)÷(maximal−spontaneous release)×100. Error bars indicate standard deviation.

FIG. 4, comprising FIG. 4A is a series of graphs depicting a mixed CAR T cell population containing dual CAR transduced T cells (M-z/F-28), single CAR transduced T cells (M-z or F-28) and untransduced T cells stimulated with A1847($M^+/F^+$) cancer cells for three days. In parallel second generation M-28z CAR T cells were co-cultured with A1847 for the same time period. After 3 days of coculture, apoptosis was quantified using annexin V and 7-AAD staining. FIG. 4B is a series of graphs depicting the absence of antigen induced cell death (AICD) in CAR T cells stimulated with antigen negative cancer cells. All the above CAR T cells populations were co-cultured with C30 ($M^−/F^−$) for 3 days. Annexin V and 7-AAD staining was performed to evaluate apoptosis.

FIG. 5, comprising FIG. 5A is a graph depicting the in vivo suppression of large pre-established tumors by M-z/F-28 CAR T cells: effect of the CD28 costimulatory signaling domain in trans. NSG mice bearing established s.c. tumor were treated with two i.v. injections of 7.5×10⁶ M-z, M-z/F-28 and M-28z $CAR^+$ T cells or control anti-CD1928z and GFP T cells or saline on 55 and 59 post-tumor inoculation. Tumor growth was assessed by caliper measurement. Tumors treated with M-z/F-28 and M-28z CAR-transduced T cells rapidly regressed (arrows indicate days of T cell infusion); tumors treated with saline, GFP or CD19-28z CAR transduced T cells did not regress 3 weeks post-first T cell dose (p<0.05). Equal doses of P4-z CAR-transduced T cells only slowed the tumor growth (p=0.05). Results are expressed as a mean tumor volume ($mm^3$±SEM) with n=5 for all groups. FIG. 5B is a graph depicting how the A1847 fLuc+ bioluminescence signal is similar in M-z/F-28 and M-28z CAR treated mice and weaker than M-z treated mice 4 weeks after the first T cell dose. Control treatment groups show no decrement in the bioluminescence signal. FIG. 5C is a series of photographs depicting the stable persistence of CD28 cis or trans costimulated CAR engineered human T cells in vivo. Peripheral blood was collected 2 weeks after the first T cell infusion and quantified for the absolute number of human $CD4^+$ and $CD8^+$ T cells/ul of blood. Mean cell count±SEM is shown with n=5 for all groups.

FIG. 6, comprising FIGS. 6A-6C depict the in vivo anti-tumor efficacy of trans- or cis-signaling T cells against A1847 cells expressing or lacking FRa. 5×10⁶ A1847($M^+/F^+$) and A1847($M^+/F^−$) cells were inoculated s.c. separately in the same NSG mice on opposite hind flanks. Mice with the two established A1847 (≥330mm³) tumors received tail vein injections of CART cells on days 45 and 49 post-tumor inoculation. Tumor growth was assessed by caliper measurement. FIG. 6A is a graph depicting how control of A1847$M^+/F^+$ tumor outgrowth was identical between the trans M-z/F-28 CART and cis-signaling M-28z CART cell groups. FIG. 6B is a graph depicting how inhibition of A1847$M^+/F^−$ outgrowth was partially but significantly attenuated in the trans M-z/F-28 CART cell group compared with the cis M-28z mice group. Results are expressed as a mean tumor volume ($mm^3$±SEM) with n=5 for all groups. FIG. 6C is a graph depicting how trans-signaling CART cells were statistically less effective in inhibiting the outgrowth of A1847$M^+/F^−$, compared with their activity against the A1847$M^+/F^+$ tumor in the same mice. Results are expressed as a mean tumor volume ($mm^3$±SEM) with n=5 for all groups. FIG. 6D is a graph depicting how the FLuc+ bioluminescence signal from A1847$M^+/F^+$ tumors is dramatically lower compared with the signal derived from the A1847$M^+/F^−$ tumors in the same mice treated with M-z/F-28 CAR T cells 4 weeks after the first T cell dose. FLuc+ bioluminescence signal from the different types of tumor is low and similar in the M-28z treated mouse group. Control treatment groups show no decrement in the bioluminescence signal.

FIG. 7, comprising FIG. 7A is a series of photographs depicting NSG mice with s.c. established A1847 tumors expressing or not expressing FRa in opposite flanks. The mice were treated with two i.v. injections of 7.5×10⁶ T cells expressing CD19-28z (top), M-z/F-28 (middle), or M-28z (bottom) on days 45 and 49 post-tumor inoculation. Mice were euthanized after four weeks and tumors were collected and stained for human CD3 expression (brown) of proper isotype control. Representative sections for both tumor derivatives are shown at ×10 magnifications. FIG. 7B is a graph depicting the quantification of $CD3^+$ T cells within the A1847 (M+/F+) and A1847 (M+/F−) tumors in the differentially treated groups. $CD3^+$ T cells were counted in 10 randomly selected intratumoral fields of each slide at high magnification (20×). Data are expressed as the means±SE with n=5 for all groups.

FIG. 9, comprising FIG. 9A is a series of graphs depicting the surface expression of mesothelin and/or FR by genetically modified A1847 tumor cells. The native human ovarian cancer cell line A1847 which express human mesothelin and FRa was transduced with lentiviral particles encoding for an shRNA specific for silencing aFR gene expression. Cells were also stained with an anti-mesothelin reagent (P4 Bb) or proper isotype antibody controls. aFR expression was unaltered after engineering cells with control shRNA (A1847M+/F+). FIG. 9B is a graph depicting IFN-γ secretion by trans M-z/F-28 CART cells was significantly reduced in response to A1847M+/F− compared with A1847M+/F+. Transduced T cells ($1 \times 10^5$ T cells) were cultured alone (none) or stimulated overnight with an equal number of C30 cells, (A1847M+/F+) or (A1847M+/F−). Cell-free supernatant was harvested after about 20 hours of incubation and the IFN-γ levels were measure with ELISA. Mean IFN-γ concentration±SEM (pg/ml) from duplicate cultures is shown.

FIG. 11, comprising FIG. 11A is a schematic representation of the first generation CAR and the second generation CAR, which contains CD3z and CD28 in a cis-signaling conformation. FIG. 11B depicts a costimulatory CAR comprising the 4-1BB intracellular signaling domain. FIG. 11C is a graph depicting the functionality of the FR-BB costimulatory CAR in the trans-signaling approach.

DETAILED DESCRIPTION

Figures 1A, 1B:
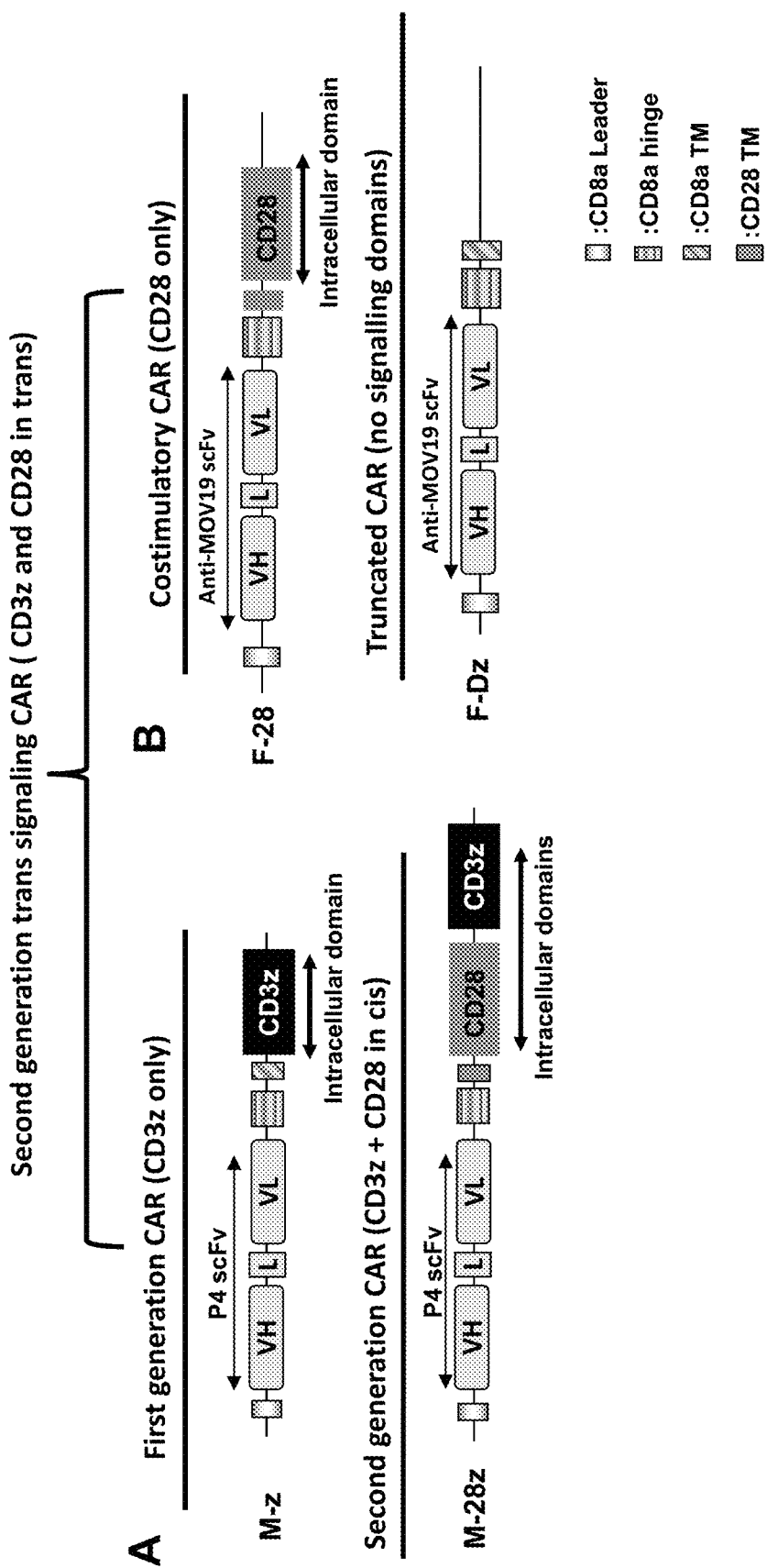
FIGS. 1A-1C, depicts the generation and expression of mesothelin and aFR specific CARs.
Figure 1C:
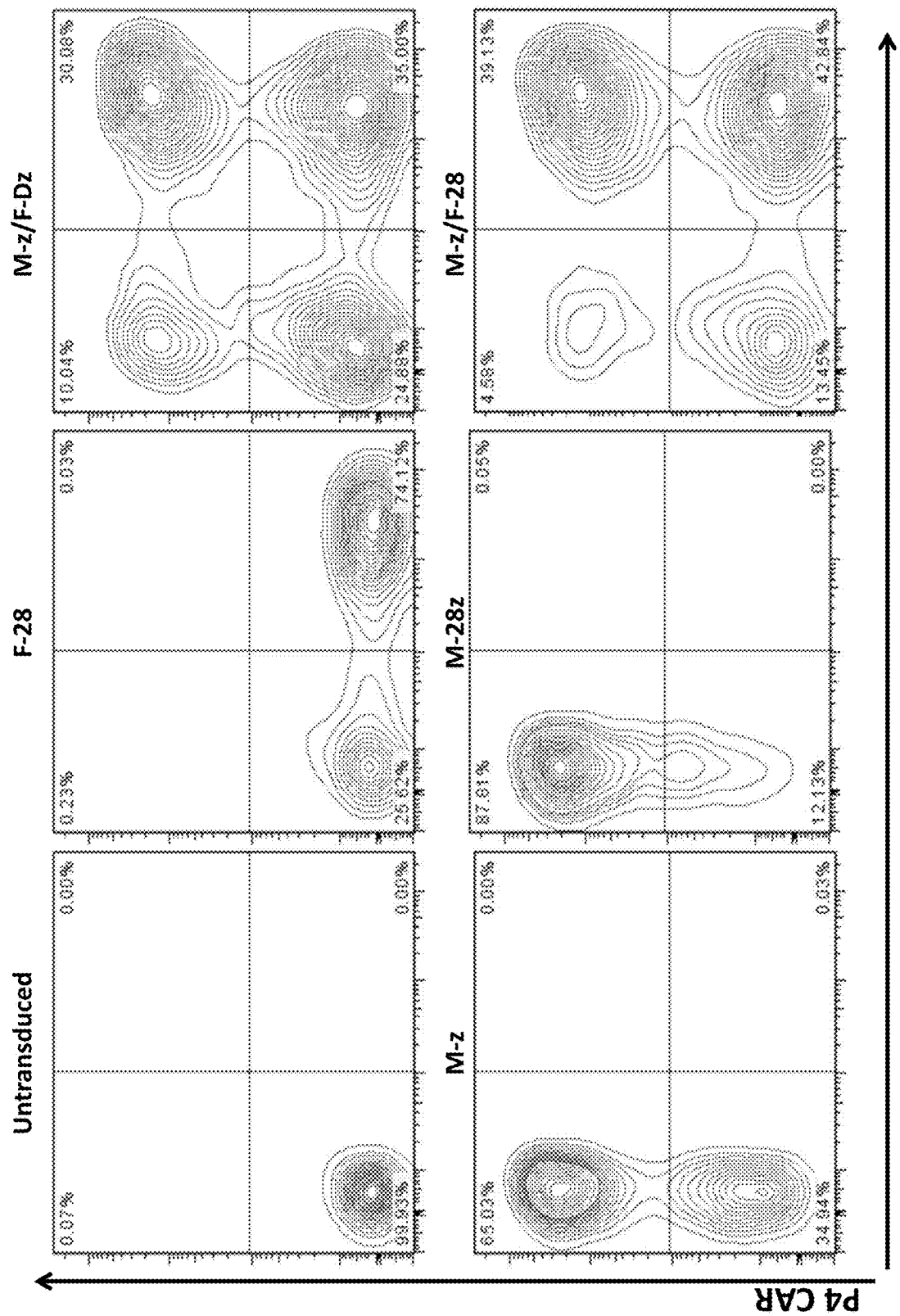

The present invention provides compositions and methods to regulate the specificity and activity of T cells modified to express a chimeric antigen receptor (CAR). T cells that have been genetically modified to express a CAR have been used in treatments for cancers where the CAR redirects the modified T cell to recognize a tumor antigen. The present invention also provides cells comprising a plurality of types of CARs, wherein the plurality of types of CARs participate in trans-signaling to induce T cell activation. In this aspect, CAR as used herein refers to a chimeric protein that comprises an antigen binding moiety and an intracellular signaling moiety. In some instances, it may be beneficial to effectively control and regulate CAR T cells such that they kill tumor cells while not affecting normal bystander cells. Thus, in one embodiment, the present invention also provides methods of killing cancerous cells while minimizing the depletion of normal non-cancerous cells, thereby improving the specificity of CAR therapy.

The present invention also provides a trans-signaling CAR approach. The trans-signaling CAR approach includes the physical separation of a plurality of types of CARs expressed on a cell, where binding of a plurality of types of CARs to their target antigen is required for CAR T cell activation. For example in the trans-signaling CAR approach, each CAR from the plurality of type of CARs have different intracellular signaling domain. For example, when a plurality of types of CARs is used to induce CAR T cell activation, the first type of CAR can only comprise an intracellular domain from a T cell receptor and the second type of CAR can only comprise an intracellular domain from a co-stimulatory molecule. In this manner, optimal CAR T cell activation occurs only when the intracellular domain of the T cell receptor from the first CAR is active and the intracellular domain of the co-stimulatory molecule from the second CAR is active in the T cell.

In one embodiment, the methods of the invention comprise genetically modifying a T cell to express a plurality of types of CARs, where T cell activation is dependent on the binding of a plurality of types of CARs to their target antigens. In one embodiment, dependence on the binding of a plurality of different CARs improves the specificity of CAR T cell therapies. In one embodiment, the trans-signaling CAR cells comprise a first signal module and a distinct second signal module which are incorporated into two distinct CARs, a first CAR and a second CAR, respectively, each with a different antigen specificity. In one embodiment, activation of the modified T cell only occurs when the first CAR binds the first desired antigen and the second CAR binds to the second desired antigen. In one embodiment, the first CAR comprises a primary signaling domain derived from CD3z, and the second CAR comprises a costimulatory signaling region.

In one embodiment, the genetically modified trans-signaling CAR T cells of the invention can be generated by introducing a lentiviral vector comprising one or more desired CARs into a T cell. In one embodiment, the modified T cells of the invention can be generated by introducing a plurality of lentiviral vectors each comprising one or more desired CARs into a T cell. In one embodiment, the modified T cells of the invention are able to replicate in vivo resulting in long-term persistence that can lead to sustained tumor control.

In one embodiment, the genetically modified trans-signaling CAR T cells of the invention can be generated by transfecting an RNA encoding one or more desired CARs into a T cell. In one embodiment, the modified T cells of the invention can be generated by transfecting a plurality of RNA sequences each encoding one ore more desired CARs into a T cell. In one embodiment, both the CAR and the bispecific antibody are transiently expressed in the genetically modified T cells.

In one embodiment, the genetically modified trans-signaling CAR T cells of the invention can be generated by transfecting an RNA encoding one or more desired CARs into a T cell, and introducing a lentiviral vector comprising one or more desired CARs into the T cell.

The present invention also provides costimulatory-only CARs. Costimulatory-only CARs comprise at least one costimulatory signaling region. In one embodiment, costimulatory-only CARs augment T cell activation through signaling mediated by the costimulatory signaling region. In one embodiment, binding of the costimulatory-only CAR to its target antigen is insufficient to induce T cell activation on its own. For example, the costimulatory-only CAR of the invention functions in combination with at least one other independent receptor of the T cell to induce T cell activation. The other independent receptor includes, but is not limited to, an endogenous T cell receptor, an exogenous T cell receptor, a CD3z containing CAR, and the like. The present invention also provides methods of improving T cell activation by administering a costimulatory-only CAR to a T cell or T cell population. In one embodiment, the T cell is used in adoptive T cell therapy or adoptive T cell transfer.

Definitions

Unless defined otherwise, all technical and scientific terms used herein have the same meaning as commonly understood by one of ordinary skill in the art to which the invention pertains. Although any methods and materials similar or equivalent to those described herein can be used in the practice for testing of the present invention, the preferred materials and methods are described herein. In describing and claiming the present invention, the following terminology will be used.

It is also to be understood that the terminology used herein is for the purpose of describing particular embodiments only, and is not intended to be limiting.

The articles "a" and "an" are used herein to refer to one or to plurality (i.e., to at least one) of the grammatical object of the article. By way of example, "an element" means one element or plurality element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

"Activation," as used herein, refers to the state of a T cell that has been sufficiently stimulated to induce detectable cellular proliferation. Activation can also be associated with induced cytokine production, and detectable effector functions. The term "activated T cells" refers to, among other things, T cells that are undergoing cell division.

The term "antibody," as used herein, refers to an immunoglobulin molecule which specifically binds with an antigen. Antibodies can be intact immunoglobulins derived from natural sources or from recombinant sources and can be immunoreactive portions of intact immunoglobulins. Antibodies are often of immunoglobulin molecules. The antibodies in the present invention may exist in a variety of forms including, for example, polyclonal antibodies, monoclonal antibodies, Fv, Fab and F(ab)2, as well as single chain antibodies and humanized antibodies (Harlow et al., 1999, In: Using Antibodies: A Laboratory Manual, Cold Spring Harbor Laboratory Press, NY; Harlow et al., 1989, In: Antibodies: A Laboratory Manual, Cold Spring Harbor, N.Y.; Houston et al., 1988, Proc. Natl. Acad. Sci. USA 85:5879-5883; Bird et al., 1988, Science 242:423-426).

The term "antibody fragment" refers to a portion of an intact antibody and refers to the antigenic determining variable regions of an intact antibody. Examples of antibody fragments include, but are not limited to, Fab, Fab', F(ab')2, and Fv fragments, linear antibodies, scFv antibodies, and multispecific antibodies formed from antibody fragments.

An "antibody heavy chain," as used herein, refers to the larger of the two types of polypeptide chains present in all antibody molecules in their naturally occurring conformations.

An "antibody light chain," as used herein, refers to the smaller of the two types of polypeptide chains present in all antibody molecules in their naturally occurring conformations. ☐ and ☐ light chains refer to the two major antibody light chain isotypes.

By the term "synthetic antibody" as used herein, is meant an antibody which is generated using recombinant DNA technology, such as, for example, an antibody expressed by a bacteriophage as described herein. The term should also be construed to mean an antibody which has been generated by the synthesis of a DNA molecule encoding the antibody and which DNA molecule expresses an antibody protein, or an amino acid sequence specifying the antibody, wherein the DNA or amino acid sequence has been obtained using synthetic DNA or amino acid sequence technology which is available and well known in the art.

The term "antigen" or "Ag" as used herein is defined as a molecule that provokes an immune response. This immune response may involve either antibody production, or the activation of specific immunologically-competent cells, or both. The skilled artisan will understand that any macromolecule, including virtually all proteins or peptides, can serve as an antigen. Furthermore, antigens can be derived from recombinant or genomic DNA. A skilled artisan will understand that any DNA, which comprises a nucleotide sequences or a partial nucleotide sequence encoding a protein that elicits an immune response therefore encodes an "antigen" as that term is used herein. Furthermore, one skilled in the art will understand that an antigen need not be encoded solely by a full length nucleotide sequence of a gene. It is readily apparent that the present invention includes, but is not limited to, the use of partial nucleotide sequences of one, or more than one, gene and that these nucleotide sequences are arranged in various combinations to elicit the desired immune response. Moreover, a skilled artisan will understand that an antigen need not be encoded by a "gene" at all. It is readily apparent that an antigen can be generated synthesized or can be derived from a biological sample. Such a biological sample can include, but is not limited to a tissue sample, a tumor sample, a cell or a biological fluid.

The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of the peptides, polynucleotides, cells and antibodies of the invention in prevention of the occurrence of tumor in the first place.

The term "auto-antigen" means, in accordance with the present invention, any self-antigen which is recognized by the immune system as if it were foreign. Auto-antigens comprise, but are not limited to, cellular proteins, phosphoproteins, cellular surface proteins, cellular lipids, nucleic acids, glycoproteins, including cell surface receptors.

The term "autoimmune disease" as used herein is defined as a disorder that results from an autoimmune response. An autoimmune disease is the result of an inappropriate and excessive response to a self-antigen. Examples of autoimmune diseases include but are not limited to, Addison's disease, alopecia areata, ankylosing spondylitis, autoimmune hepatitis, autoimmune parotitis, Crohn's disease, diabetes (Type I), dystrophic epidermolysis bullosa, epididymitis, glomerulonephritis, Graves' disease, Guillain-Barr syndrome, Hashimoto's disease, hemolytic anemia, systemic lupus erythematosus, multiple sclerosis, myasthenia gravis, pemphigus vulgaris, psoriasis, rheumatic fever, rheumatoid arthritis, sarcoidosis, scleroderma, Sjogren's syndrome, spondyloarthropathies, thyroiditis, vasculitis, vitiligo, myxedema, pernicious anemia, ulcerative colitis, among others.

As used herein, the term "autologous" is meant to refer to any material derived from the same individual to which it is later to be re-introduced into the individual.

"Allogeneic" refers to a graft derived from a different animal of the same species.

"Xenogeneic" refers to a graft derived from an animal of a different species.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like.

"Co-stimulatory ligand," as the term is used herein, includes a molecule on an antigen presenting cell (e.g., an aAPC, dendritic cell, B cell, and the like) that specifically binds a cognate co-stimulatory molecule on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like. A co-stimulatory ligand can include, but is not limited to, CD7, B7-1 (CD80), B7-2 (CD86), PD-L1, PD-L2, 4-1BBL, OX40L, inducible costimulatory ligand (ICOS-L), intercellular adhesion molecule (ICAM), CD3OL, CD40, CD70, CD83, HLA-G, MICA, MICB, HVEM, lymphotoxin beta receptor, 3/TR6, ILT3, ILT4, HVEM, an agonist or antibody that binds Toll ligand receptor and a ligand that specifically binds with B7-H3. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

A "co-stimulatory molecule" refers to the cognate binding partner on a T cell that specifically binds with a co-stimulatory ligand, thereby mediating a co-stimulatory response by the T cell, such as, but not limited to, proliferation. Co-stimulatory molecules include, but are not limited to an MHC class I molecule, BTLA and a Toll ligand receptor.

A "co-stimulatory signal", as used herein, refers to a signal, which in combination with a primary signal, such as TCR/CD3 ligation, leads to T cell proliferation and/or upregulation or downregulation of key molecules.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

An "effective amount" as used herein, means an amount which provides a therapeutic or prophylactic benefit.

"Encoding" refers to the inherent property of specific sequences of nucleotides in a polynucleotide, such as a gene, a cDNA, or an mRNA, to serve as templates for synthesis of other polymers and macromolecules in biological processes having either a defined sequence of nucleotides (i.e., rRNA, tRNA and mRNA) or a defined sequence of amino acids and the biological properties resulting therefrom. Thus, a gene encodes a protein if transcription and translation of mRNA corresponding to that gene produces the protein in a cell or other biological system. Both the coding strand, the nucleotide sequence of which is identical to the mRNA sequence and is usually provided in sequence listings, and the non-coding strand, used as the template for transcription of a gene or cDNA, can be referred to as encoding the protein or other product of that gene or cDNA.

As used herein "endogenous" refers to any material from or produced inside an organism, cell, tissue or system.

As used herein, the term "exogenous" refers to any material introduced to an organism, cell, tissue or system that was produced outside an organism, cell, tissue or system.

The term "expression" as used herein is defined as the transcription and/or translation of a particular nucleotide sequence.

"Expression vector" refers to a vector comprising a recombinant polynucleotide comprising expression control sequences operatively linked to a nucleotide sequence to be expressed. An expression vector comprises sufficient cis-acting elements for expression; other elements for expression can be supplied by the host cell or in an in vitro expression system. Expression vectors include all those known in the art, such as cosmids, plasmids (e.g., naked or contained in liposomes) and viruses (e.g., lentiviruses, retroviruses, adenoviruses, and adeno-associated viruses) that incorporate the recombinant polynucleotide.

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared X 100. For example, if 6 of 10 of the positions in two sequences are matched or homologous then the two sequences are 60% homologous. By way of example, the DNA sequences ATTGCC and TATGGC share 50% homology. Generally, a comparison is made when two sequences are aligned to give maximum homology.

The term "immunoglobulin" or "Ig," as used herein is defined as a class of proteins, which function as antibodies. Antibodies expressed by B cells are sometimes referred to as the BCR (B cell receptor) or antigen receptor. The five members included in this class of proteins are IgA, IgG, IgM, IgD, and IgE. IgA is the primary antibody that is present in body secretions, such as saliva, tears, breast milk, gastrointestinal secretions and mucus secretions of the respiratory and genitourinary tracts. IgG is the most common circulating antibody. IgM is the main immunoglobulin produced in the primary immune response in most subjects. It is the most efficient immunoglobulin in agglutination, complement fixation, and other antibody responses, and is important in defense against bacteria and viruses. IgD is the immunoglobulin that has no known antibody function, but may serve as an antigen receptor. IgE is the immunoglobulin that mediates immediate hypersensitivity by causing release of mediators from mast cells and basophils upon exposure to allergen.

As used herein, an "instructional material" includes a publication, a recording, a diagram, or any other medium of expression which can be used to communicate the usefulness of the compositions and methods of the invention. The instructional material of the kit of the invention may, for example, be affixed to a container which contains the nucleic acid, peptide, and/or composition of the invention or be shipped together with a container which contains the nucleic acid, peptide, and/or composition. Alternatively, the instructional material may be shipped separately from the container with the intention that the instructional material and the compound be used cooperatively by the recipient.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

In the context of the present invention, the following abbreviations for the commonly occurring nucleic acid bases are used. "A" refers to adenosine, "C" refers to cytosine, "G" refers to guanosine, "T" refers to thymidine, and "U" refers to uridine.

Unless otherwise specified, a "nucleotide sequence encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

A "lentivirus" as used herein refers to a genus of the Retroviridae family. Lentiviruses are unique among the retroviruses in being able to infect non-dividing cells; they can deliver a significant amount of genetic information into the DNA of the host cell, so they are one of the most efficient methods of a gene delivery vector. HIV, SIV, and FIV are all examples of lentiviruses. Vectors derived from lentiviruses offer the means to achieve significant levels of gene transfer in vivo.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

Unless otherwise specified, a "nucleotide sequence encoding an amino acid sequence" includes all nucleotide sequences that are degenerate versions of each other and that encode the same amino acid sequence. Nucleotide sequences that encode proteins and RNA may include introns.

The term "operably linked" refers to functional linkage between a regulatory sequence and a heterologous nucleic acid sequence resulting in expression of the latter. For example, a first nucleic acid sequence is operably linked with a second nucleic acid sequence when the first nucleic acid sequence is placed in a functional relationship with the second nucleic acid sequence. For instance, a promoter is operably linked to a coding sequence if the promoter affects the transcription or expression of the coding sequence. Generally, operably linked DNA sequences are contiguous and, where necessary to join two protein coding regions, in the same reading frame.

The term "overexpressed" tumor antigen or "overexpression" of a tumor antigen is intended to indicate an abnormal level of expression of a tumor antigen in a cell from a disease area like a solid tumor within a specific tissue or organ of the patient relative to the level of expression in a normal cell from that tissue or organ. Patients having solid tumors or a hematological malignancy characterized by overexpression of the tumor antigen can be determined by standard assays known in the art.

"Parenteral" administration of an immunogenic composition includes, e.g., subcutaneous (s.c.), intravenous (i.v.), intramuscular (i.m.), or intrasternal injection, or infusion techniques.

The terms "patient," "subject," "individual," and the like are used interchangeably herein, and refer to any animal, or cells thereof whether in vitro or in situ, amenable to the methods described herein. In certain non-limiting embodiments, the patient, subject or individual is a human.

The term "polynucleotide" as used herein is defined as a chain of nucleotides. Furthermore, nucleic acids are polymers of nucleotides. Thus, nucleic acids and polynucleotides as used herein are interchangeable. One skilled in the art has the general knowledge that nucleic acids are polynucleotides, which can be hydrolyzed into the monomeric "nucleotides." The monomeric nucleotides can be hydrolyzed into nucleosides. As used herein polynucleotides include, but are not limited to, all nucleic acid sequences which are obtained by any means available in the art, including, without limitation, recombinant means, i.e., the cloning of nucleic acid sequences from a recombinant library or a cell genome, using ordinary cloning technology and PCR, and the like, and by synthetic means.

As used herein, the terms "peptide," "polypeptide," and "protein" are used interchangeably, and refer to a compound comprised of amino acid residues covalently linked by peptide bonds. A protein or peptide must contain at least two amino acids, and no limitation is placed on the maximum number of amino acids that can comprise a protein's or peptide's sequence. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs, fusion proteins, among others. The polypeptides include natural peptides, recombinant peptides, synthetic peptides, or a combination thereof.

The term "promoter" as used herein is defined as a DNA sequence recognized by the synthetic machinery of the cell, or introduced synthetic machinery, required to initiate the specific transcription of a polynucleotide sequence.

As used herein, the term "promoter/regulatory sequence" means a nucleic acid sequence which is required for expression of a gene product operably linked to the promoter/regulatory sequence. In some instances, this sequence may be the core promoter sequence and in other instances, this sequence may also include an enhancer sequence and other regulatory elements which are required for expression of the gene product. The promoter/regulatory sequence may, for example, be one which expresses the gene product in a tissue specific manner.

A "constitutive" promoter is a nucleotide sequence which, when operably linked with a polynucleotide which encodes or specifies a gene product, causes the gene product to be produced in a cell under most or all physiological conditions of the cell.

An "inducible" promoter is a nucleotide sequence which, when operably linked with a polynucleotide which encodes or specifies a gene product, causes the gene product to be produced in a cell substantially only when an inducer which corresponds to the promoter is present in the cell.

A "tissue-specific" promoter is a nucleotide sequence which, when operably linked with a polynucleotide encodes or specified by a gene, causes the gene product to be produced in a cell substantially only if the cell is a cell of the tissue type corresponding to the promoter.

By the term "specifically binds," as used herein with respect to an antibody, is meant an antibody which recognizes a specific antigen, but does not substantially recognize or bind other molecules in a sample. For example, an antibody that specifically binds to an antigen from one species may also bind to that antigen from one or more species. But, such cross-species reactivity does not itself alter the classification of an antibody as specific. In another example, an antibody that specifically binds to an antigen may also bind to different allelic forms of the antigen. However, such cross reactivity does not itself alter the classification of an antibody as specific. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A," the presence of a molecule containing epitope A (or free, unlabeled A), in a reaction containing labeled "A" and the antibody, will reduce the amount of labeled A bound to the antibody.

By the term "stimulation," is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "stimulatory molecule," as the term is used herein, means a molecule on a T cell that specifically binds with a cognate stimulatory ligand present on an antigen presenting cell.

A "stimulatory ligand," as used herein, means a ligand that when present on an antigen presenting cell (e.g., an aAPC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like. Stimulatory ligands are well-known in the art and encompass, inter alia, an WIC Class I molecule loaded with a peptide, an anti-CD3 antibody, a superagonist anti-CD28 antibody, and a superagonist anti-CD2 antibody.

The term "subject," "patient" and "individual" are used interchangeably herein and are intended to include living organisms in which an immune response can be elicited (e.g., mammals). Examples of subjects include humans, dogs, cats, mice, rats, and transgenic species thereof.

As used herein, a "substantially purified" cell is a cell that is essentially free of other cell types. A substantially purified cell also refers to a cell which has been separated from other cell types with which it is normally associated in its naturally occurring state. In some instances, a population of substantially purified cells refers to a homogenous population of cells. In other instances, this term refers simply to cell that have been separated from the cells with which they are naturally associated in their natural state. In some embodiments, the cells are cultured in vitro. In other embodiments, the cells are not cultured in vitro.

The term "therapeutic" as used herein means a treatment and/or prophylaxis. A therapeutic effect is obtained by suppression, remission, or eradication of a disease state.

The term "therapeutically effective amount" refers to the amount of the subject compound that will elicit the biological or medical response of a tissue, system, or subject that is being sought by the researcher, veterinarian, medical doctor or other clinician. The term "therapeutically effective amount" includes that amount of a compound that, when administered, is sufficient to prevent development of, or alleviate to some extent, one or more of the signs or symptoms of the disorder or disease being treated. The therapeutically effective amount will vary depending on the compound, the disease and its severity and the age, weight, etc., of the subject to be treated.

To "treat" a disease as the term is used herein, means to reduce the frequency or severity of at least one sign or symptom of a disease or disorder experienced by a subject.

The term "transfected" or "transformed" or "transduced" as used herein refers to a process by which exogenous nucleic acid is transferred to, or introduced into, the host cell. A "transfected" or "transformed" or "transduced" cell is one which has been transfected, transformed or transduced with exogenous nucleic acid. The cell includes the primary subject cell and its progeny.

The phrase "under transcriptional control" or "operatively linked" as used herein means that the promoter is in the correct location and orientation in relation to a polynucleotide to control the initiation of transcription by RNA polymerase and expression of the polynucleotide.

A "vector" is a composition of matter which comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Thus, the term "vector" includes an autonomously replicating plasmid or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

The present invention provides compositions and methods for trans-signaling CAR cells, where binding of a plurality of types of CARs to their target antigen is required for CAR T cell activation. Dependence on the binding of a plurality of types of CARs improves the specificity of the lytic activity of the CAR T cell, thereby reducing the potential for depleting normal healthy tissue. In one embodiment, the trans-signaling CAR cells of the present invention comprise a first signal module and a second signal module which are incorporated into two distinct CARs, a first CAR and a second CAR, respectively, each with different antigen specificity and signaling modules.

In one embodiment, the first type of CAR only comprises an intracellular domain from a T cell receptor and the second type of CAR only comprises an intracellular domain from a co-stimulatory molecule. In this manner, optimal CAR T cell activation occurs when the intracellular domain of the T cell receptor from the first CAR is activated and the intracellular domain of the co-stimulatory molecule from the second CAR is activated in the T cell.

In one embodiment, the first CAR comprises a CD3z signaling domain and the second CAR comprises a costimulatory signaling region. This is because the present invention is partly based on the discovery that a trans-signaling CAR-mediated T-cell response comprising a CAR of each of a CD3z signaling and a costimulatory signaling region produces improved cytokine secretion and resistance to antigen-induced cell death (AICD) in vitro. In one embodiment, the trans-signaling CAR cells provide increased IL-2 production. In one embodiment, the trans-signaling CAR cells of the invention exhibit superior tumor specificity compared to cells expressing a single type of CAR comprising a costimulatory domain and a CD3z signaling domain. In one embodiment, the invention comprises CAR cells with a first CAR comprising a CD3z signaling domain, and a second CAR comprising a CD28 costimulatory signaling region.

The trans-signaling CAR cells of the present invention are comprised of a plurality of types of CARs, each specific for a different antigen. In one embodiment, a first CAR targets folate receptor (aFR), while a second CAR targets mesothelin (meso). This is because the present invention is partly based on the discovery that the CAR cells comprising the dual specificity can be selective for tumor over normal tissues expressing the lower levels of the tumor associated antigens (TAA), thereby reducing the potential for "on-target" toxicity, while maintaining potent anti-cancer activity, tumor localization and persistence in vivo as compared to first generation CARs. In one embodiment, T cell activation and lytic activity of trans-signaling CAR cells requires the co-expression of both aFR and mesothelin on the tumor cell surface. For example, ovarian cancers are known to express both aFR and mesothelin. As a result, trans-signaling CAR cells showed reduced targeting of cells expressing only one tumor associated antigen as compared to conventional second generation CARs, where CD3z and costimulatory signaling regions are in tandem. In one embodiment, the TAAs are nearly uniformly expressed on the surface of a cell of a particular cancer, while the TAAs are expressed in low and non-overlapping levels in normal tissue.

In some embodiments, the present invention is directed to retroviral or lentiviral vectors encoding one or more CARs stably integrated into a T cell and stably expressed therein. In other embodiments, the present invention is directed to RNA encoding one or more CARs that is transfected into a T cell and transiently expressed therein. Transient, non-integrated expression of the CARs mitigates concerns associated with permanent and integrated expression in a cell.

In one embodiment, the present invention provides methods to treat cancer and other disorders using CAR T cell therapy while limiting the depletion of healthy bystander cells. In one embodiment, the accumulation of T cells in tumors is increased when both antigens are expressed on the tumor cell surface as compared to only one antigen. In one embodiment, the dual CAR T cell approach can modestly improve safety for clinical application without significantly diminishing its antitumor potential. Additional approaches to limiting CART mediated autoimmune effects are also considered. In one embodiment, the optimal T cell dose can be defined by a careful design of a dose-escalation strategy. In one embodiment, conditional suicide genes can be co-expressed to overcome potential side effects of non-tumor cell recognition by CAR T cells. For example, HSV-TK, i-Casp9, the cytoplasmic domain of Fas, or an inducible caspase can be incorporated into genetically engineered T cells to prevent aberrant T cell responses. In one embodiment, T cells can be electroporated with optimized RNAs encoding for CARs to allow for transient CAR expression.

The antigen specificity of each CAR is not limited by whether the CAR comprises a signaling domain or a costimulatory signaling region. In one embodiment, the first CAR comprises a CD3z signaling domain and a mesothelin binding domain, and the second CAR comprises a CD28 costimulatory signaling region and a folate receptor binding domain. In one embodiment, the first CAR comprises a CD3z signaling domain and a folate receptor binding domain, and the second CAR comprises a CD28 costimulatory signaling region and a mesothelin binding domain. As described elsewhere herein, T cells modified to express a plurality of types of CARs can be generated by administering lentiviral vectors, in vitro transcribed RNA, or combination thereof, to the cells. The trans-signaling CAR cells can therefore be engineered to target any combination of antigens on the surface of a particular cell of interest in order to enhance the binding affinity of the CAR cells toward the cell of interest as well as to reduce non-selective binding to normal tissues.

The present invention also provides costimulatory-only CARs. In one embodiment, the costimulatory-only CAR comprises an antigen binding domain and at least one costimulatory domain. For example, in one embodiment, the costimulatory-only CAR of the invention comprises a CD28 costimulatory signaling region. In one embodiment, the costimulatory-only CAR of the invention comprises a 4-1BB (CD137) costimulatory signaling domain. In one embodiment, binding of the costimulatory-only CAR to its target antigen is insufficient to induce substantial T cell activation. In one embodiment, the costimulatory-only domain lacks a CD3z domain. In one embodiment, costimulatory-only CARs are used to enhance endogenous T cell activation. In another embodiment, costimulatory-only CARs are used to enhance T cell activation in T cells used for adoptive T cell transfer.

In one embodiment, the invention comprises controlling or regulating CAR T cell activity. In one embodiment, the invention comprises compositions and methods related to genetically modifying T cells to express a plurality of types of CARs, where CAR T cell activation is dependent on the binding of a plurality of types of CARs to their target receptor.

In one embodiment, the present invention provides methods for treating cancer and other disorders using CAR T cell therapies while minimizing the depletion of normal healthy tissue. The cancer may be a hematological malignancy, a solid tumor, a primary or a metastasizing tumor. Other diseases treatable using the compositions and methods of the invention include viral, bacterial and parasitic infections as well as autoimmune diseases.

Chimeric Antigen Receptors

The present invention provides a chimeric antigen receptor (CAR) comprising an extracellular and intracellular domain. Compositions and methods of making CARs have been described in PCT/US11/64191, which is incorporated in its entirety by reference herein.

The extracellular domain comprises a target-specific binding element otherwise referred to as an antigen binding domain. In some embodiments, the extracellular domain also comprises a hinge domain. In one embodiment, the hinge domain is CD8α. In one embodiment, the intracellular domain or otherwise the cytoplasmic domain comprises a zeta chain portion. In one embodiment, the intracellular domain or otherwise the cytoplasmic domain comprises a costimulatory signaling region. The costimulatory signaling region refers to a portion of the CAR comprising the intracellular domain of a costimulatory molecule. Costimulatory molecules are cell surface molecules other than antigen receptors or their ligands that are required for an efficient response of lymphocytes to antigen.

Between the extracellular domain and the transmembrane domain of the CAR, or between the cytoplasmic domain and the transmembrane domain of the CAR, there may be incorporated a spacer domain. As used herein, the term "spacer domain" generally means any oligo- or polypeptide that functions to link the transmembrane domain to, either the extracellular domain or, the cytoplasmic domain in the polypeptide chain. A spacer domain may comprise up to 300 amino acids, preferably 10 to 100 amino acids and most preferably 25 to 50 amino acids.

The present invention includes retroviral and lentiviral vector constructs expressing a CAR that can be directly transduced into a cell. The present invention also includes an RNA construct that can be directly transfected into a cell. A method for generating mRNA for use in transfection involves in vitro transcription (IVT) of a template with specially designed primers, followed by polyA addition, to produce a construct containing 3' and 5' untranslated sequence ("UTR"), a 5' cap and/or Internal Ribosome Entry Site (IRES), the gene to be expressed, and a polyA tail, typically 50-2000 bases in length. RNA so produced can efficiently transfect different kinds of cells. In one embodiment, the template includes sequences for the CAR.

Preferably, the CAR comprises an extracellular domain, a transmembrane domain and a cytoplasmic domain. The extracellular domain and transmembrane domain can be derived from any desired source of such domains. In some instances, the hinge domain of the CAR of the invention comprises the CD8α hinge domain.

In one embodiment, the CAR of the invention comprises a target-specific binding element otherwise referred to as an antigen binding domain. The choice of moiety depends upon the type and number of ligands that define the surface of a target cell. For example, the antigen binding domain may be chosen to recognize a ligand that acts as a cell surface marker on target cells associated with a particular disease state. Thus examples of cell surface markers that may act as ligands for the antigen moiety domain in the CAR of the invention include those associated with viral, bacterial and parasitic infections, autoimmune disease and cancer cells.

In one embodiment, the CAR of the invention can be engineered to target a tumor antigen of interest by way of engineering a desired antigen binding domain that specifically binds to an antigen on a tumor cell. In the context of the present invention, "tumor antigen" or "hyperporoliferative disorder antigen" or "antigen associated with a hyperproliferative disorder," refers to antigens that are common to specific hyperproliferative disorders such as cancer. The antigens discussed herein are merely included by way of example. The list is not intended to be exclusive and further examples will be readily apparent to those of skill in the art.

Tumor antigens are proteins that are produced by tumor cells that elicit an immune response, particularly T-cell mediated immune responses. The selection of the antigen binding domain of the invention will depend on the particular type of cancer to be treated. Tumor antigens are well known in the art and include, for example, a glioma-associated antigen, carcinoembryonic antigen (CEA), β-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostate-specific antigen (PSA), PAP, NY-ESO-1, LAGE-1a, p53, prostein, PSMA, Her2/neu, survivin and telomerase, prostate-carcinoma tumor antigen-1 (PCTA-1), MAGE, ELF2M, neutrophil elastase, ephrinB2, CD22, insulin growth factor (IGF)-I, IGF-II, IGF-I receptor, folate receptor (FRa) and mesothelin. In a preferred embodiment, the tumor antigen is selected from the group consisting of folate receptor (FRa), mesothelin, EGFRvIII, IL-13Ra, EGFR, CA-IX, MUC1, HER2, and any combination thereof. In one embodiment, the first CAR comprises an antigen binding domain which binds to mesothelin and the second CAR comprises an antigen binding domain that binds to FRa. In one embodiment, the CAR comprises an antigen binding domain that binds to HER2.

In one embodiment, the tumor antigen comprises one or more antigenic cancer epitopes associated with a malignant tumor. Malignant tumors express a number of proteins that can serve as target antigens for an immune attack. These molecules include but are not limited to tissue-specific antigens such as MART-1, tyrosinase and GP 100 in melanoma and prostatic acid phosphatase (PAP) and prostate-specific antigen (PSA) in prostate cancer. Other target molecules belong to the group of transformation-related molecules such as the oncogene HER-2/Neu/ErbB-2. Yet another group of target antigens are onco-fetal antigens such as carcinoembryonic antigen (CEA). In B-cell lymphoma the tumor-specific idiotype immunoglobulin constitutes a truly tumor-specific immunoglobulin antigen that is unique to the individual tumor. B-cell differentiation antigens such as CD19, CD20 and CD37 are other candidates for target antigens in B-cell lymphoma. Some of these antigens (CEA, HER-2, CD19, CD20, idiotype) have been used as targets for passive immunotherapy with monoclonal antibodies with limited success.

The type of tumor antigen referred to in the invention may also be a tumor-specific antigen (TSA) or a tumor-associated antigen (TAA). A TSA is unique to tumor cells and does not occur on other cells in the body. A TAA associated antigen is not unique to a tumor cell and instead is also expressed on a normal cell under conditions that fail to induce a state of immunologic tolerance to the antigen. The expression of the antigen on the tumor may occur under conditions that enable the immune system to respond to the antigen. TAAs may be antigens that are expressed on normal cells during fetal development when the immune system is immature and unable to respond or they may be antigens that are normally present at extremely low levels on normal cells but which are expressed at much higher levels on tumor cells.

Non-limiting examples of TSA or TAA antigens include the following: Differentiation antigens such as MART-1/

MelanA (MART-I), gp100 (Pmel 17), tyrosinase, TRP-1, TRP-2 and tumor-specific multilineage antigens such as MAGE-1, MAGE-3, BAGE, GAGE-1, GAGE-2, p15; overexpressed embryonic antigens such as CEA; overexpressed oncogenes and mutated tumor-suppressor genes such as p53, Ras, HER-2/neu; unique tumor antigens resulting from chromosomal translocations; such as BCR-ABL, E2A-PRL, H4-RET, IGH-IGK, MYL-RAR; and viral antigens, such as the Epstein Barr virus antigens EBVA and the human papillomavirus (HPV) antigens E6 and E7. Other large, protein-based antigens include TSP-180, MAGE-4, MAGE-5, MAGE-6, RAGE, NY-ESO, p185erbB2, p180erbB-3, c-met, nm-23H1, PSA, TAG-72, CA 19-9, CA 72-4, CAM 17.1, NuMa, K-ras, beta-Catenin, CDK4, Mum-1, p 15, p 16, 43-9F, 5T4, 791Tgp72, alpha-fetoprotein, beta-HCG, BCA225, BTAA, CA 125, CA 15-3\CA 27.29\BCAA, CA 195, CA 242, CA-50, CAM43, CD68\P1, CO-029, FGF-5, G250, Ga733\EpCAM, HTgp-175, M344, MA-50, MG7-Ag, MOV18, NB/70K, NY-CO-1, RCAS1, SDCCAG16, TA-90\Mac-2 binding protein\cyclophilin C-associated protein, TAAL6, TAG72, TLP, and TPS.

In a preferred embodiment, the antigen binding domain portion of the CAR targets an antigen that includes but is not limited to CD19, CD20, CD22, ROR1, Mesothelin, CD33/IL3Ra, c-Met, PSMA, Glycolipid F77, EGFRvIII, GD-2, MY-ESO-1 TCR, MAGE A3 TCR, folate receptor (FRa), and the like.

Depending on the desired antigen to be targeted, the CAR of the invention can be engineered to include the appropriate antigen bind moiety that is specific to the desired antigen target.

The antigen binding domain can be any domain that binds to the antigen including but not limited to monoclonal antibodies, polyclonal antibodies, synthetic antibodies, human antibodies, humanized antibodies, and fragments thereof. In some instances, it is beneficial for the antigen binding domain to be derived from the same species in which the CAR will ultimately be used in. For example, for use in humans, it may be beneficial for the antigen binding domain of the CAR to comprise a human antibody or fragment thereof. Thus, in one embodiment, the antigen biding domain portion comprises a human antibody or a fragment thereof. Alternatively, in some embodiments, a non-human antibody is humanized, where specific sequences or regions of the antibody are modified to increase similarity to an antibody naturally produced in a human.

In one embodiment of the present invention, a plurality of types of CARs is expressed on the surface of a T cell. The different types of CAR may differ in their antigen binding domain. That is, in one embodiment, the different types of CARs each bind a different antigen. In one embodiment, the different antigens are markers for a specific tumor. For example, in one embodiment, the different types of CARs each bind to a different antigen, where each antigen is expressed on a specific type of tumor. Examples of such antigens are discussed elsewhere herein.

With respect to the transmembrane domain, the CAR can be designed to comprise a transmembrane domain that is fused to the extracellular domain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex.

The transmembrane domain may be derived either from a natural or from a synthetic source. Where the source is natural, the domain may be derived from any membrane-bound or transmembrane protein. Transmembrane regions of particular use in this invention may be derived from (i.e. comprise at least the transmembrane region(s) of) the alpha, beta or zeta chain of the T-cell receptor, CD28, CD3 epsilon, CD45, CD4, CD5, CD8, CD9, CD16, CD22, CD33, CD37, CD64, CD80, CD86, CD134, CD137, CD154, ICOS. Alternatively the transmembrane domain may be synthetic, in which case it will comprise predominantly hydrophobic residues such as leucine and valine. Preferably a triplet of phenylalanine, tryptophan and valine will be found at each end of a synthetic transmembrane domain. Optionally, a short oligo- or polypeptide linker, preferably between 2 and 10 amino acids in length may form the linkage between the transmembrane domain and the cytoplasmic signaling domain of the CAR. A glycine-serine doublet provides a particularly suitable linker.

The cytoplasmic domain or otherwise the intracellular signaling domain of the CAR of the invention influences the activation of at least one of the normal effector functions of the immune cell in which the CAR has been placed in. The term "effector function" refers to a specialized function of a cell. Effector function of a T cell, for example, may be cytolytic activity or helper activity including the secretion of cytokines. Thus the term "intracellular signaling domain" refers to the portion of a protein which transduces the effector function signal and directs the cell to perform a specialized function. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

In one embodiment of the present invention, the effector function of the cell is dependent upon the binding of a plurality of types of CARs to their targeted antigen. For example, in one embodiment, binding of one type of CAR to its target is not sufficient to induce the effector function of the cell.

Examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

It is known that signals generated through the TCR alone are insufficient for full activation of the T cell and that a secondary or co-stimulatory signal is also required. Thus, T cell activation can be said to be mediated by two distinct classes of cytoplasmic signaling sequence: those that initiate antigen-dependent primary activation through the TCR (primary cytoplasmic signaling sequences) and those that act in an antigen-independent manner to provide a secondary or co-stimulatory signal (secondary cytoplasmic signaling sequences).

Primary cytoplasmic signaling sequences regulate primary activation of the TCR complex either in a stimulatory way, or in an inhibitory way. Primary cytoplasmic signaling sequences that act in a stimulatory manner may contain signaling motifs which are known as immunoreceptor tyrosine-based activation motifs or ITAMs.

Examples of ITAM containing primary cytoplasmic signaling sequences that are of particular use in the invention include those derived from TCR zeta, FcR gamma, FcR beta, CD3 gamma, CD3 delta, CD3 epsilon, CD5, CD22, CD79a, CD79b, and CD66d. It is particularly preferred that cytoplasmic signaling molecule in at least one CAR of the trans-signaling CAR cells of the invention comprises a cytoplasmic signaling sequence derived from CD3z.

In one embodiment, the cytoplasmic domain of the CAR can be designed to comprise a costimulatory signaling region. The costimulatory signaling region refers to a portion of the CAR comprising the intracellular domain of a costimulatory molecule. A costimulatory molecule is a cell surface molecule other than an antigen receptor or their ligands that is required for an efficient response of lymphocytes to an antigen. Examples of such molecules include CD27, CD28, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83, and the like.

The cytoplasmic signaling sequences within the cytoplasmic signaling portion of the CAR of the invention may be linked to each other in a random or specified order. Optionally, a short oligo- or polypeptide linker, preferably between 2 and 10 amino acids in length may form the linkage. A glycine-serine doublet provides a particularly suitable linker.

In one embodiment, the cytoplasmic domain is designed to comprise the signaling domain of CD3-zeta. In another embodiment, the cytoplasmic domain is designed to comprise the signaling domain of 4-1BB. In another embodiment, the cytoplasmic domain is designed to comprise the signaling domain of CD28. In one embodiment of the present invention, a plurality of types of CARs is expressed on a cell, where the different types of CAR may vary in their cytoplasmic domain. In one embodiment, at least one type of CAR comprises the CD3z domain, while at least one type of CAR comprises a costimulatory signaling region, for example the 4-1BB domain. However, the different types of CARs are not limited by any particular cytoplasmic domain. For example, each type of CAR can comprise any ITAM containing sequence, costimulatory signaling region, or combination thereof such that binding of each individual type of CAR is insufficient to induce effector function but binding of a plurality of types of CARs are able to induce effector function. That is, the domains of each type of CAR work together to induce effector function.

The present invention further provides for a costimulatory-only CAR, wherein the CAR comprises an antigen binding domain and at least one costimulatory domain. In a preferred embodiment, the costimulatory-only domain lacks a primary signaling domain, such as CD3z or other primary signaling domains detailed elsewhere herein. A costimulatory-only CAR comprises an extracellular domain, a transmembrane domain and a cytoplasmic domain. The cytoplasmic domain comprises a costimulatory molecule, such as those described elsewhere herein. In one embodiment, the costimulatory molecule is selected from the group consisting of CD28 and 4-1BB (CD137). A costimulatory-only CAR cell is independent of a CAR comprising a primary signaling domain, such as CD3z or those described elsewhere herein. In one embodiment, a costimulatory-only CAR can be used to enhance endogenous T cell activation.

A costimulatory-only CAR can function in T cell in combination with any signal playing a role in T cell effector function, including, but not limited to, signals from an endogenous TCR, and exogenous TCR provided by gene transfer, and a first generation CD3z-only CAR, the like. In one embodiment, the costimulatory-only CAR comprises a CD28 costimulatory signaling region. In one embodiment, the costimulatory-only CAR comprises a 4-1BB costimulatory signaling region.

In one embodiment, the costimulatory-only CAR is not capable of inducing substantial T cell activation upon binding of its target antigen. For example, recognition of aFR alone and singular transmission of CD28 signal, in the absence of mesothelin-directed CD3z-signals, does not activate trans-signaling CAR T cells. Instead, the costimulatory CAR is enhancing the signal induced by a CAR comprising a signaling domain derived from CD3z or those described elsewhere herein.

In one embodiment, the costimulatory-only CAR can be used in a method of using a plurality of different CARs to enhance tumor specificity. For example, in one embodiment, the activation of a T cell comprising a first CAR comprising a primary signaling domain and a second CAR comprising a costimulatory domain requires binding to a tumor cell which expresses each antigens specific to each CAR. T cell activation would be limited against cells bearing only a single antigen, thereby permitting the T cell response to be selective for the tumor cell. In one embodiment, a costimulatory-only CAR can increase the resistance of CAR T cells to antigen-induced cell death (AICD). In one embodiment, a costimulatory-only CAR can provide sustained survival and activation against normal host tissues expressing low levels of TAA.

In one embodiment, a costimulatory-only CAR provides antigen-triggered costimulation to antigen-specific T cells where recognition/TCR signaling occurs via an independent receptor. In one embodiment, the independent receptor is a first generation CD3z-only CAR. In one embodiment, the independent receptor is an endogenous TCR. In one embodiment, the independent receptor is an exogenous transferred TCR. In one embodiment, the costimulatory-only CAR comprises the nucleic acid sequence of one of SEQ ID NO: 6, SEQ ID NO: 8, or SEQ ID NO: 10. In one embodiment, the costimulatory-only CAR comprises the nucleic acid sequence that encodes the amino acid sequence of one of SEQ ID NO: 5, SEQ ID NO: 7, or SEQ ID NO: 9. In another embodiment, the costimulatory-only CAR comprises the amino acid sequence of one of SEQ ID NO: 5, SEQ ID NO: 7, or SEQ ID NO: 9.

RNA Transfection

In one embodiment, the genetically modified T cells of the invention are modified through the introduction of RNA. In one embodiment, an in vitro transcribed RNA CAR can be introduced to a cell as a form of transient transfection. In another embodiment, the RNA CAR is introduced along with an in vitro transcribed RNA encoding a bispecific antibody. The RNA is produced by in vitro transcription using a polymerase chain reaction (PCR)-generated template. DNA of interest from any source can be directly converted by PCR into a template for in vitro mRNA synthesis using appropriate primers and RNA polymerase. The source of the DNA can be, for example, genomic DNA, plasmid DNA, phage DNA, cDNA, synthetic DNA sequence or any other appropriate source of DNA. The desired template for in vitro transcription is the CAR of the present invention. In one embodiment, the template for the RNA CAR comprises an extracellular domain comprising a single chain variable domain of an anti-tumor antibody; a transmembrane domain comprising the hinge and transmembrane domain of CD8a; and a cytoplasmic domain. By way of another example, the template comprises a plurality of types of CARs.

In one embodiment, the DNA to be used for PCR contains an open reading frame. The DNA can be from a naturally occurring DNA sequence from the genome of an organism. In one embodiment, the DNA is a full length gene of interest of a portion of a gene. The gene can include some or all of the 5' and/or 3' untranslated regions (UTRs). The gene can include exons and introns. In one embodiment, the DNA to be used for PCR is a human gene. In another embodiment, the DNA to be used for PCR is a human gene including the 5' and 3' UTRs. The DNA can alternatively be an artificial DNA sequence that is not normally expressed in a naturally occurring organism. An exemplary artificial DNA sequence is one that contains portions of genes that are ligated together to form an open reading frame that encodes a fusion protein. The portions of DNA that are ligated together can be from a single organism or from plurality organism.

Genes that can be used as sources of DNA for PCR include genes that encode polypeptides that provide a therapeutic or prophylactic effect to an organism or that can be used to diagnose a disease or disorder in an organism. Preferred genes are genes which are useful for a short term treatment, or where there are safety concerns regarding dosage or the expressed gene. For example, for treatment of cancer, autoimmune disorders, parasitic, viral, bacterial, fungal or other infections, the transgene(s) to be expressed may encode a polypeptide that functions as a ligand or receptor for cells of the immune system, or can function to stimulate or inhibit the immune system of an organism. In some embodiments, it is not desirable to have prolonged ongoing stimulation of the immune system, nor necessary to produce changes which last after successful treatment, since this may then elicit a new problem. For treatment of an autoimmune disorder, it may be desirable to inhibit or suppress the immune system during a flare-up, but not long term, which could result in the patient becoming overly sensitive to an infection.

PCR is used to generate a template for in vitro transcription of mRNA which is used for transfection. Methods for performing PCR are well known in the art. Primers for use in PCR are designed to have regions that are substantially complementary to regions of the DNA to be used as a template for the PCR. "Substantially complementary", as used herein, refers to sequences of nucleotides where a majority or all of the bases in the primer sequence are complementary, or one or more bases are non-complementary, or mismatched. Substantially complementary sequences are able to anneal or hybridize with the intended DNA target under annealing conditions used for PCR. The primers can be designed to be substantially complementary to any portion of the DNA template. For example, the primers can be designed to amplify the portion of a gene that is normally transcribed in cells (the open reading frame), including 5' and 3' UTRs. The primers can also be designed to amplify a portion of a gene that encodes a particular domain of interest. In one embodiment, the primers are designed to amplify the coding region of a human cDNA, including all or portions of the 5' and 3' UTRs. Primers useful for PCR are generated by synthetic methods that are well known in the art. "Forward primers" are primers that contain a region of nucleotides that are substantially complementary to nucleotides on the DNA template that are upstream of the DNA sequence that is to be amplified. "Upstream" is used herein to refer to a location 5, to the DNA sequence to be amplified relative to the coding strand. "Reverse primers" are primers that contain a region of nucleotides that are substantially complementary to a double-stranded DNA template that are downstream of the DNA sequence that is to be amplified. "Downstream" is used herein to refer to a location 3' to the DNA sequence to be amplified relative to the coding strand.

Any DNA polymerase useful for PCR can be used in the methods disclosed herein. The reagents and polymerase are commercially available from a number of sources.

Chemical structures with the ability to promote stability and/or translation efficiency may also be used. The RNA preferably has 5' and 3' UTRs. In one embodiment, the 5' UTR is between zero and 3000 nucleotides in length. The length of 5' and 3' UTR sequences to be added to the coding region can be altered by different methods, including, but not limited to, designing primers for PCR that anneal to different regions of the UTRs. Using this approach, one of ordinary skill in the art can modify the 5' and 3' UTR lengths required to achieve optimal translation efficiency following transfection of the transcribed RNA.

The 5' and 3' UTRs can be the naturally occurring, endogenous 5' and 3' UTRs for the gene of interest. Alternatively, UTR sequences that are not endogenous to the gene of interest can be added by incorporating the UTR sequences into the forward and reverse primers or by any other modifications of the template. The use of UTR sequences that are not endogenous to the gene of interest can be useful for modifying the stability and/or translation efficiency of the RNA. For example, it is known that AU-rich elements in 3' UTR sequences can decrease the stability of mRNA. Therefore, 3' UTRs can be selected or designed to increase the stability of the transcribed RNA based on properties of UTRs that are well known in the art.

In one embodiment, the 5' UTR can contain the Kozak sequence of the endogenous gene. Alternatively, when a 5' UTR that is not endogenous to the gene of interest is being added by PCR as described above, a consensus Kozak sequence can be redesigned by adding the 5' UTR sequence. Kozak sequences can increase the efficiency of translation of some RNA transcripts, but does not appear to be required for all RNAs to enable efficient translation. The requirement for Kozak sequences for many mRNAs is known in the art. In other embodiments the 5' UTR can be derived from an RNA virus whose RNA genome is stable in cells. In other embodiments various nucleotide analogues can be used in the 3' or 5' UTR to impede exonuclease degradation of the mRNA.

To enable synthesis of RNA from a DNA template without the need for gene cloning, a promoter of transcription should be attached to the DNA template upstream of the sequence to be transcribed. When a sequence that functions as a promoter for an RNA polymerase is added to the 5' end of the forward primer, the RNA polymerase promoter becomes incorporated into the PCR product upstream of the open reading frame that is to be transcribed. In one preferred embodiment, the promoter is a T7 polymerase promoter, as described elsewhere herein. Other useful promoters include, but are not limited to, T3 and SP6 RNA polymerase promoters. Consensus nucleotide sequences for T7, T3 and SP6 promoters are known in the art.

In a preferred embodiment, the mRNA has both a cap on the 5' end and a 3' poly(A) tail which determine ribosome binding, initiation of translation and stability mRNA in the cell. On a circular DNA template, for instance, plasmid DNA, RNA polymerase produces a long concatameric product which is not suitable for expression in eukaryotic cells. The transcription of plasmid DNA linearized at the end of the 3' UTR results in normal sized mRNA which is not effective in eukaryotic transfection even if it is polyadenylated after transcription.

On a linear DNA template, phage T7 RNA polymerase can extend the 3' end of the transcript beyond the last base of the template (Schenborn and Mierendorf, Nuc Acids Res., 13:6223-36 (1985); Nacheva and Berzal-Herranz, Eur. J. Biochem., 270:1485-65 (2003).

The conventional method of integration of polyA/T stretches into a DNA template is molecular cloning. However polyA/T sequence integrated into plasmid DNA can cause plasmid instability, which is why plasmid DNA templates obtained from bacterial cells are often highly contaminated with deletions and other aberrations. This makes cloning procedures not only laborious and time consuming but often not reliable. That is why a method which allows construction of DNA templates with polyA/T 3' stretch without cloning highly desirable.

The polyA/T segment of the transcriptional DNA template can be produced during PCR by using a reverse primer containing a polyT tail, such as 100T tail (size can be 50-5000 T), or after PCR by any other method, including, but not limited to, DNA ligation or in vitro recombination. Poly(A) tails also provide stability to RNAs and reduce their degradation. Generally, the length of a poly(A) tail positively correlates with the stability of the transcribed RNA. In one embodiment, the poly(A) tail is between 100 and 5000 adenosines.

Poly(A) tails of RNAs can be further extended following in vitro transcription with the use of a poly(A) polymerase, such as E. coli polyA polymerase (E-PAP). In one embodiment, increasing the length of a poly(A) tail from 100 nucleotides to between 300 and 400 nucleotides results in about a two-fold increase in the translation efficiency of the RNA. Additionally, the attachment of different chemical groups to the 3' end can increase mRNA stability. Such attachment can contain modified/artificial nucleotides, aptamers and other compounds. For example, ATP analogs can be incorporated into the poly(A) tail using poly(A) polymerase. ATP analogs can further increase the stability of the RNA.

5' caps on also provide stability to RNA molecules. In a preferred embodiment, RNAs produced by the methods disclosed herein include a 5' cap. The 5' cap is provided using techniques known in the art and described herein (Cougot, et al., Trends in Biochem. Sci., 29:436-444 (2001); Stepinski, et al., RNA, 7:1468-95 (2001); Elango, et al., Biochim. Biophys. Res. Commun., 330:958-966 (2005)).

The RNAs produced by the methods disclosed herein can also contain an internal ribosome entry site (IRES) sequence. The IRES sequence may be any viral, chromosomal or artificially designed sequence which initiates cap-independent ribosome binding to mRNA and facilitates the initiation of translation. Any solutes suitable for cell electroporation, which can contain factors facilitating cellular permeability and viability such as sugars, peptides, lipids, proteins, antioxidants, and surfactants can be included.

RNA can be introduced into target cells using any of a number of different methods, for instance, commercially available methods which include, but are not limited to, electroporation (Amaxa Nucleofector-II (Amaxa Biosystems, Cologne, Germany)), (ECM 830 (BTX) (Harvard Instruments, Boston, Mass.) or the Gene Pulser II (BioRad, Denver, Colo.), Multiporator (Eppendort, Hamburg Germany), cationic liposorne mediated transfection using lipofection, polymer encapsulation, peptide mediated transfection, or biolistic particle delivery systems such as "gene guns" (see, for example, Nishikawa, et al. Hum Gene Ther., 12(8):861-70 (2001).

Genetically Modified T Cells

In some embodiments, the CAR sequences are delivered into cells using a retroviral or lentiviral vector. CAR-expressing retroviral and lentiviral vectors can be delivered into different types of eukaryotic cells as well as into tissues and whole organisms using transduced cells as carriers or cell-free local or systemic delivery of encapsulated, bound or naked vectors. The method used can be for any purpose where stable expression is required or sufficient.

In other embodiments, the CAR sequences are delivered into cells using in vitro transcribed mRNA. In vitro transcribed mRNA CAR can be delivered into different types of eukaryotic cells as well as into tissues and whole organisms using transfected cells as carriers or cell-free local or systemic delivery of encapsulated, bound or naked mRNA. The method used can be for any purpose where transient expression is required or sufficient.

In one embodiment, the genetically modified cells express one or more types of CARs, where the nucleic acid sequence of each type of CAR is set forth in SEQ ID NO: 4, SEQ ID NO: 6, SEQ ID NO: 8, and SEQ ID NO: 10. In one embodiment, the genetically modified cells express one or more types of CARs, where the nucleic acid sequence of the types of CARs encode the amino acid sequences set forth in SEQ ID NO: 3, SEQ ID NO: 5, SEQ ID NO: 7, and SEQ ID NO: 9. In another embodiment, the genetically modified cells express one or more types of CARs, where the amino acid sequence of the types of CARs is set forth in SEQ ID NO: 3, SEQ ID NO: 5, SEQ ID NO: 7, and SEQ ID NO: 9.

The disclosed methods can be applied to the modulation of T cell activity in basic research and therapy, in the fields of cancer, stem cells, acute and chronic infections, and autoimmune diseases, including the assessment of the ability of the genetically modified T cell to kill a target cancer cell.

The methods also provide the ability to control the level of expression over a wide range by changing, for example, the promoter or the amount of input RNA, making it possible to individually regulate the expression level. Furthermore, the PCR-based technique of mRNA production greatly facilitates the design of the chimeric receptor mRNAs with different structures and combination of their domains. For example, varying of different intracellular effector/costimulator domains on multiple chimeric receptors in the same cell allows determination of the structure of the receptor combinations which assess the highest level of cytotoxicity against multi-antigenic targets, and at the same time lowest cytotoxicity toward normal cells.

One advantage of RNA transfection methods of the invention is that RNA transfection is essentially transient and a vector-free: An RNA transgene can be delivered to a lymphocyte and expressed therein following a brief in vitro cell activation, as a minimal expressing cassette without the need for any additional viral sequences. Under these conditions, integration of the transgene into the host cell genome is unlikely. Cloning of cells is not necessary because of the efficiency of transfection of the RNA and its ability to uniformly modify the entire lymphocyte population.

Genetic modification of T cells with in vitro-transcribed RNA (IVT-RNA) makes use of two different strategies both of which have been successively tested in various animal models. Cells are transfected with in vitro-transcribed RNA by means of lipofection or electroporation. Preferably, it is desirable to stabilize IVT-RNA using various modifications in order to achieve prolonged expression of transferred IVT-RNA.

Some IVT vectors are known in the literature which are utilized in a standardized manner as template for in vitro transcription and which have been genetically modified in such a way that stabilized RNA transcripts are produced. Currently protocols used in the art are based on a plasmid vector with the following structure: a 5' RNA polymerase promoter enabling RNA transcription, followed by a gene of interest which is flanked either 3' and/or 5' by untranslated regions (UTR), and a 3' polyadenyl cassette containing 50-70 A nucleotides. Prior to in vitro transcription, the circular plasmid is linearized downstream of the polyadenyl cassette by type II restriction enzymes (recognition sequence corresponds to cleavage site). The polyadenyl cassette thus corresponds to the later poly(A) sequence in the transcript. As a result of this procedure, some nucleotides remain as part of the enzyme cleavage site after linearization and extend or mask the poly(A) sequence at the 3' end. It is not clear, whether this nonphysiological overhang affects the amount of protein produced intracellularly from such a construct.

RNA has several advantages over more traditional plasmid or viral approaches. Gene expression from an RNA source does not require transcription and the protein product is produced rapidly after the transfection. Further, since the RNA has to only gain access to the cytoplasm, rather than the nucleus, and therefore typical transfection methods result in an extremely high rate of transfection. In addition, plasmid based approaches require that the promoter driving the expression of the gene of interest be active in the cells under study.

In another aspect, the RNA construct can be delivered into the cells by electroporation. See, e.g., the formulations and methodology of electroporation of nucleic acid constructs into mammalian cells as taught in US 2004/0014645, US 2005/0052630A1, US 2005/0070841A1, US 2004/0059285A1, US 2004/0092907A1. The various parameters including electric field strength required for electroporation of any known cell type are generally known in the relevant research literature as well as numerous patents and applications in the field. See e.g., U.S. Pat. Nos. 6,678,556, 7,171,264, and 7,173,116. Apparatus for therapeutic application of electroporation are available commercially, e.g., the MedPulser™ DNA Electroporation Therapy System (Inovio/Genetronics, San Diego, Calif.), and are described in patents such as U.S. Pat. Nos. 6,567,694; 6,516,223, 5,993,434, 6,181,964, 6,241,701, and 6,233,482; electroporation may also be used for transfection of cells in vitro as described e.g. in US20070128708A1. Electroporation may also be utilized to deliver nucleic acids into cells in vitro. Accordingly, electroporation-mediated administration into cells of nucleic acids including expression constructs utilizing any of the many available devices and electroporation systems known to those of skill in the art presents an exciting new means for delivering an RNA of interest to a target cell.

Activation and Expansion of T Cells

Whether prior to or after genetic modification of the T cells to express a desirable CAR, the T cells can be activated and expanded generally using methods as described, for example, in U.S. Pat. Nos. 6,352,694; 6,534,055; 6,905,680; 6,692,964; 5,858,358; 6,887,466; 6,905,681; 7,144,575; 7,067,318; 7,172,869; 7,232,566; 7,175,843; 5,883,223; 6,905,874; 6,797,514; 6,867,041; and U.S. Patent Application Publication No. 20060121005.

Generally, the T cells of the invention are expanded by contact with a surface having attached thereto an agent that stimulates a CD3/TCR complex associated signal and a ligand that stimulates a co-stimulatory molecule on the surface of the T cells. In particular, T cell populations may be stimulated as described herein, such as by contact with an anti-CD3 antibody, or antigen-binding fragment thereof, or an anti-CD2 antibody immobilized on a surface, or by contact with a protein kinase C activator (e.g., bryostatin) in conjunction with a calcium ionophore. For co-stimulation of an accessory molecule on the surface of the T cells, a ligand that binds the accessory molecule is used. For example, a population of T cells can be contacted with an anti-CD3 antibody and an anti-CD28 antibody, under conditions appropriate for stimulating proliferation of the T cells. To stimulate proliferation of either $CD4^+$ T cells or $CD8^+$ T cells, an anti-CD3 antibody and an anti-CD28 antibody. Examples of an anti-CD28 antibody include 9.3, B-T3, XR-CD28 (Diaclone, Besancon, France) can be used as can other methods commonly known in the art (Berg et al., Transplant Proc. 30(8):3975-3977, 1998; Haanen et al., J. Exp. Med. 190(9):13191328, 1999; Garland et al., J. Immunol Meth. 227(1-2):53-63, 1999).

In certain embodiments, the primary stimulatory signal and the co-stimulatory signal for the T cell may be provided by different protocols. For example, the agents providing each signal may be in solution or coupled to a surface. When coupled to a surface, the agents may be coupled to the same surface (i.e., in "cis" formation) or to separate surfaces (i.e., in "trans" formation). Alternatively, one agent may be coupled to a surface and the other agent in solution. In one embodiment, the agent providing the co-stimulatory signal is bound to a cell surface and the agent providing the primary activation signal is in solution or coupled to a surface. In certain embodiments, both agents can be in solution. In another embodiment, the agents may be in soluble form, and then cross-linked to a surface, such as a cell expressing Fc receptors or an antibody or other binding agent which will bind to the agents. In this regard, see for example, U.S. Patent Application Publication Nos. 20040101519 and 20060034810 for artificial antigen presenting cells (aAPCs) that are contemplated for use in activating and expanding T cells in the present invention.

In one embodiment, the two agents are immobilized on beads, either on the same bead, i.e., "cis," or to separate beads, i.e., "trans." By way of example, the agent providing the primary activation signal is an anti-CD3 antibody or an antigen-binding fragment thereof and the agent providing the co-stimulatory signal is an anti-CD28 antibody or antigen-binding fragment thereof; and both agents are co-immobilized to the same bead in equivalent molecular amounts. In one embodiment, a 1:1 ratio of each antibody bound to the beads for $CD4^+$ T cell expansion and T cell growth is used. In certain aspects of the present invention, a ratio of anti CD3:CD28 antibodies bound to the beads is used such that an increase in T cell expansion is observed as compared to the expansion observed using a ratio of 1:1. In one particular embodiment an increase of from about 1 to about 3 fold is observed as compared to the expansion observed using a ratio of 1:1. In one embodiment, the ratio of CD3:CD28 antibody bound to the beads ranges from 100:1 to 1:100 and all integer values there between. In one aspect of the present invention, more anti-CD28 antibody is bound to the particles than anti-CD3 antibody, i.e., the ratio of CD3:CD28 is less than one. In certain embodiments of the invention, the ratio of anti CD28 antibody to anti CD3 antibody bound to the beads is greater than 2:1. In one particular embodiment, a 1:100 CD3:CD28 ratio of antibody bound to beads is used. In another embodiment, a 1:75 CD3:CD28 ratio of antibody bound to beads is used. In a further embodiment, a 1:50 CD3:CD28 ratio of antibody bound to beads is used. In another embodiment, a 1:30 CD3:CD28 ratio of antibody bound to beads is used. In one preferred embodiment, a 1:10 CD3:CD28 ratio of antibody bound to beads is used. In another embodiment, a 1:3 CD3:CD28 ratio of antibody bound to the beads is used. In yet another embodiment, a 3:1 CD3:CD28 ratio of antibody bound to the beads is used.

Ratios of particles to cells from 1:500 to 500:1 and any integer values in between may be used to stimulate T cells or other target cells. As those of ordinary skill in the art can readily appreciate, the ratio of particles to cells may depend on particle size relative to the target cell. For example, small sized beads could only bind a few cells, while larger beads could bind many. In certain embodiments the ratio of cells to particles ranges from 1:100 to 100:1 and any integer values in-between and in further embodiments the ratio comprises 1:9 to 9:1 and any integer values in between, can also be used to stimulate T cells. The ratio of anti-CD3- and anti-CD28-coupled particles to T cells that result in T cell stimulation can vary as noted above, however certain preferred values include 1:100, 1:50, 1:40, 1:30, 1:20, 1:10, 1:9, 1:8, 1:7, 1:6, 1:5, 1:4, 1:3, 1:2, 1:1, 2:1, 3:1, 4:1, 5:1, 6:1, 7:1, 8:1, 9:1, 10:1, and 15:1 with one preferred ratio being at least 1:1 particles per T cell. In one embodiment, a ratio of particles to cells of 1:1 or less is used. In one particular embodiment, a preferred particle: cell ratio is 1:5. In further embodiments, the ratio of particles to cells can be varied depending on the day of stimulation. For example, in one embodiment, the ratio of particles to cells is from 1:1 to 10:1 on the first day and additional particles are added to the cells every day or every other day thereafter for up to 10 days, at final ratios of from 1:1 to 1:10 (based on cell counts on the day of addition). In one particular embodiment, the ratio of particles to cells is 1:1 on the first day of stimulation and adjusted to 1:5 on the third and fifth days of stimulation. In another embodiment, particles are added on a daily or every other day basis to a final ratio of 1:1 on the first day, and 1:5 on the third and fifth days of stimulation. In another embodiment, the ratio of particles to cells is 2:1 on the first day of stimulation and adjusted to 1:10 on the third and fifth days of stimulation. In another embodiment, particles are added on a daily or every other day basis to a final ratio of 1:1 on the first day, and 1:10 on the third and fifth days of stimulation. One of skill in the art will appreciate that a variety of other ratios may be suitable for use in the present invention. In particular, ratios will vary depending on particle size and on cell size and type.

In further embodiments of the present invention, the cells, such as T cells, are combined with agent-coated beads, the beads and the cells are subsequently separated, and then the cells are cultured. In an alternative embodiment, prior to culture, the agent-coated beads and cells are not separated but are cultured together. In a further embodiment, the beads and cells are first concentrated by application of a force, such as a magnetic force, resulting in increased ligation of cell surface markers, thereby inducing cell stimulation.

By way of example, cell surface proteins may be ligated by allowing paramagnetic beads to which anti-CD3 and anti-CD28 are attached (3×28 beads) to contact the T cells. In one embodiment the cells (for example, $10^4$ to $10^9$ T cells) and beads (for example, DYNABEADS® M-450 CD3/CD28 T paramagnetic beads at a ratio of 1:1) are combined in a buffer, preferably PBS (without divalent cations such as, calcium and magnesium). Again, those of ordinary skill in the art can readily appreciate any cell concentration may be used. For example, the target cell may be very rare in the sample and comprise only 0.01% of the sample or the entire sample (i.e., 100%) may comprise the target cell of interest. Accordingly, any cell number is within the context of the present invention. In certain embodiments, it may be desirable to significantly decrease the volume in which particles and cells are mixed together (i.e., increase the concentration of cells), to ensure maximum contact of cells and particles. For example, in one embodiment, a concentration of about 2 billion cells/ml is used. In another embodiment, greater than 100 million cells/ml is used. In a further embodiment, a concentration of cells of 10, 15, 20, 25, 30, 35, 40, 45, or 50 million cells/ml is used. In yet another embodiment, a concentration of cells from 75, 80, 85, 90, 95, or 100 million cells/ml is used. In further embodiments, concentrations of 125 or 150 million cells/ml can be used. Using high concentrations can result in increased cell yield, cell activation, and cell expansion. Further, use of high cell concentrations allows more efficient capture of cells that may weakly express target antigens of interest, such as CD28-negative T cells. Such populations of cells may have therapeutic value and would be desirable to obtain in certain embodiments. For example, using high concentration of cells allows more efficient selection of CD8+ T cells that normally have weaker CD28 expression.

In one embodiment of the present invention, the mixture may be cultured for several hours (about 3 hours) to about 14 days or any hourly integer value in between. In another embodiment, the mixture may be cultured for 21 days. In one embodiment of the invention the beads and the T cells are cultured together for about eight days. In another embodiment, the beads and T cells are cultured together for 2-3 days. Several cycles of stimulation may also be desired such that culture time of T cells can be 60 days or more. Conditions appropriate for T cell culture include an appropriate media (e.g., Minimal Essential Media or RPMI Media 1640 or, X-vivo 15, (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-15, TGFβ, and TNF-α or any other additives for the growth of cells known to the skilled artisan. Other additives for the growth of cells include, but are not limited to, surfactant, plasmanate, and reducing agents such as N-acetyl-cysteine and 2-mercaptoethanol. Media can include RPMI 1640, AIM-V, DMEM, MEM, α-MEM, F-12, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells. Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37° C.) and atmosphere (e.g., air plus 5% $CO_2$).

T cells that have been exposed to varied stimulation times may exhibit different characteristics. For example, typical blood or apheresed peripheral blood mononuclear cell products have a helper T cell population ($T_H$, CD4+) that is greater than the cytotoxic or suppressor T cell population ($T_C$, CD8+). Ex vivo expansion of T cells by stimulating CD3 and CD28 receptors produces a population of T cells that prior to about days 8-9 consists predominately of $T_H$ cells, while after about days 8-9, the population of T cells comprises an increasingly greater population of $T_C$ cells. Accordingly, depending on the purpose of treatment, infusing a subject with a T cell population comprising predominately of $T_H$ cells may be advantageous. Similarly, if an antigen-specific subset of $T_C$ cells has been isolated it may be beneficial to expand this subset to a greater degree.

Further, in addition to CD4 and CD8 markers, other phenotypic markers vary significantly, but in large part, reproducibly during the course of the cell expansion process. Thus, such reproducibility enables the ability to tailor an activated T cell product for specific purposes.

Therapeutic Application

The present invention encompasses a cell (e.g., T cell) modified to express a plurality of types of CARs, wherein each CAR combines an antigen recognition domain of a specific antibody with an intracellular domain. In one embodiment, at least one of the plurality of types of CARs comprises a primary signaling domain, such as CD3z or other primary signaling domains detailed elsewhere herein. In one embodiment, at least one of the plurality of types of CARs comprises a costimulatory domain. In one embodiment, the modified T cell expresses a plurality of types of CARs that function as trans-signaling CARs, where T cell activation is dependent upon binding of more than one type of CAR to its targeted antigen. Therefore, in some instances, the modified T cell can elicit a CAR-mediated T-cell response. In one embodiment, the dependence of the binding to more than one type of antigen allows the modified T cell to exhibit a heightened specificity to elicit a response upon binding of a tumor cell rather than a normal bystander cell.

The invention encompasses a cell (e.g., T cell) modified to express costimulatory-only CARs, wherein each CAR combines an antigen recognition domain of a specific antibody with an intracellular domain of for example, CD28, 4-1BB (CD137), or any combination thereof. Therefore, in some instances, the modified T cell can enhance endogenous T cell activation.

The invention provides the use of a plurality of types of trans-signaling CARs to redirect the specificity of a primary T cell to a tumor antigen. Thus, the present invention also provides a method for stimulating a T cell-mediated immune response to a target cell population or tissue in a mammal comprising the step of administering to the mammal a T cell that expresses a plurality of types of trans-signaling CARs, wherein each type of CAR comprises a binding moiety that specifically interacts with a predetermined target. In one embodiment, the cell comprises a first CAR comprising a zeta chain portion comprising for example the intracellular domain of human CD3z, and a second CAR comprising a costimulatory signaling region.

In one embodiment, the trans-signaling CAR T cells of the invention can undergo robust in vivo T cell expansion and can persist for an extended amount of time. In another embodiment, the CAR T cells of the invention evolve into specific memory T cells that can be reactivated to inhibit any additional tumor formation or growth. For example, CAR T cells of the invention can undergo robust in vivo T cell expansion and persist at high levels for an extended amount of time in blood and bone marrow and form specific memory T cells. Without wishing to be bound by any particular theory, CAR T cells may differentiate in vivo into a central memory-like state upon encounter and subsequent elimination of target cells expressing the surrogate antigen.

Without wishing to be bound by any particular theory, the anti-tumor immunity response elicited by the trans-signaling CAR-modified T cells may be an active or a passive immune response. In addition, the trans-signaling CAR mediated immune response may be part of an adoptive immunotherapy approach in which CAR-modified T cells induce an immune response specific to the antigen binding domain in the CAR.

In one embodiment, the present invention includes a type of cellular therapy where T cells are genetically modified to express a costimulatory-only CAR and the T cell is infused to a recipient in need thereof. The infused cell is able to kill tumor cells in the recipient. Unlike antibody therapies, modified T cells are able to replicate in vivo resulting in long-term persistence that can lead to sustained tumor control. In one embodiment, the costimulatory-only CAR functions with an independent receptor to elicit a T cell response. For example, the independent receptor can include a CD3z-containing first generation CAR, an endogenous T cell receptor, or exogenous T cell receptor.

While the data disclosed herein specifically disclose trans-signaling CAR T cells expressing a first CAR comprising an anti-mesothelin scFv and CD3z and second CAR comprising an anti-FRa scFv and CD28, the invention should be construed to include any number of variations for each of the components of the construct as described elsewhere herein. That is, the invention includes the use of any antigen binding domains in the CARs to generate a CAR-mediated T-cell response specific to the antigen binding domain. For example, the antigen binding domain in the CAR of the invention can target a tumor antigen for the purposes of treat cancer.

Cancers that may be treated include tumors that are not vascularized, or not yet substantially vascularized, as well as vascularized tumors. The cancers may comprise non-solid tumors (such as hematological tumors, for example, leukemias and lymphomas) or may comprise solid tumors. Types of cancers to be treated with the CARs of the invention include, but are not limited to, carcinoma, blastoma, and sarcoma, and certain leukemia or lymphoid malignancies, benign and malignant tumors, and malignancies e.g., sarcomas, carcinomas, and melanomas. Adult tumors/cancers and pediatric tumors/cancers are also included.

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

Solid tumors are abnormal masses of tissue that usually do not contain cysts or liquid areas. Solid tumors can be benign or malignant. Different types of solid tumors are named for the type of cells that form them (such as sarcomas, carcinomas, and lymphomas). Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

In one embodiment, the antigen bind moiety portion of the trans-signaling CAR T cells of the invention is designed to treat a particular cancer. In one embodiment, the trans-signaling CAR T cells of the invention are modified to express a first CAR targeting a first antigen and a second CAR targeting a second antigen, where the first and second antigen are expressed on a particular tumor or cancer. For example, the trans-signaling CAR T cells modified to target mesothelin and folate can be used to treat cancers and disorders including ovarian cancer. In another embodiment, the trans-signaling CAR T cells are modified to target EGFRvIII and IL-13Ra to treat glioma. In another embodiment, the trans-signaling CAR T cells are modified to target EGFR and CA-IX to treat renal cell carcinoma (RCC). In another embodiment, the trans-signaling CAR T cells are modified to target MUC1 and EGFR to treat pancreatic cancer. In another embodiment, the trans-signaling CAR T cells are modified to target mesothelin and HER2 to treat breast cancer.

In another embodiment, a CAR of the invention can be designed to target CD22 to treat diffuse large B-cell lymphoma.

In one embodiment, cancers and disorders include but are not limited to pre-B ALL (pediatric indication), adult ALL, mantle cell lymphoma, diffuse large B-cell lymphoma, salvage post allogenic bone marrow transplantation, and the like can be treated using a combination of CARs that target CD19, CD20, CD22, and ROR1.

In one embodiment, a CAR of the invention can be designed to target mesothelin to treat mesothelioma, pancreatic cancer, ovarian cancer, and the like. In another embodiment, a CAR of the invention can be designed to target CD33/IL3Ra to treat acute myelogenous leukemia and the like. In a further embodiment, a CAR of the invention can be designed to target c-Met to treat triple negative breast cancer, non-small cell lung cancer, and the like.

In one embodiment, a CAR of the invention can be designed to target PSMA to treat prostate cancer and the like. In another embodiment, a CAR of the invention can be designed to target Glycolipid F77 to treat prostate cancer and the like. In a further embodiment, a CAR of the invention can be designed to target EGFRvIII to treat glioblastoma and the like.

In one embodiment, a CAR of the invention can be designed to target GD-2 to treat neuroblastoma, melanoma, and the like. In another embodiment, a CAR of the invention can be designed to target NY-ESO-1 TCR to treat myeloma, sarcoma, melanoma, and the like. In a further embodiment, a CAR of the invention can be designed to target MAGE A3 TCR to treat myeloma, sarcoma, melanoma, and the like.

However, the invention should not be construed to be limited to solely to the antigen targets and diseases disclosed herein. Rather, the invention should be construed to include any antigenic target that is associated with a disease where a CAR can be used to treat the disease.

The CAR-modified T cells of the invention may also serve as a type of vaccine for ex vivo immunization and/or in vivo therapy in a mammal. Preferably, the mammal is a human.

With respect to ex vivo immunization, at least one of the following occurs in vitro prior to administering the cell into a mammal: i) expansion of the cells, ii) introducing a nucleic acid encoding a CAR to the cells, and/or iii) cryopreservation of the cells.

Ex vivo procedures are well known in the art and are discussed more fully below. Briefly, cells are isolated from a mammal (preferably a human) and genetically modified (i.e., transduced or transfected in vitro) with a vector expressing a CAR disclosed herein. The CAR-modified cell can be administered to a mammalian recipient to provide a therapeutic benefit. The mammalian recipient may be a human and the CAR-modified cell can be autologous with respect to the recipient. Alternatively, the cells can be allogeneic, syngeneic or xenogeneic with respect to the recipient.

The procedure for ex vivo expansion of hematopoietic stem and progenitor cells is described in U.S. Pat. No. 5,199,942, incorporated herein by reference, can be applied to the cells of the present invention. Other suitable methods are known in the art, therefore the present invention is not limited to any particular method of ex vivo expansion of the cells. Briefly, ex vivo culture and expansion of T cells comprises: (1) collecting CD34+ hematopoietic stem and progenitor cells from a mammal from peripheral blood harvest or bone marrow explants; and (2) expanding such cells ex vivo. In addition to the cellular growth factors described in U.S. Pat. No. 5,199,942, other factors such as flt3-L, IL-1, IL-3 and c-kit ligand, can be used for culturing and expansion of the cells.

In addition to using a cell-based vaccine in terms of ex vivo immunization, the present invention also provides compositions and methods for in vivo immunization to elicit an immune response directed against an antigen in a patient.

Generally, the cells activated and expanded as described herein may be utilized in the treatment and prevention of diseases that arise in individuals who are immunocompromised. In particular, the CAR-modified T cells of the invention are used in the treatment of cancer. In certain embodiments, the cells of the invention are used in the treatment of patients at risk for developing cancer. Thus, the present invention provides methods for the treatment or prevention of cancer comprising administering to a subject in need thereof, a therapeutically effective amount of the CAR-modified T cells of the invention.

The CAR-modified T cells of the present invention may be administered either alone, or as a pharmaceutical composition in combination with diluents and/or with other components such as IL-2 or other cytokines or cell populations. Briefly, pharmaceutical compositions of the present invention may comprise a target cell population as described herein, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the present invention are preferably formulated for intravenous administration.

Pharmaceutical compositions of the present invention may be administered in a manner appropriate to the disease to be treated (or prevented). The quantity and frequency of administration will be determined by such factors as the condition of the patient, and the type and severity of the patient's disease, although appropriate dosages may be determined by clinical trials.

When "an immunologically effective amount", "an anti-tumor effective amount", "an tumor-inhibiting effective amount", or "therapeutic amount" is indicated, the precise amount of the compositions of the present invention to be administered can be determined by a physician with consideration of individual differences in age, weight, tumor size, extent of infection or metastasis, and condition of the patient (subject). It can generally be stated that a pharmaceutical composition comprising the T cells described herein may be administered at a dosage of $10^4$ to $10^9$ cells/kg body weight, preferably $10^5$ to $10^6$ cells/kg body weight, including all integer values within those ranges. T cell compositions may also be administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In certain embodiments, it may be desired to administer activated T cells to a subject and then subsequently redraw blood (or have an apheresis performed), activate T cells therefrom according to the present invention, and reinfuse the patient with these activated and expanded T cells. This process can be carried out multiple times every few weeks. In certain embodiments, T cells can be activated from blood draws of from 10 cc to 400 cc. In certain embodiments, T cells are activated from blood draws of 20 cc, 30 cc, 40 cc, 50 cc, 60 cc, 70 cc, 80 cc, 90 cc, or 100 cc. Not to be bound by theory, using this multiple blood draw/multiple reinfusion protocol may serve to select out certain populations of T cells.

The administration of the subject compositions may be carried out in any convenient manner, including by aerosol inhalation, injection, ingestion, transfusion, implantation or transplantation. The compositions described herein may be administered to a patient subcutaneously, intradermally, intratumorally, intranodally, intramedullary, intramuscularly, by intravenous (i.v.) injection, or intraperitoneally. In one embodiment, the T cell compositions of the present invention are administered to a patient by intradermal or subcutaneous injection. In another embodiment, the T cell compositions of the present invention are preferably administered by i. v. injection. The compositions of T cells may be injected directly into a tumor, lymph node, or site of infection.

In certain embodiments of the present invention, cells activated and expanded using the methods described herein, or other methods known in the art where T cells are expanded to therapeutic levels, are administered to a patient in conjunction with (e.g., before, simultaneously or following) any number of relevant treatment modalities, including but not limited to treatment with agents such as antiviral therapy, cidofovir and interleukin-2, Cytarabine (also known as ARA-C) or natalizumab treatment for MS patients or efalizumab treatment for psoriasis patients or other treatments for PML patients. In further embodiments, the T cells of the invention may be used in combination with chemotherapy, radiation, immunosuppressive agents, such as cyclosporin, azathioprine, methotrexate, mycophenolate, and FK506, antibodies, or other immunoablative agents such as CAM PATH, anti-CD3 antibodies or other antibody therapies, cytoxin, fludarabine, cyclosporin, FK506, rapamycin, mycophenolic acid, steroids, FR901228, cytokines, and irradiation. These drugs inhibit either the calcium dependent phosphatase calcineurin (cyclosporine and FK506) or inhibit the p70S6 kinase that is important for growth factor induced signaling (rapamycin) (Liu et al., Cell 66:807-815, 1991; Henderson et al., Immun. 73:316-321, 1991; Bierer et al., Curr. Opin. Immun. 5:763-773, 1993). In a further embodiment, the cell compositions of the present invention are administered to a patient in conjunction with (e.g., before, simultaneously or following) bone marrow transplantation, T cell ablative therapy using either chemotherapy agents such as, fludarabine, external-beam radiation therapy (XRT), cyclophosphamide, or antibodies such as OKT3 or CAM-PATH. In another embodiment, the cell compositions of the present invention are administered following B-cell ablative therapy such as agents that react with CD20, e.g., Rituxan. For example, in one embodiment, subjects may undergo standard treatment with high dose chemotherapy followed by peripheral blood stem cell transplantation. In certain embodiments, following the transplant, subjects receive an infusion of the expanded immune cells of the present invention. In an additional embodiment, expanded cells are administered before or following surgery.

The dosage of the above treatments to be administered to a patient will vary with the precise nature of the condition being treated and the recipient of the treatment. The scaling of dosages for human administration can be performed according to art-accepted practices. Strategies for CAR T cell dosing and scheduling have been discussed (Ertl et al, 2011, Cancer Res, 71:3175-81; Junghans, 2010, Journal of Translational Medicine, 8:55).

EXPERIMENTAL EXAMPLES

The invention is further described in detail by reference to the following experimental examples. These examples are provided for purposes of illustration only, and are not intended to be limiting unless otherwise specified. Thus, the invention should in no way be construed as being limited to the following examples, but rather, should be construed to encompass any and all variations which become evident as a result of the teaching provided herein.

Without further description, it is believed that one of ordinary skill in the art can, using the preceding description and the following illustrative examples, make and utilize the compounds of the present invention and practice the claimed methods. The following working examples therefore, specifically point out the preferred embodiments of the present invention, and are not to be construed as limiting in any way the remainder of the disclosure.

Example 1

Chimeric Antigen Receptor T Cells with Dissociated Signaling Domains Exhibit Focused Anti-Tumor Activity In Vivo By way of example, a trans-signaling CAR strategy was utilized to specify T cells for robust effector function that is selective for tumor but not normal tissue, whereby the T cell activation signal 1 (e.g., CD3z module) is physically dissociated from the costimulatory signal 2 (e.g., CD28 module) in two CARs of differing antigen specificity; one against mesothelin and one against □-folate receptor (aFR).

For example, human T cells were genetically modified to co-express signal 1 (Anti-Meso scFv-CD3z) and signal 2 (Anti-aFR scFv-CD28) CARs in trans. Trans-signaling CART cells showed weak cytokine secretion against tumor targets expressing only one tumor associated antigen (TAA), similar to first generation CART cells bearing CD3ζ only, but demonstrated enhanced cytokine secretion and resistance to antigen induced cell death (AICD) upon encountering natural or engineered tumor cells co-expressing mesothelin and aFR antigens, equivalent to that of second generation CART cells with dual signaling in cis. Importantly, CART cells with dual specificity showed potent anti-cancer activity, tumor localization and persistence in vivo which was superior to first generation CART cells and equivalent to second generation CARs. However, second generation CART cells also exhibited potent activity against engineered targets expressing mesothelin alone to recapitulate normal tissue, whereas trans-signaling CART cells did not. Thus, a dual specificity, trans-signaling CAR approach may potentiate the therapeutic efficacy of CART cells while minimizing activity against normal tissues.

To diminish "on target" toxicity and improve tumor-focused targeting and attack, the concept of a trans-signaling CAR strategy where the T cell activation signal 1 (CD3z module) is physically dissociated from the costimulatory signal 2 (CD28 module) was developed and tested. Since aFR and mesothelin are TAAs co-expressed in the vast majority of epithelial ovarian cancers but are expressed differentially and at low levels in normal tissues (Chang et al., 1992, Int. J. Cancer 50:373-381; Kalli et al., 2008, Gynecol. Oncol. 108:619-626; Toffoli et al., 1997, Int. J. Cancer 74:193-198; Parker et al., 2005, Anal. Biochem. 338:284-293; Mantovani et al., 1994, Eur. J. Cancer 30A (363-369)), two independent CARs of distinct specificity were utilized; a signal 1 CAR (Meso-CD3z only), and a signal 2 CAR (aFR-CD28 only) using pre-validated scFvs (Lanitis et al., 2012, Mol. Ther. 20:633-643; Song et al., 2011, Cancer Res. 71:4617-4627). In this fashion, T cells transduced to co-express both CARs can exhibit potent in vitro and in vivo effector functions that are driven by tumor encounter and coupled with diminished damage to normal tissues.

The materials and methods employed in these experiments are now described.

CAR Constructs

First and second generation anti-mesothelin M CAR constructs designated P4-z and M-28z have been previously described (Lanitis et al., 2012, Mol. Ther. 20:633-643). The anti-FRa CAR construct designated as F-28 is a derivative of a previously characterized CAR (Song et al., 2011, Cancer Res. 71:4617-4627) that encompasses the MOV-19 scFv driven by the EF1a promoter and fused only to the CD28 intracellular costimulatory signaling region via CD8a hinge and CD28 transmembrane domain. To generate the F-28 CAR construct the M-28z CAR construct was used as a template for the PCR amplification of a 350-bp fragment containing CD8a hinge-CD28TM (transmembrane domain)-CD28ICD (intracellular domain) using the following primers: 5'- ACGC GCTAGCACCACGACGCCAGCGC-3' (SEQ ID NO: 1; NheI is underlined) and 5'- ACGC GTCGACTTAGGAGCGATAGGCTGCGAAGTCGC -3' (SEQ ID NO: 2; SalI is underlined). The resulting PCR product containing a NheI site on the 5'- end and a SalI site on the 3'- end was digested with the relevant enzymes. Then the F-28z CAR construct (pELNS MOV19-28z) previously described was digested with the NheI and SalI restriction enzymes to remove the CD8hinge-CD28TM-CD28ICD-CD3z and create compatible cohesive ends followed by gel purified. Next the digested PCR product was ligated into the digested F-28z vector. The resulting product containing the anti-FRa (F) MOV19 scFv followed by CD8ahinge-CD28TM-CD28ICD was designated M-z/F-28.

Recombinant Lentivirus Production

High-titer replication-defective lentiviral vectors were produced and concentrated as previously described (Lanitis et al., 2012, Mol. Ther. 20:633-643). 293T human embryonic kidney cells were seeded at $10 \times 10^6$ per T-150 tissue culture flask 24 h before transfection. All plasmid DNA were purified using the QIAGEN Endo-free Maxi prep kit. Cells were transfected with 7 ug pVSV-G (VSV glycoprotein expression plasmid), 18 μg pRSV.REV (Rev expression plasmid), 18 μg of pMDLg/p.RRE (Gag/Pol expression plasmid), and 15 μg of pELNS transfer plasmid using Express Inn (Open Biosytems). The viral supernatant was harvested at 24 and 48 h post-transfection. Viral particles were concentrated and resuspended in 0.4 ml by ultracentrifugation for 3 h at 25,000 rpm with a Beckman SW28 rotor (Beckman Coulter, Fullerton, Calif.).

Human T Cell Transduction

Primary human T cells were isolated from healthy volunteer donors following leukapheresis by negative selection. T cells were cultured in complete media (RPMI 1640 supplemented with 10% heat inactivated fetal bovine serum (FBS), 100 U/ml penicillin, 100 μg/ml streptomycin sulfate, 10-mM HEPES), and stimulated with anti-CD3 and anti-CD28 mAbs coated beads (Invitrogen, Grand Island, N.Y.) as described (Levine et al., 1997, J. Immunol. 159:5921-5930). 12-24 hr after activation, T cells were transduced with lentiviral vectors at MOI of ~5-10. $CD4^+$ and $CD8^+$ T cells used for in vivo experiments were mixed at 1:1 ratio, activated, and transduced. Human recombinant interleukin-2 (Novartis) was added every other day to a 50 IU/ml final concentration. Cell density of $0.5-1 \times 10^6$ cells/ml was maintained. Rested engineered T cells were adjusted for identical transgene expression prior to functional assays.

Cell Lines

Lentivirus packaging was performed in the immortalized normal fetal renal 293T cell line purchased from ATCC. Human cell lines used in immune based assays include the established human ovarian cancer cell lines A1847 and C30. For bioluminescence assays, target cancer cell lines were transfected to express firefly luciferase (fLuc), enriched by antibiotic selection positive expression by bioluminescence imaging. The human tumor cell line, C30, was transduced with lentivirus to express human mesothelin (C30-M) or human aFR (C30-F) or both (C30M/F). 293T cells and tumor cell lines were maintained in RPMI-1640 (Invitrogen, Grand Island, N.Y.) supplemented with 10% (v/v) heat-inactivated FBS, 2 mM L-glutamine, and 100 μg/mL penicillin and 100 U/mL streptomycin. All cell lines were routinely tested for mycoplasma contamination.

Cytokine Release Assays

Cytokine release assays were performed by coculture of $1 \times 10^5$ T cells with $1 \times 10^5$ target cells per well in triplicate in 96-well round bottom plates in a final volume of 200 ul of T cell media. After 20~24 hr, co-culture supernatants were assayed for presence of IFN-g using an ELISA Kit, according to manufacturer's instructions (Biolegend, San Diego, Calif.). Values represent the mean of triplicate wells. IL-2, IL-4, IL-10, TNF-a and MIP-1a cytokines were measured by flow cytometry using Cytokine Bead Array, according to manufacturer's instructions (BD Biosciences, San Jose, Calif.).

Cytotoxicity Assays $^{51}Cr$ release assays were performed as described (Johnson et al., 2006, J. Immunol. 177:6548-6559). Target cells were labeled with 100 uCi 100 uCi $^{51}Cr$ at 37° C. for 1.5 hours.

Target cells were washed three times in PBS, resuspended in CM at $10^5$ viable cells/mL and 100 uL added per well of a 96-well V-bottom plate. Effector cells were washed twice in CM and added to wells at the given ratios. Plates were quickly centrifuged to settle cells, and incubated at 37° C. in a 5% $CO_2$ incubator for 4 or 18 hours after which time the supernatants were harvested, transferred to a lumar-plate (Packard, Pangbourne, UK) and counted using a 1450 Microbeta Liquid Scintillation Counter (Perkin-Elmer). For the bystander cytotoxicity assays, $^{51}Cr$ labeled mesothelin-negative target cells were mixed with unlabelled mesothelin-positive targets cells at a ratio 1:1 for a final concentration of $10^5$ viable cells/ml before being incubated with the effector T cells at the given ratios. Spontaneous $^{51}Cr$ release was evaluated in target cells incubated with medium alone. Maximal $^{51}Cr$ release was measured in target cells incubated with SDS at a final concentration of 2% (v/v). Percent specific lysis was calculated as (experimental−spontaneous lysis/maximal−spontaneous lysis) times 100.

Xenograft Model of Ovarian Cancer

Six to 12-week-old NOD/SCID/γ-chain−/− (NSG) mice were bred, treated and maintained under pathogen-free conditions. For an established ovarian cancer model, 6 to 12-week-old female NSG mice were inoculated s.c. with $5\times10^6$ A1847 fLuc+ cells on the flank on day 0. For the bilateral mouse model $5\times10^6$ of A1847M$^+$/F$^+$ and A1847M$^+$/F$^-$ cells were inoculated s.c. separately in the same NSG mice on opposite hind flanks. After tumors were established at about 7 weeks, human primary T cells were activated, and transduced as described above. After 2 weeks T cell expansion, when the tumor burden was 250-350 mm$^3$, mice were i.v injected with T cells. Tumor dimensions were measured with calipers, and tumor volumes calculated using the formula V=1/2(length×width$^2$), where length is greatest longitudinal diameter and width is greatest transverse diameter. Animals were imaged prior to T cell transfer and about every week thereafter to evaluate tumor growth. Photon emission from fLuc+ cells was quantified using the "Living Image" software (Xenogen, Alameda, Calif.) for all in vivo experiments.

Bioluminescence Imaging

Tumor growth was also monitored by Bioluminescent imaging (BLI). BLI was performed using Xenogen IVIS imaging system and the photons emitted from fLuc-expressing cells within the animal body were quantified using Living Image software (Xenogen, Alameda, Calif.). Briefly, mice bearing A1847 fLuc$^+$ tumor cells were injected intraperitoneally with D-luciferin (150 mg/kg stock, 100 μL of D-luciferin per 10 grams of mouse body weight) suspended in PBS and imaged under isoflurane anesthesia after 5-10 minutes. A pseudocolor image representing light intensity (blue, least intense; red, most intense) was generated using Living Image. BLI findings were confirmed at necropsy.

Flow Cytometric Analysis

The following MAbs were used for phenotypic analysis: PE mouse anti-Human CD3; FITC anti-human CD4; APC anti-human CD8; PE-anti-human CD45, APC-Cy7 anti-human CD69, Alexa 647 anti-human CD107a and Alexa 647 anti-human CD107b. 7-AAD was used for viability staining. All mAbs were purchased from BD Biosciences, San Jose, Calif. In T cell transfer experiments, peripheral blood was obtained via retro-orbital bleeding and stained for the presence of human CD45, CD4, and CD8 T cells. After gating on the human CD45$^+$ population, the CD4$^+$ and CD8$^+$ subsets were quantified using TruCount tubes (BD Biosciences, San Jose, Calif.) with known numbers of fluorescent beads as described in the manufacturer's instructions. Tumor cell surface expression of mesothelin was performed using soluble P4 anti-mesothelin scFv followed by PE-labeled streptavidin. T cell surface expression of the M-CAR was evaluated using V5-tagged recombinant mesothelin followed by Alexa-647 conjugated anti-V5 tag or biotinylated streptavidin. F-CAR expression was evaluated using GFP as a reporter gene. Acquisition and analysis was performed using a BD FACS CANTO II with DIVA software.

Immunohistochemistry

Mice were euthanized by CO2 inhalation and tumors were collected in Tissue-Tek O.C.T. Compound, and frozen at −80 oC. A standard Strept-avidin horseradish immunoperoxidase method was used for human CD3 staining. Primary and secondary antibodies were diluted in buffer containing 10% normal goat serum. 7 μm cryosections were fixed in cold acetone for 5 min at 4° C. and blocked with Dako's (Carpentaria, Calif.) peroxidase blocking system for 10 minutes. Sequential incubations included the following: 10% normal goat serum (30 min at RT); primary rabbit anti-human CD3 monoclonal antibody (Thermo Scientific RM-9107) at 1:100 dilution (45 min. at RT); secondary biotinylated goat anti-rabbit antibody at 1:200 dilution (30 min at RT); strept-avidin-biotinylated horseradish peroxidase complex reagent (Dako) (30 min at RT); and three 5 minute washes in buffer after each incubations. Sections were then exposed to the chromagen DAB plus from Dako for 5 min at RT and counterstained with hematoxylin, dehydrated, cleared and mounted. For the quantification of CD3$^+$ T cells within the tumors, T cells were counted in 10 randomly selected intratumoral fields of each slide at high magnification (20×).

Apoptosis Assay

CAR T cells ($3\times10^5$) were co-cultured with equal number of tumor cells ($3\times10^5$) for three days. After the co-culture period the cells were stained with CD3 Ab and recombinant mesothelin for CAR expression. Then the cells were washed with phosphate-buffered saline, and labeled with annexin V-FITC and 7AAD using an Apoptosis Detection Kit (BD Pharmingen) according to instructions from the manufacturer. Samples were run on a FACScan, and data were analyzed using Cellquest.

Degranulation Assay

The degranulation assay was performed as earlier described (Betts et al., 2003, J Immunol Methods, 281(1-2): 65-78) with minor modifications. Target cells ($1\times10^5$) were co-cultured with an equal number of effector cells in 0.1 mL per well in a 96-well plate in triplicate. Control wells contained either T cells alone. Anti-CD107a and Ab Anti-CD107b (10 ul per well) or IgG1 conjugated to FITC (BD Biosciences, San Jose, Calif.) were added in addition to 1ul/sample of monensin (BD Biosciences, San Jose, Calif.) and incubated for 4-5 h at 37° C. Cells were washed 2 times with PBS, stained for expression of the P4 CAR, CD8 and CD69 and analyzed on a FACS DIVA II.

Statistical Analysis

Statistical analysis was performed using two-way repeated measures ANOVA for the tumor burden (tumor volume, photon counts). Student's t test was used to evaluate differences in absolute numbers of transferred T cells, cytokine secretion and specific cytolysis. Kaplan-Meier survival curves were compared using the log-rank test. GraphPad Prism 4.0 (GraphPad Software) was used for the statistical calculations. $P<0.05$ was considered significant.

The results of the experiments are now described.

CAR Construction

Anti-mesothelin CAR constructs comprised of the P4 scFv linked to a CD8a hinge and transmembrane region, followed by a CD3-z signaling moiety alone (M-z) or in tandem with the CD28 intracellular signaling motif were previously shown to confer specific mesothelin-redirected activity in vitro and in vivo (Lanitis et al., 2012, Mol. Ther. 20:633-643) (FIG. 1A). The costimulatory only anti-aFR CAR (F-28) construct is comprised of the MOv-19 scFv linked to a CD8a hinge and CD28 transmembrane region, followed by the CD28 intracellular signaling motif; the signaling deficient F-Dz construct lacks functional signaling domains (FIG. 1A). Primary human T cells were efficiently transduced with the two CAR-encoding lentiviral vectors with >40% dual transduced T cells reproducibly expressing both CARs (FIG. 1B). CART cell populations were adjusted to equivalent frequencies of anti-mesothelin CART cells (60-70%) by adding untransduced T cells for all functional assays.

Figure 2A:
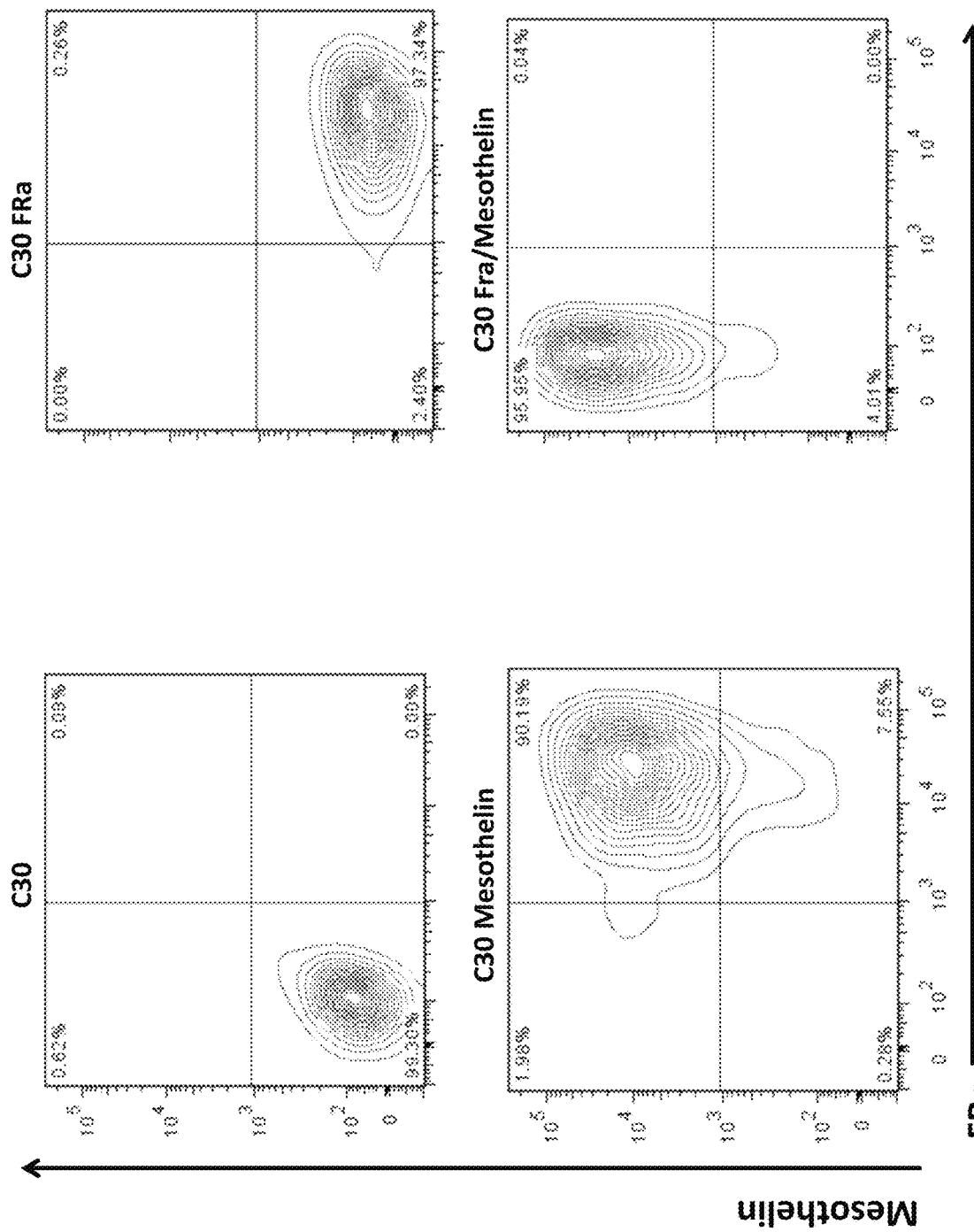
FIGS. 2A-2E, depicts the results of experiments demonstrating that trans-signaling CART cells exert superior antigen specific cytokine secretion in vitro compared with first generation CAR T cells.
Figure 2B:
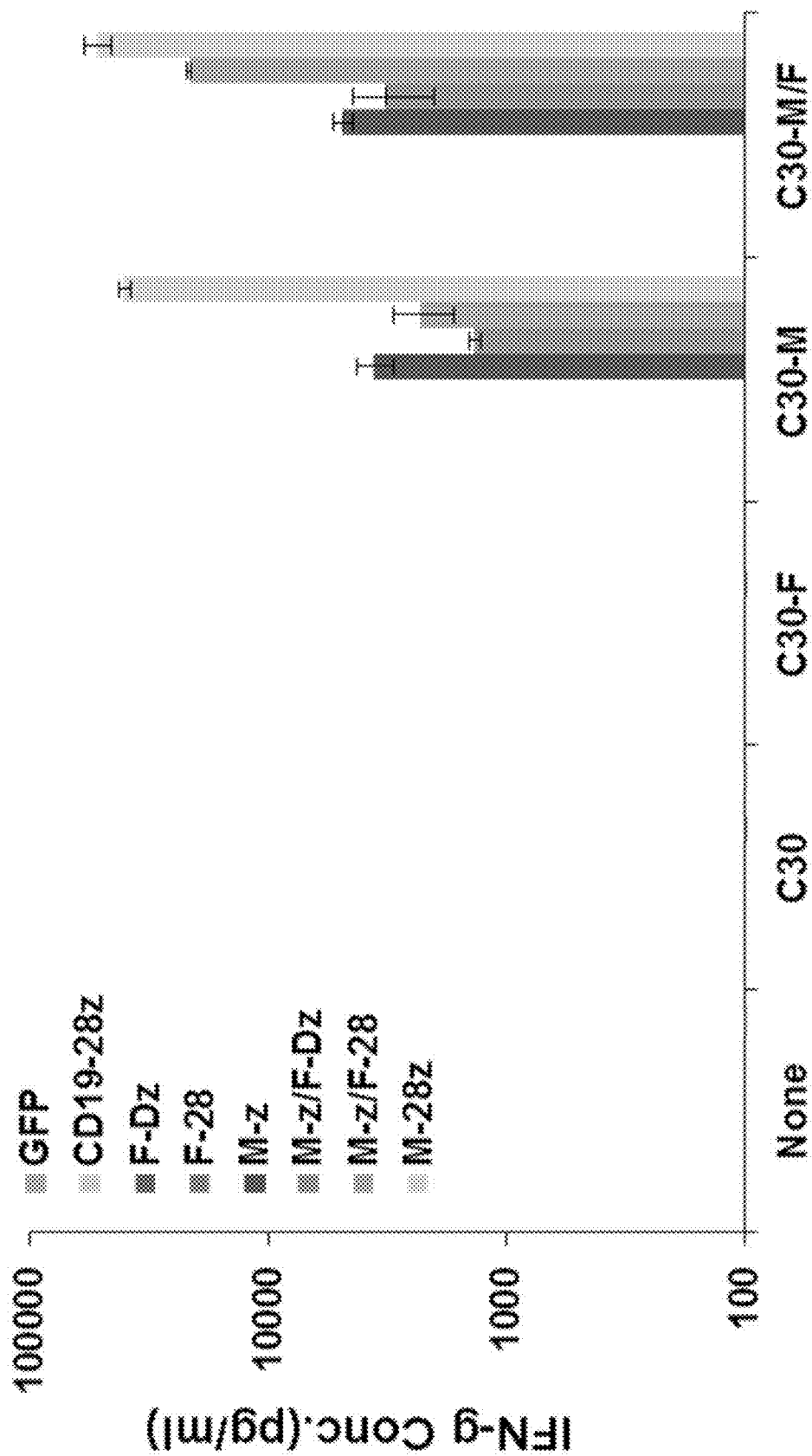

Trans-Signaling CART Cells Exert Superior Antigen Specific Cytokine Secretion In Vitro To evaluate the in vitro effector functions of CART cells in response to cells that express mesothelin alone versus tumor cells that co-express mesothelin and aFR, TAA-negative C30 cancer cell lines were engineered to over-express both antigens alone or together (FIG. 2A). T cells engineered to express the M-z CAR recognized and secreted similar levels of IFN-γ when co-cultured with C30 cells expressing either mesothelin (C30M) or mesothelin and aFR (C30M/F). Second generation M-28z CAR T cells exerted superior IFN-γ secretion against all C30 cell variants. In contrast, trans-signaling M-z/F-28 CART cells produced low levels of IFN-γ against C30M similar to M-z CART cells. However, when exposed to C30M/F tumor cells, M-z/F-28 CART cells exerted enhanced IFN-g production. M-z/F-28 CAR activity against C30M/F cells also surpassed that of M-z CART cells demonstrating that expression of both antigens promotes the costimulation of M-z/F-28 CART cells through F-28 CAR. Consistent with this notion, co-expression of the M-z and the signaling-deficient F-Dz CAR in T cells did not enhance their response against C30-M/F cells. T cells expressing F-28 CAR alone in did not produce any IFN-γ consistence with the absence of CD3-z signaling. Moreover, control T cells transduced to express green fluorescent protein (GFP) or an anti-CD19 CAR containing CD3t with CD28 signaling motifs in tandem (CD19-28z) (Milone et al., 2009, 17:4617-4627) did not produce cytokines after stimulation with CD19-negative C30 cells, illustrating the need for antigen-specificity.

Figure 2C:
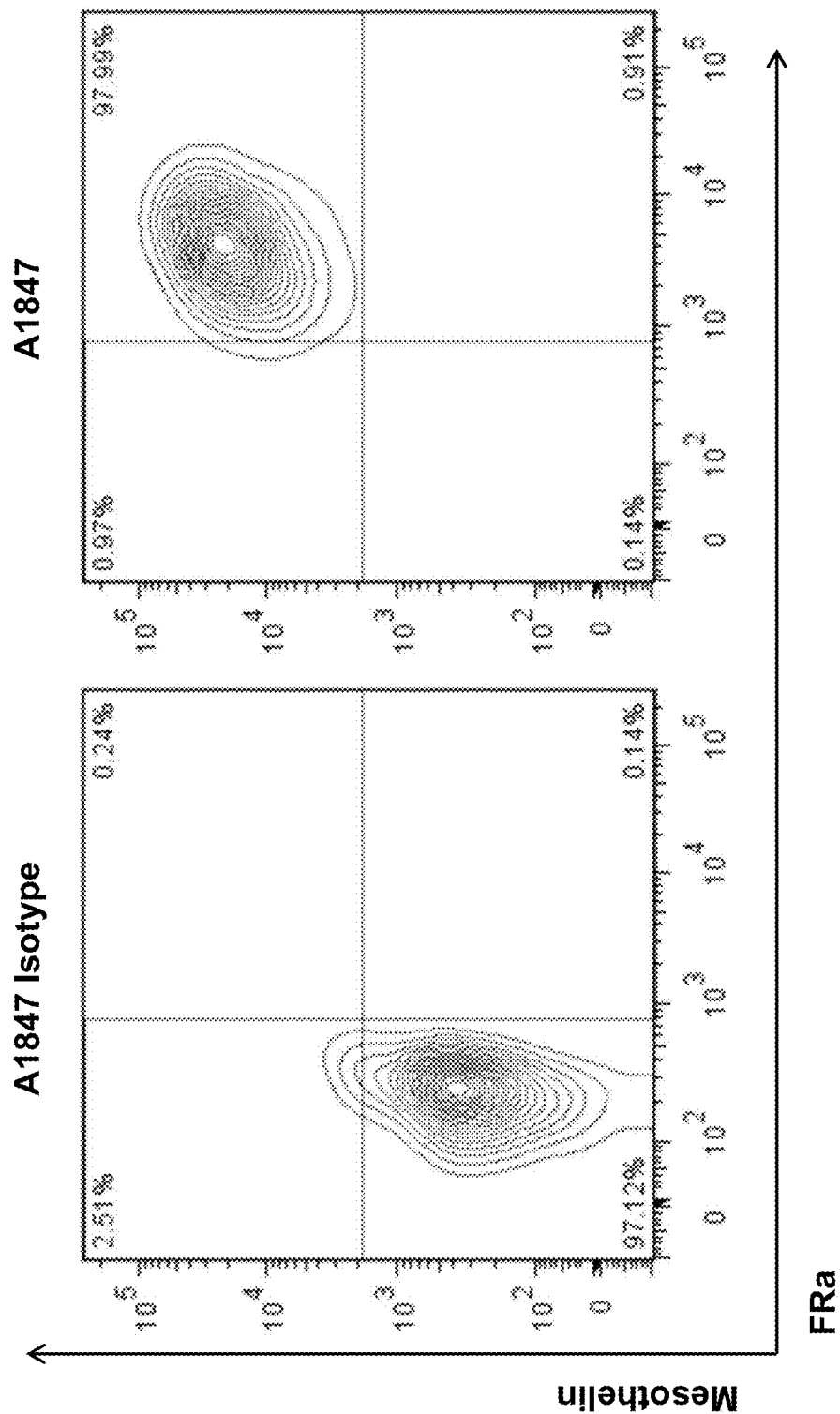
Figures 2D, 2E:
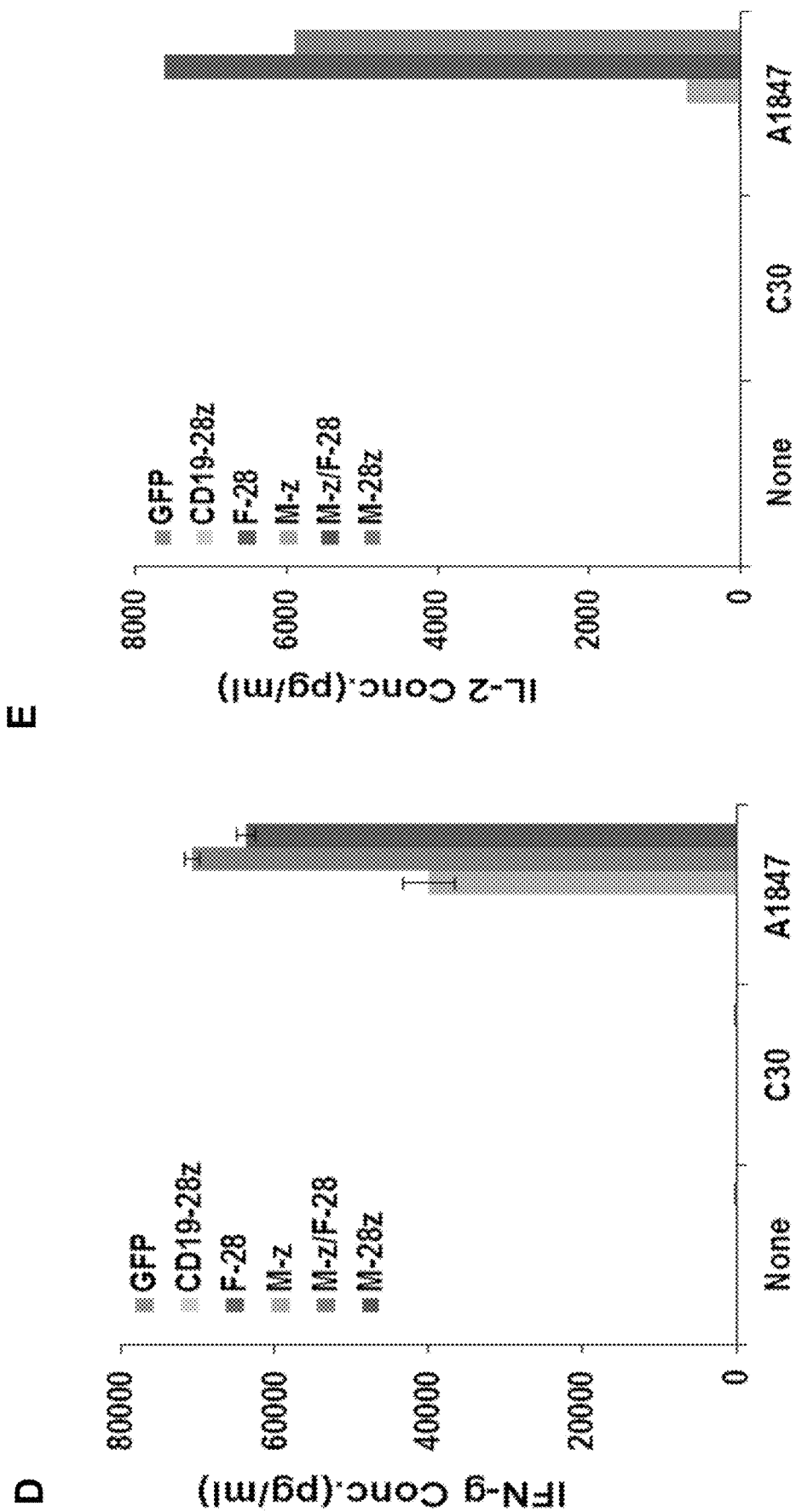

To test trans-signaling in a more clinically meaningful model, an ovarian cancer cell line that naturally expresses both mesothelin and aFR, A1847 was employed (FIG. 2C). Trans-signaling CART cells secreted significantly higher levels of IFN-γ in response to A1847 compared to M-z CART cells, and similar to cis-signaling M-28z CART cells showing that the natural expression of both antigens on tumor cells is capable of inducing costimulatory effects to trans-signaling CART cells (FIG. 2D). IL-2 secretion from the dual transduced M-z/F-28 CART cells was similar to second generation P4-28z CART indicating that integrated delivery of signal 1 and 2 in trans or cis can synergistically enhance production of the latter cytokine (FIG. 2E).

Trans-Signaling CAR T Cells Show In Vitro Cytolytic Potency

Figure 3A:
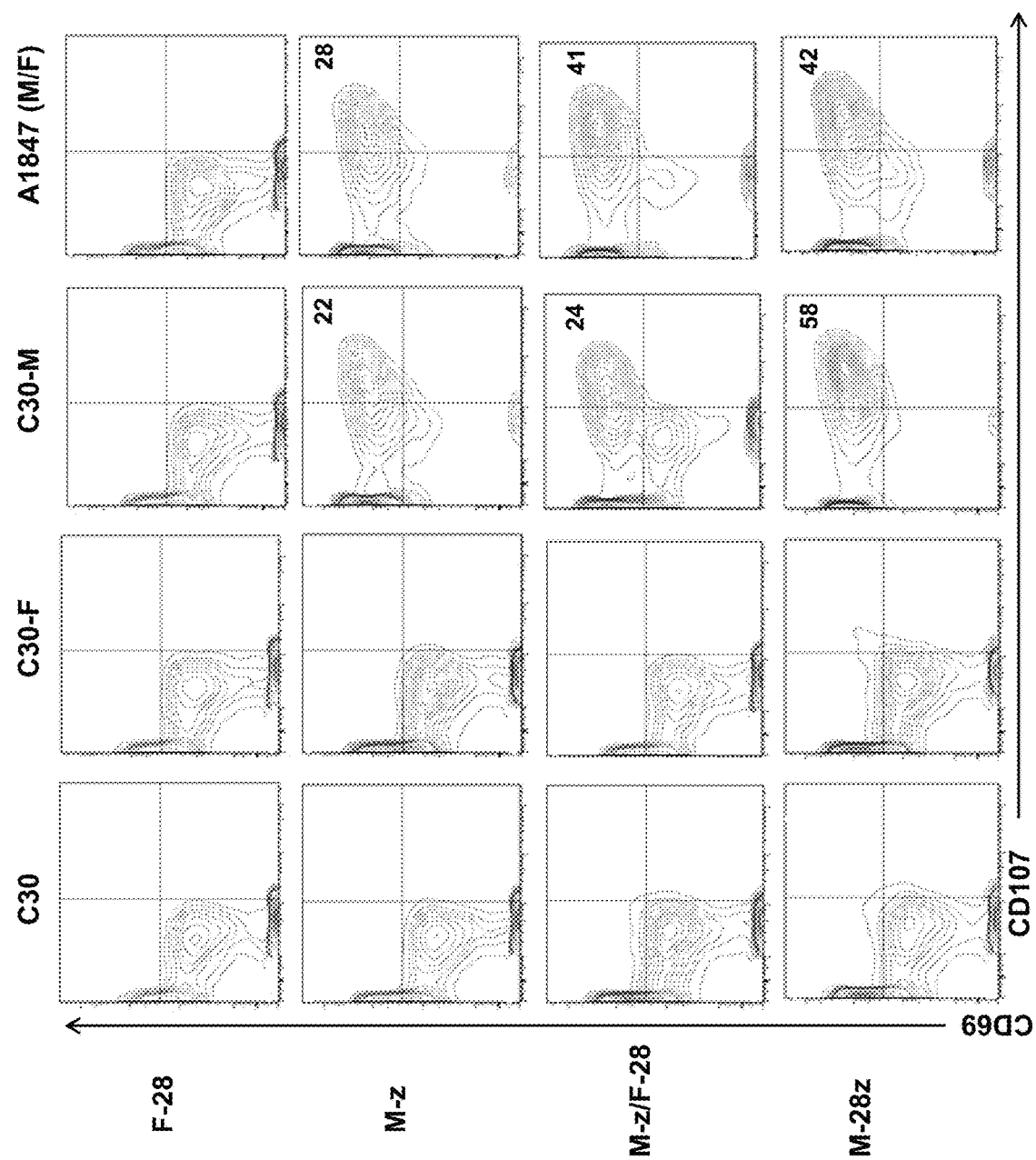
FIGS. 3A-3B, depicts the results of experiments demonstrating that trans-signaling CAR T cells show equivalent in vitro cytolytic potency.
Figure 3B:
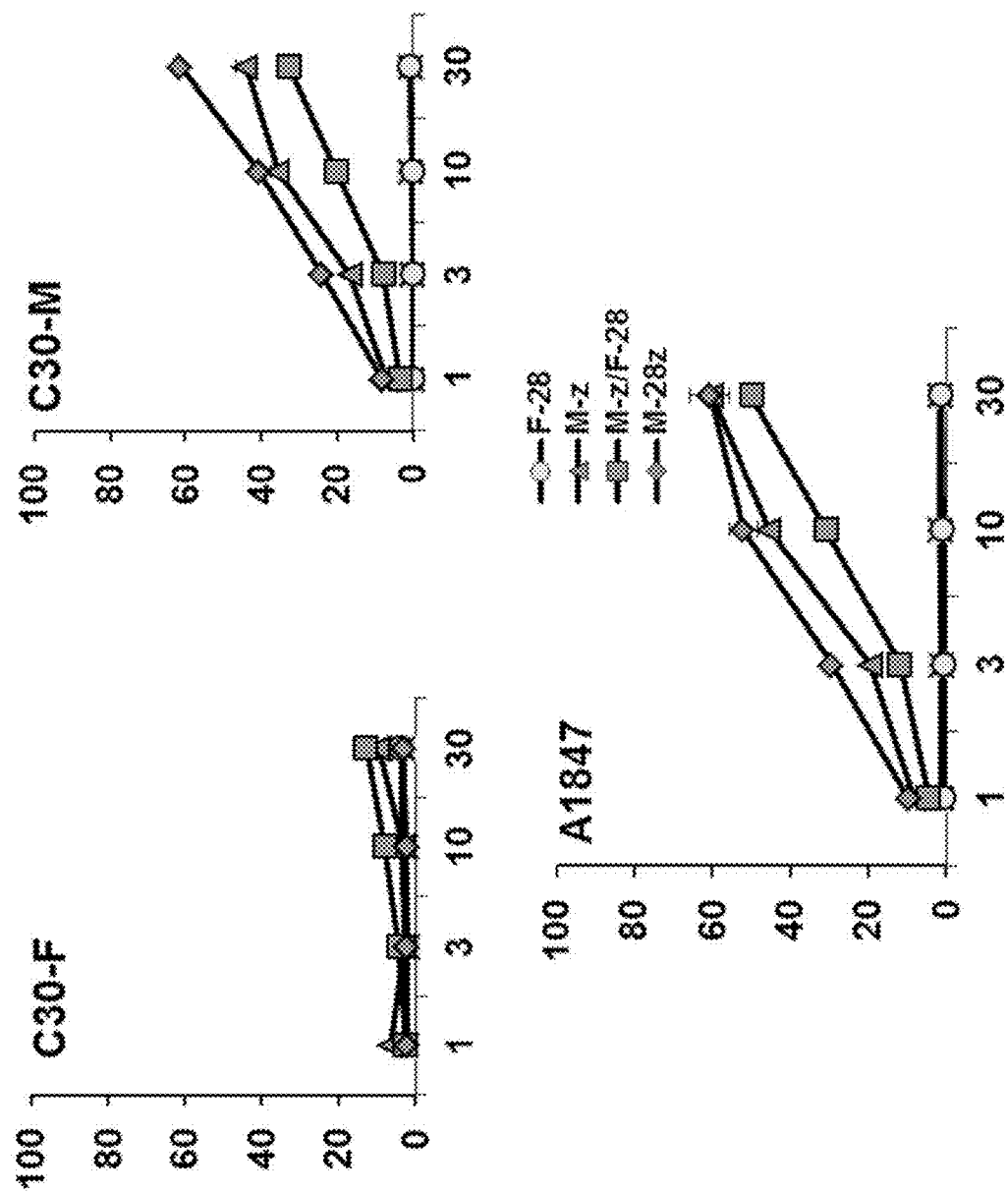

Degranulation is a quantitative indicator of lytic function by T cells (Song et al., 2011, Cancer Res. 71:4617-1627). M-z and M-z/F-28 CAR CD8+ T cells degranulated with similar upregulation of surface co-expression of mobilized CD107 (Lysosomal-associated membrane protein 1) and the activation-associated marker CD69 in response to C30M, but not when stimulated with C30 (FIG. 3A). Consistent with active costimulation, M-28z CART cells displayed a superior cytolytic phenotype against C30M compared with M-z and M-z/F-28 CART cells. In contrast, exposure to A1847 tumor cells led to equivalent and elevated degranulation by cis M-28z and trans M-z/F-28 CART cells which was higher than by M-z CART cells (FIG. 3A). GFP-T cells and anti-CD19 CART cells did not degranulate in response to C30 or A1847. In chromium release assays, the cytolytic function by the various CART cell populations was similar against A1847 target cells although slightly higher release of $^{51}$Cr was observed in the M-z and M-28z co-cultures (FIG. 3B). In contrast, M-28z CART cells specifically lysed C30M cells at a higher level compared with M-z and M-z/F-28.

Trans-Signaling CAR T Cells are Resistant to AICD

Figures 4A, 4B:
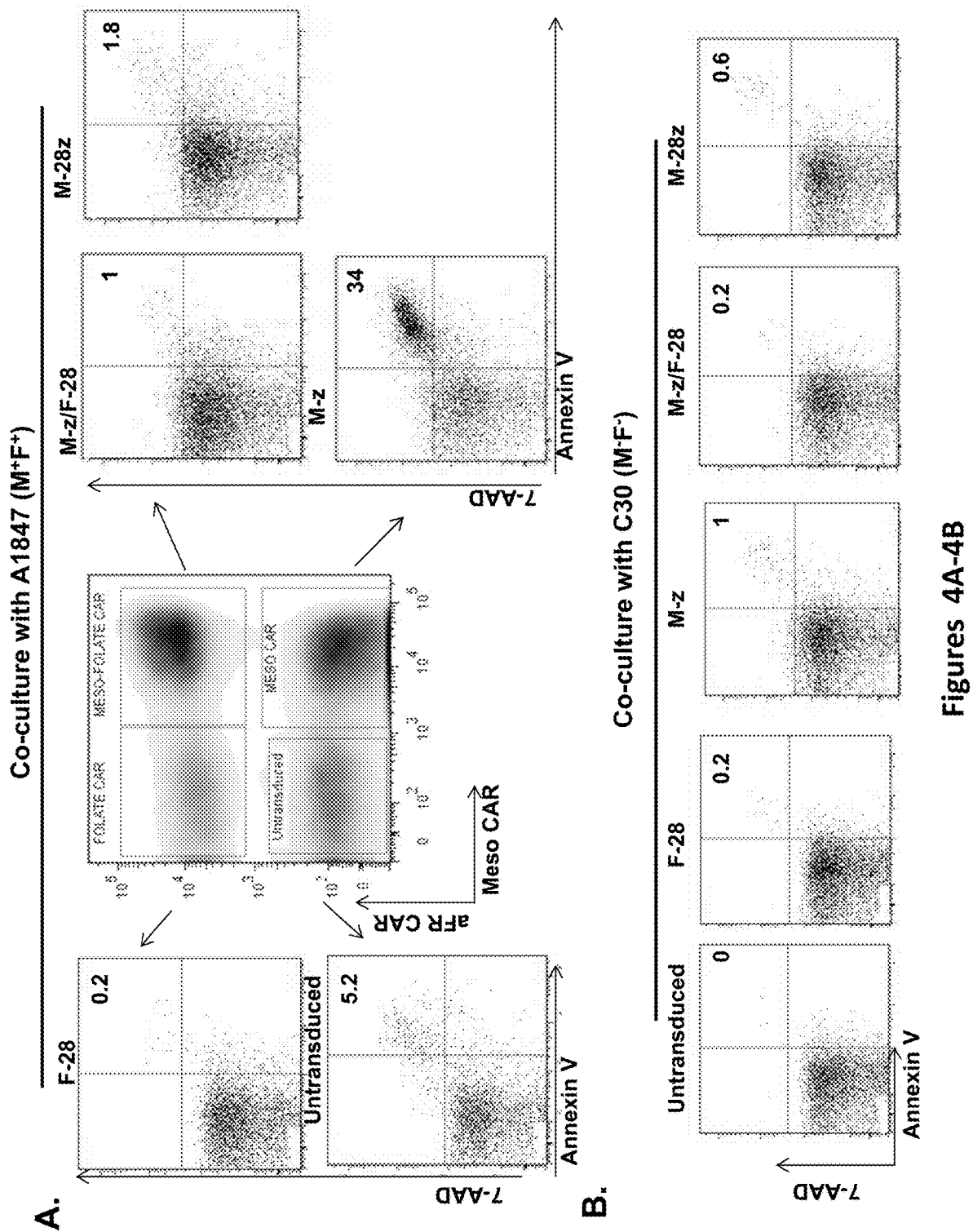
FIGS. 4A-4B, depicts the results of experiments demonstrating that the integration of CD28 signaling in cis or in trans increases in vitro T-cell survival upon antigen specific stimulation and inhibition of antigen-induced post activation cell death.

Incorporation of costimulatory signaling regions into CARs has been shown to increase resistance of CART cells to apoptosis upon activation with tumors (Hombach et al. 2007, 56:731-737). To investigate if provision of CD28 costimulation in trans protects T cells from antigen-induced cell death (AICD), single or dual CAR bearing T cells were co-cultured with A1847 tumor cells (M+/F+) for three days and then measured for their rate of apoptosis by staining the T cells with 7-AAD and Annexin V. Apoptosis was elevated in M-z T cells exposed to A1847 (34%) but reduced in trans-signalling M-z/F-28 CART cells (0.5-1%; FIG. 4A). F-28 or control CD19-28z CART cells displayed no AICD, consistent with the absence of antigenic stimulation. Consistent with past studies (Zhong et al., Mol. Ther. 2010, 18:413-420), cis-signaling M-28z CART cells were also resistant to AICD (FIG. 4B).

Figures 5A, 5B, 5C:
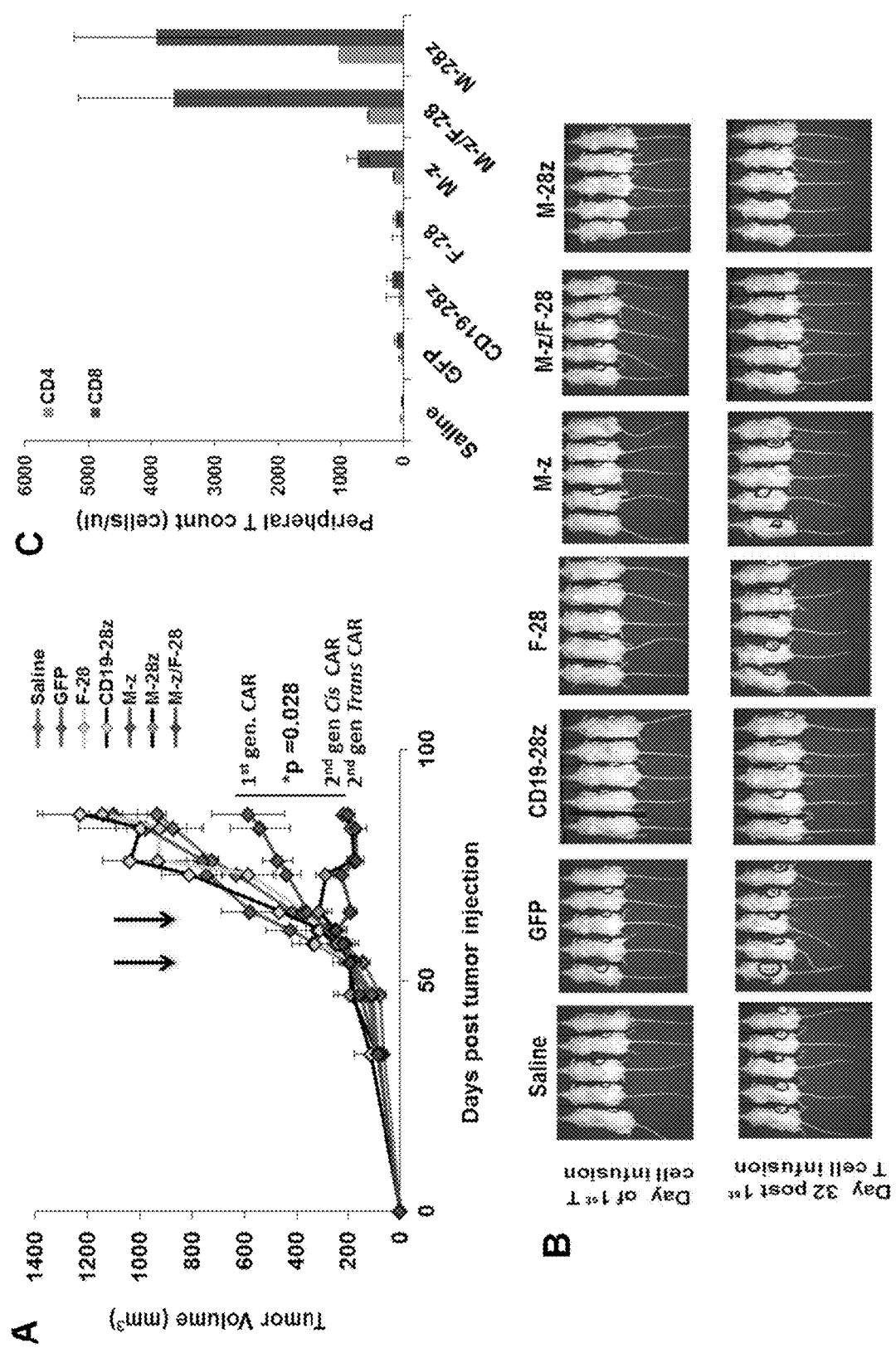
FIGS. 5A-5C, depicts the results of experiments demonstrating that trans signaling CAR T cells exert superior anti-tumor effector functions in vivo compared with first generation CAR T cells.

Dual-Specific CAR T Cells Possess Enhanced In Vivo Anti-Tumor Potency and Persistence The capability of trans-signaling CART cells to inhibit human tumor outgrowth was evaluated in vivo in immuno-deficient NOD/SCID/IL-2R-γc$^{null}$ (NSG) mice inoculated s.c. with 1×10$^6$ firefly luciferase-expressing A1847 cells. Mice with established A1847 tumors (150-200 mm$^3$) received intravenous injections of CART cells on days 55 and 59 post-tumor inoculation. Tumor growth was modestly but significantly inhibited in mice receiving M-z CART cells (p=0.043), compared to saline, CD19-28z CART cells, F-28 CART cells or GFP-T cell control groups 4 weeks after first T cell dose (FIG. 5A). Transfer of cis M-28z or trans M-z/F-28 CART cells mediated similar and significantly better inhibition of tumor outgrowth (p=0.028) compared to M-z T cells indicating that incorporation of CD28 signaling domain in cis or trans enhances the anti-tumor activity in vivo against tumors co-expressing mesothelin and FRa TAAs (FIG. 5A). Measurement of the tumor-derived luciferase signaling from the treated mice confirmed the lower tumor burden in the mice treated with the trans-signaling CART cells compared with first generation CART cells. Bioluminescence signals from tumors of mice treated with trans- or cis-signaling CART cells was similar (FIG. 5B). Two weeks after first T cell dose, peripheral blood CD8+ T and CD4+ T cell counts from mice injected with cis M-28z or trans M-z/F-28 CART cells were similar and significantly higher than in the M-z group (p<0.05; FIG. 5C). No substantial human T cell persistence was observed in mice treated with CD19-28z CART, F-28 CART or GFP-T cells.

Figure 9A:
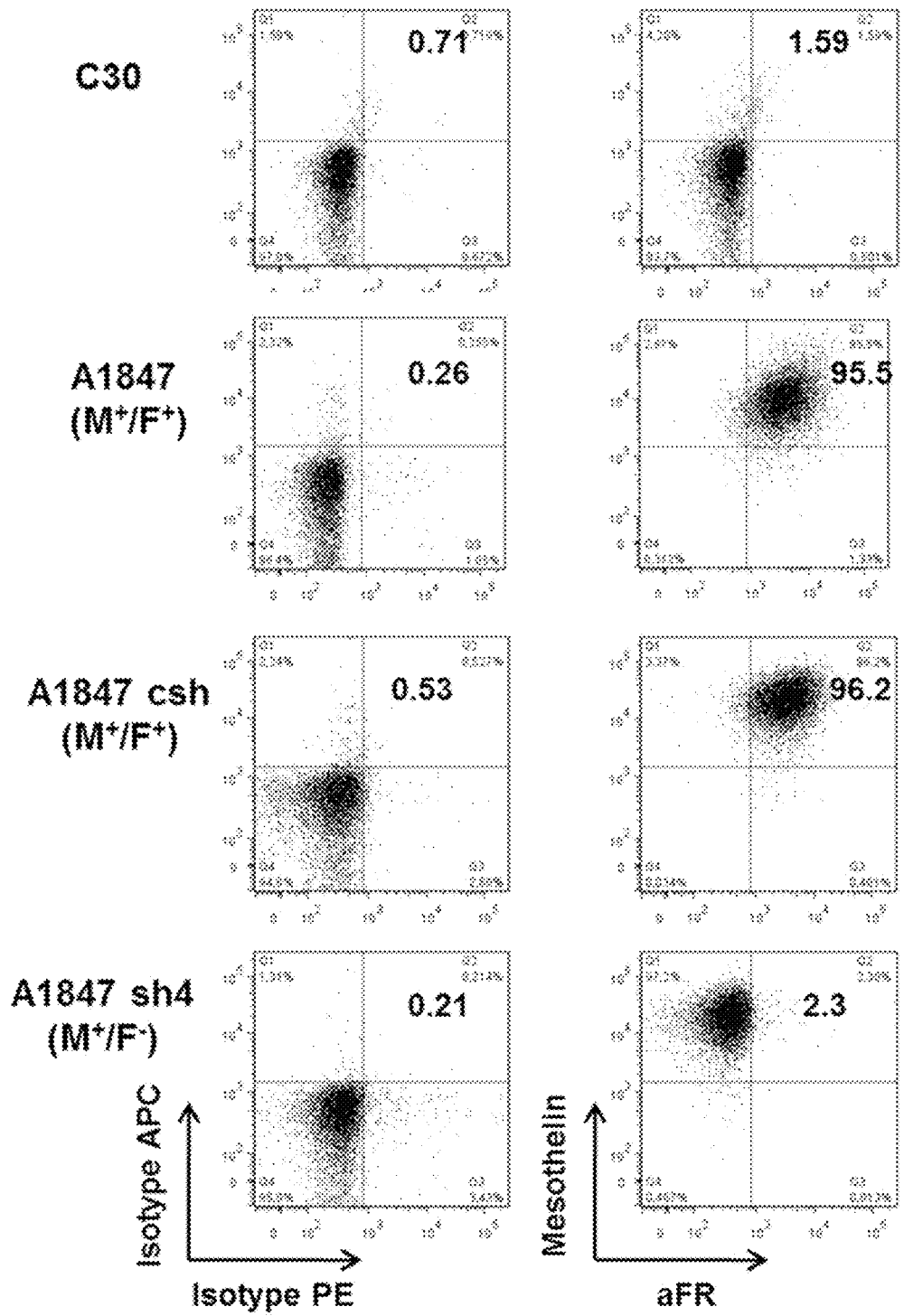
FIGS. 9A-9B, depicts the results of experiments demonstrating that trans-, but not cis-, signaling CAR T cells exhibit more limited in vitro activity against cells bearing single antigen.
Figure 9B:
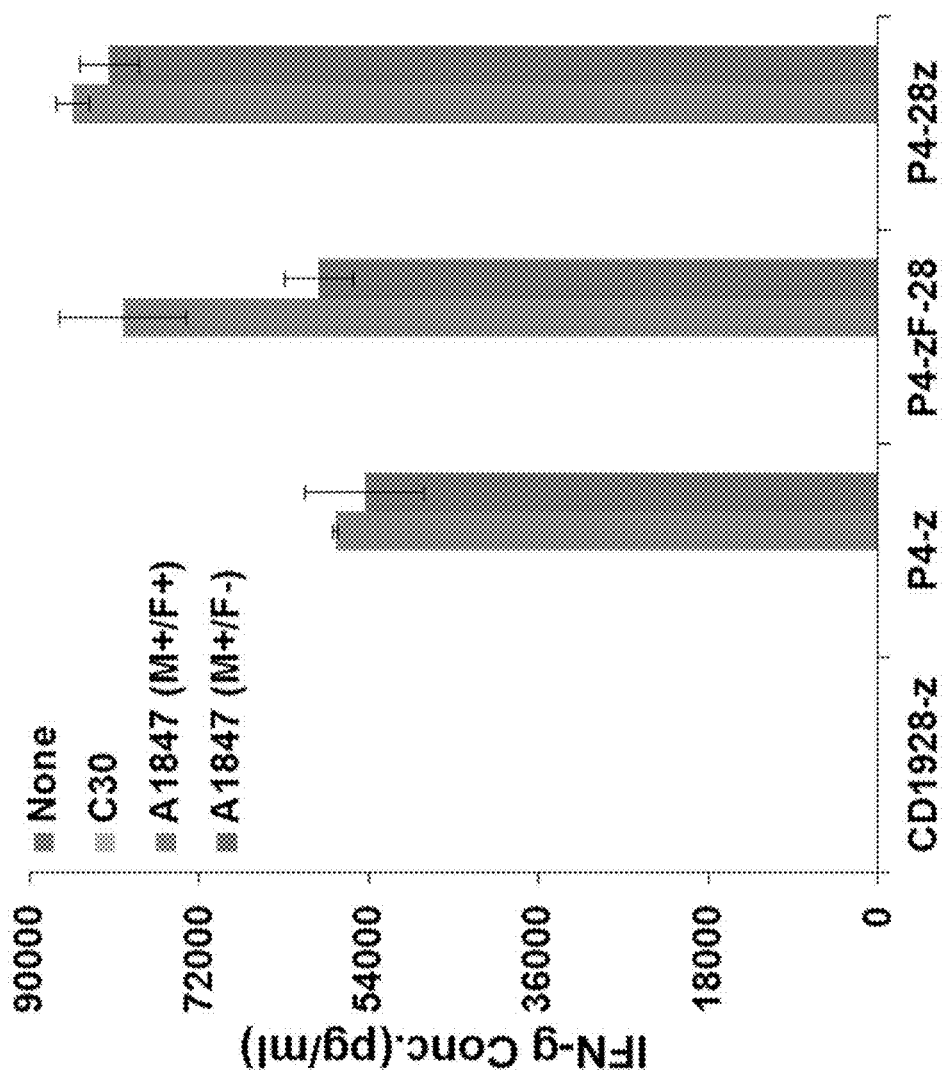

Trans-, But Not Cis-, Signaling CAR T Cells Exhibit More Limited In Vivo Activity Against Cells Bearing Single Antigen FRa-deficient A1847 cells were generated via transduction with lentiviral particles encoding for an shRNA specific for silencing aFR gene expression, as a surrogate for normal human mesothelial cells expressing only mesothelin. Fluorescence-activated cell sorting resulted in an enriched cancer cell population (~98%) which lacked surface aFR expression (A1847M$^+$/F$^-$) (FIG. 9). aFR expression was unaltered after engineering cells with control shRNA (A1847M$^+$/F$^+$). No difference in the in vitro growth kinetic of A1847M$^+$/F$^+$ and A1847M$^+$/F$^-$ cells was observed. In co-culture assays, IFN-g secretion by trans M-z/F-28 CART cells was significantly reduced in response to A1847M$^+$/F$^-$ compared with A1847M$^+$/F$^+$, a confirmation of potent effector function only upon engagement of both antigens (FIG. 9B). Further, the level of reactivity by M-z/F-28 and M-z CART cells against A1847M$^+$/F$^-$ was not statistically different. Comparatively, cis M-28z CAR T cells secreted significantly higher amounts of IFN-g against A1847M$^+$/F$^-$, similar to that achieved with A1847M$^+$/F$^+$.

Figure 6A:
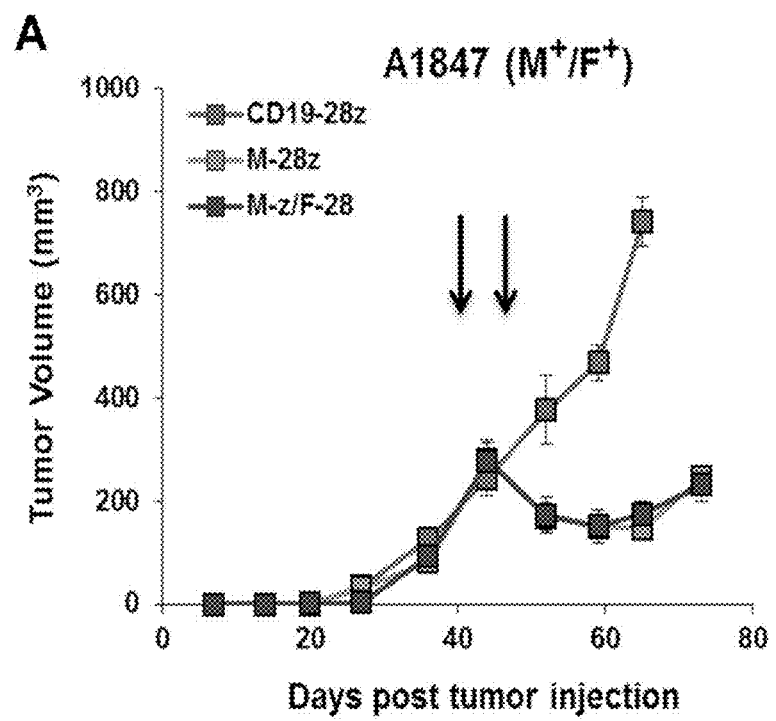
FIGS. 6A-6D, depicts the results of experiments demonstrating that trans-, but not cis-, signaling CAR T cells exhibit more limited in vivo activity against cells bearing single antigen.
Figure 6B:
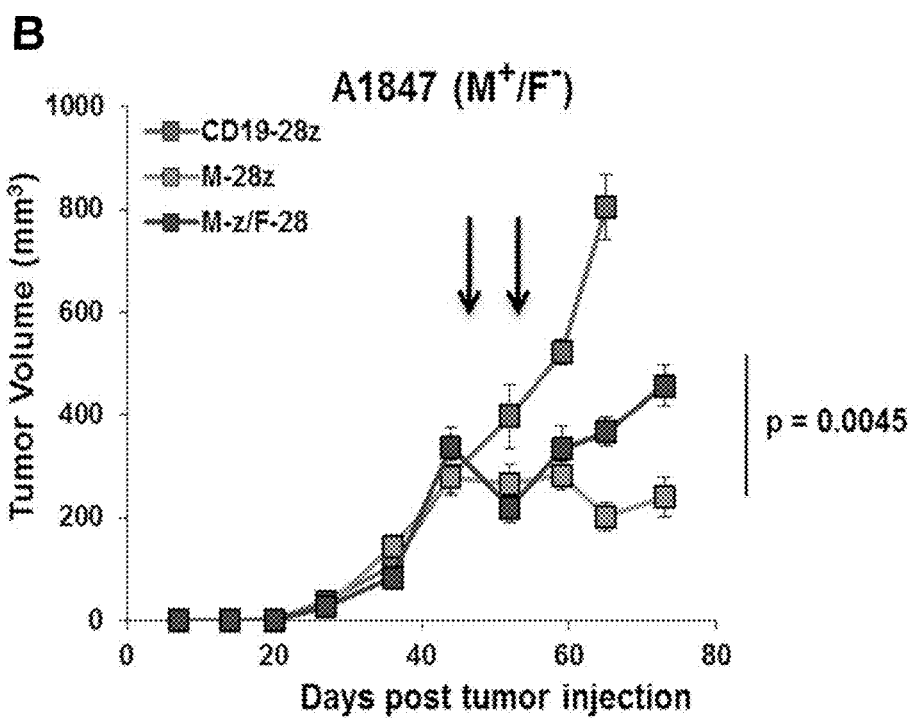
Figure 6C:
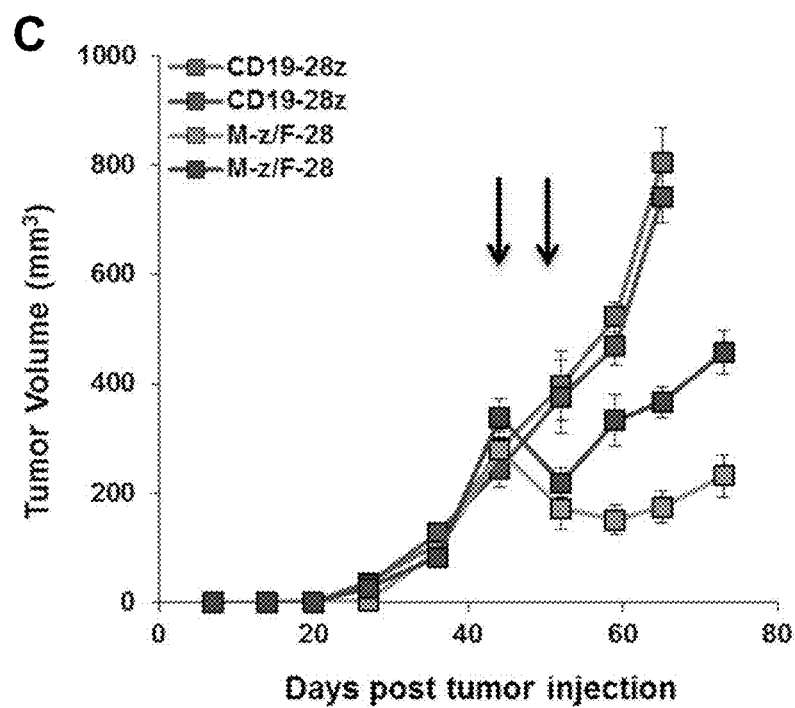
Figure 6D:
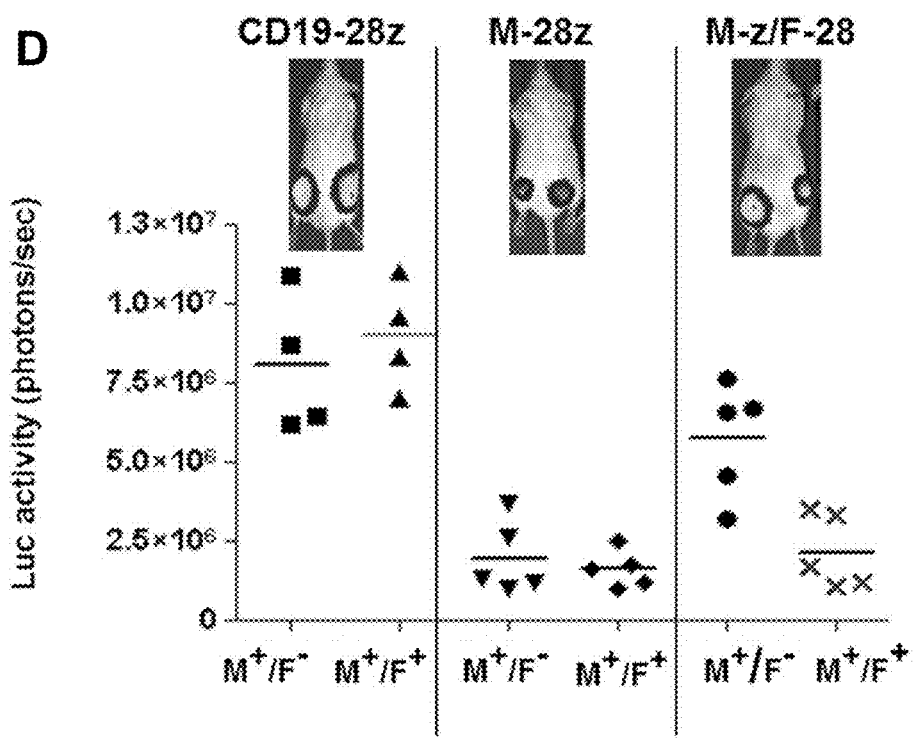

To evaluate the in vivo potency of trans- or cis-signaling T cells against A1847 cells expressing or lacking aFR, $5 \times 10^6$ A1847M$^+$/F$^+$ and A1847M$^+$/F$^-$ cells were inoculated s.c. separately in the same NSG mice on opposite hind flanks. Mice with the two established A1847 (>330 mm$^3$) tumors received tail vein injections of CART cells on days 45 and 49 post-tumor inoculation and monitored for tumor outgrowth. Control of A1847M$^+$/F$^+$ tumor outgrowth was identical between the trans M-z/F-28 CART and cis-signaling M-28z CART cell groups (FIG. 6A). In contrast, inhibition of A1847M$^+$/F$^-$ outgrowth was partially but significantly attenuated in the trans M-z/F-28 CART cell group compared with the cis M-28z mice group (p=0.0045; FIG. 6B). Further, trans-signaling CART cells were statistically less effective in inhibiting the outgrowth of A1847M$^+$/F$^-$, compared with their activity against the A1847M$^+$/F$^+$ tumor in the same mice (p=0.0001; FIG. 6C). Bioluminescence imaging of the tumors confirmed these results (FIG. 6D).

Preferential Accumulation of Trans-Signaling CAR T Cells in Tumor In Vivo

Figure 7A:
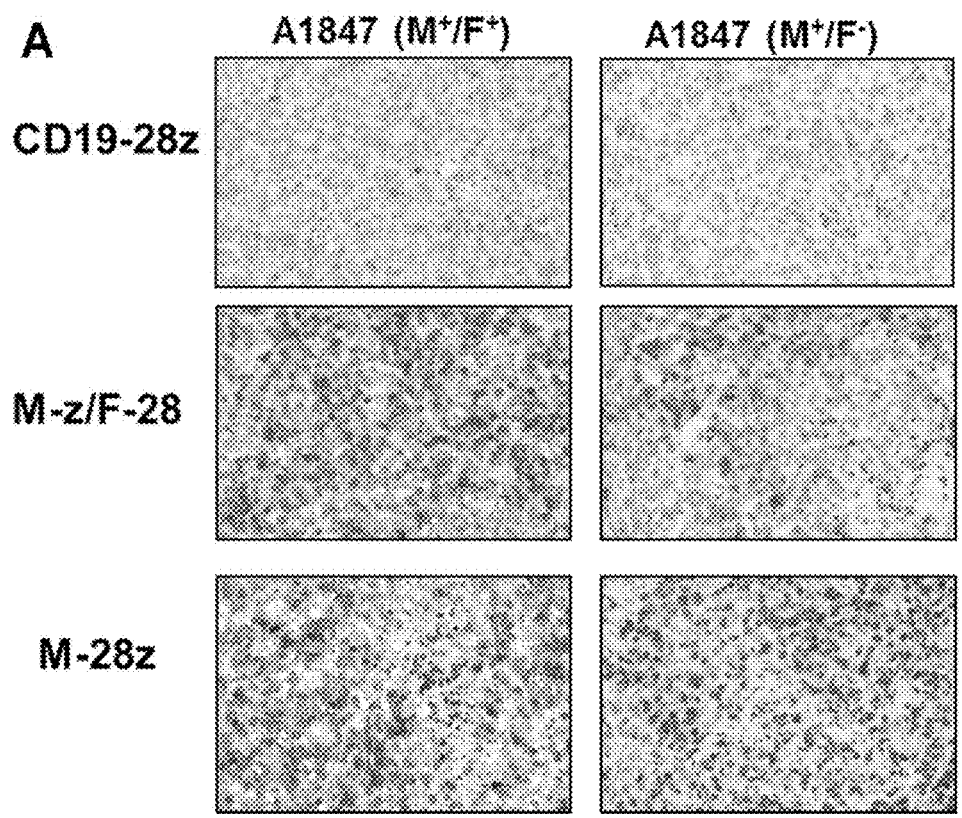
FIGS. 7A-7B, depicts the results of experiments demonstrating that trans signaling CAR T-cell preferentially localize to dual antigen-expressing tumors in vivo.
Figure 7B:
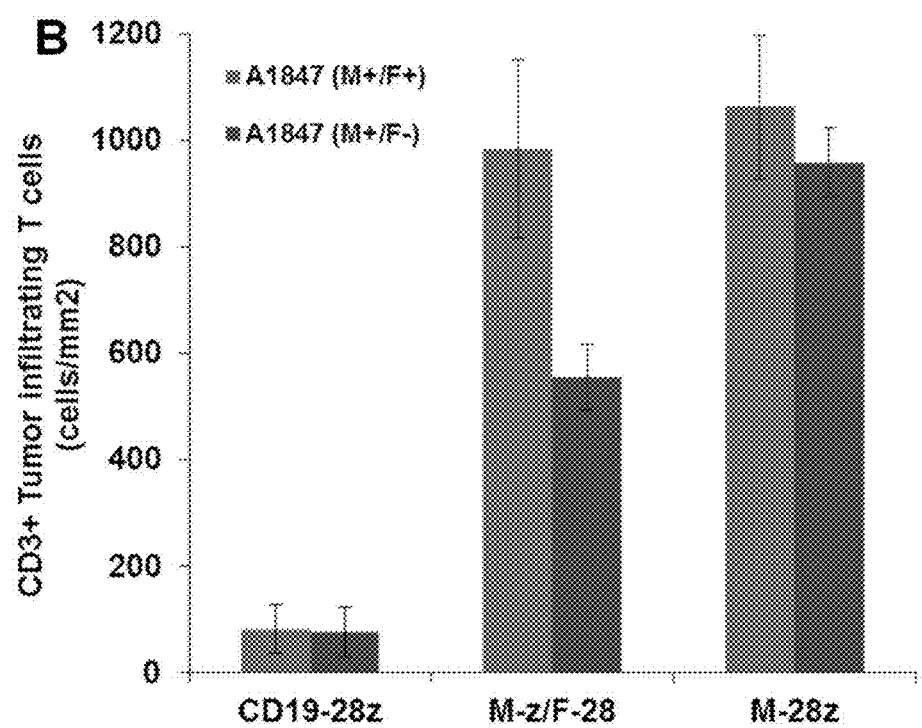
Figure 8:
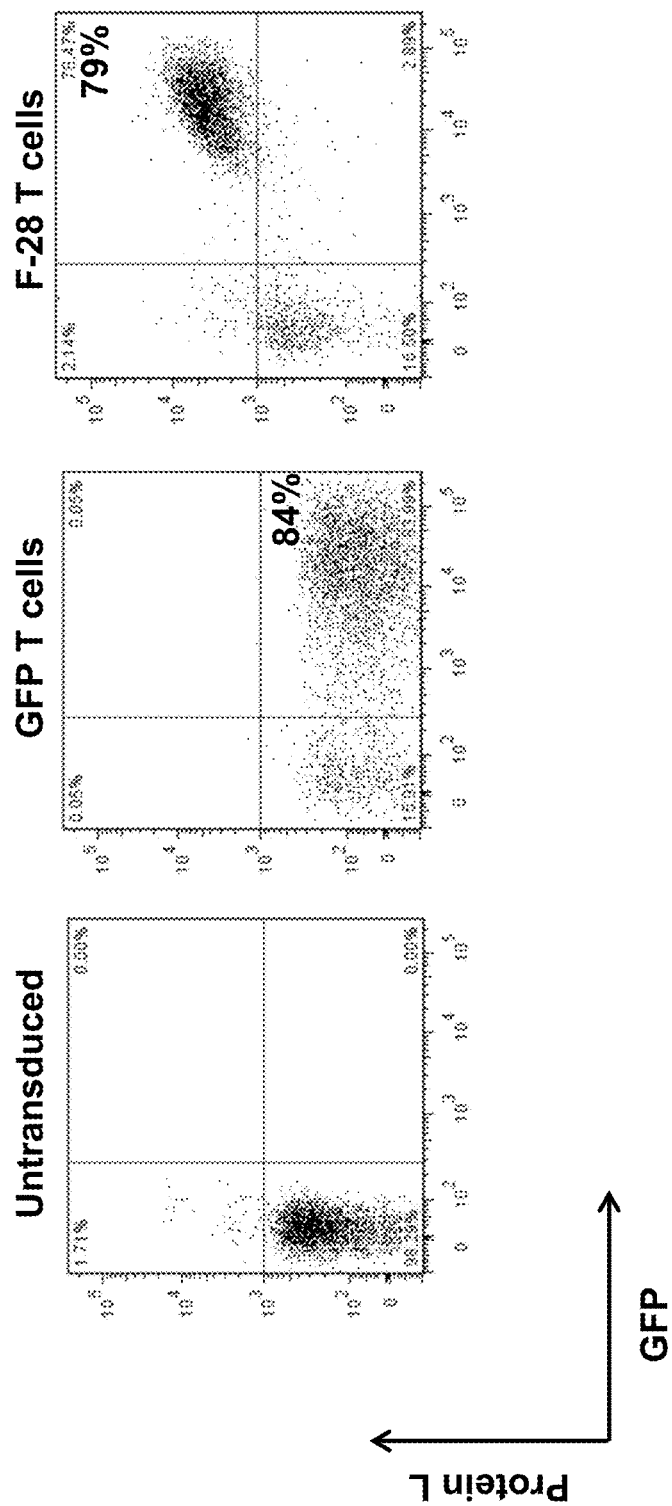
FIG. 8 is an image depicting the correlation of GFP transgene expression and Protein L binding to the scFv. F-28 CAR T cells were lentivirally transduced and 5 days after were stained with biotinylated Protein-L followed by SA-APC. Transduction efficiency was also monitored using GFP transgene expression. Transduction efficiencies are indicated with the percentage of CAR expression of the transduced populations.

The accumulation of trans- and cis-signaling CART cells in regressing tumors from treated and euthanized mice with established masses in both flanks was measured. Resected tumors from each group were harvested and subjected to immunohistochemical analysis for the detection of human CD3$^+$ T cells (FIG. 7). The abundance of T cells in dual (A1847M$^+$/F$^+$) or single antigen expressing tumors (A1847M$^+$/F$^-$) from mice treated with cis M-28z CART cells was high and not statistically significantly different. In contrast, a significant increase in T cell accumulation was observed in tumors expressing both antigens compared to single antigen in mice treated with trans M-z/F-28 CART cells, illustrating selectivity. Few CD3$^+$ T cells were detected in tumors resected at the same time from mice that received CD19-28z CART cells. Altogether these data show that the survival and accumulation of trans signaling CAR T cells into tumor sites is highly dependent upon engagement of FRa antigen to the FRa specific-CAR for the optimal delivery of costimulation.

Trans-Signaling CAR Approach

Adoptive immunotherapy involving genetic modification of T cells with antigen-specific, chimeric, single-chain receptors is a promising approach for the treatment of cancer (Plaimauer et al., 2002, Blood, 100:3626-3632). An important consideration for the therapeutic use of adoptively transferred, gene-engineered T cells is whether they may induce extensive autoimmune damage to normal tissues expressing the target antigen (Ertl et al., 2011, Cancer Res. 71:3175-3181). The latter phenomenon has been observed in pre-clinical mouse models and clinical trials either using T cells genetically modified to express an exogenous tumor specific TCR or T cells redirected through the incorporation of a chimeric antigen receptor (Heslop, 2010, Mol. Ther. 18:661-662). Mild to severe autoimmune toxicity has been reported following transfer of tumor reactive T cells (Jena et al., 2010, Blood, 1035-1044; Zhong et al., 2010, Mol. Ther. 18:413-420) including liver toxicity in patients upon adoptive transfer of T cells gene-modified with an anti-CAIX scFv receptor (Feugier et al., 2004, Blood 104:2675-2681) due to CAIX expression on bile duct epithelium. Serious adverse events involving death of a patient has been observed in to two distinct clinical trials following adoptive transfer of T cells gene-modified against CD19 (Morgan et al., 2010, Cancer J. 16:336-341; Brentjens et al., 2010, Mol. Ther. 18:666-668) or T cell genetically modified to express an ErbB2-specific CAR (Morgan et al., 2010, Cancer J. 16:336-341). Collectively, studies both in preclinical mouse models and in patients have indicated that the number of T cells administered, the levels and location of antigen expressed on normal tissue, the type of signaling domains incorporated into chimeric receptors, and the level of immune preconditioning used must be carefully considered for use in engineered T-cell therapy. (Ertl et al., 2011, Cancer Res. 71:3175-3181; Straathof et al., 2005, Blood 105:4247-4254; Cohen et al., 1999, Lymphoma 34:473-480; Thomis et al., 2001, Blood, 97:1249-1257; Tey et al., 2007, Biol. Blood Marrow Transplant 13:913-924; Di Stasi et al., 2011, N. Engl. J. Med. 365:1673-1683; Kuo et al., 2010, Lab Chip 10:837-842).

Chimeric antigen receptors with one or more costimulatory signals confer a new potential to respond to antigen with sustained proliferation and cytotoxicity, resistance to activation-induced cell death (AICD) and regulatory T-cell suppression (Song et al., 2011, Cancer Res. 71:4617-4627; Emtage et al., 2008, Clin. Cancer Res. 8112-8122). However, the power of costimulation holds the potential for sustained survival and activation against normal host tissues expressing low levels of the TAA. One approach to forestall this problem involves the physical separation of signal 1 module (CD3ζ) from the signal 2 module (costimulation) through their incorporation into two distinct CARs specific for two different antigens, to recapitulate natural T cell biology and function. In this way, dual CART cells may selectively traffic, survive and exert sustained proliferation within the tumor microenvironment since synergistic signals would be delivered to T-cells preferentially at that location. Hence, the potential for "on-target" toxicity should be reduced commensurately. CARs can be engineered to provide co-stimulation alone (Krause et al., 1998, J. Exp. Med. 188:619-626). Furthermore, when jurkat cells are engineered to co-express hapten-specific CD3ζ- and CD28-based CARs, complementary signaling can occur, leading to IL-2 production (Alvarez-Vallina et al., Eur. J. Immunol. 26:2304-2309). Attempts to preferentially redirect CART cell function against tumors expressing multiple antigens to limit potential toxicity have been documented without much success or potential for clinical application. One study attempted to enhance the specificity of CART cells for tumor by endowing them with two first generation CARs specific for ErbB2 and a-folate receptor. Dual-transduced T-cell populations expressed similar amounts of total surface CARs as mono-transduced T cells, but with lower expression of each individual CAR (Duong et al., 2011, Immunotherapy 3:33-48). This allowed for activity of dual transduced T cells against target cells expressing individual antigens being less than against tumor cells expressing both antigens. Since no costimulation is provided into these CAR T cells due to the lack of costimulatory signaling regions in the individual CARs themselves, they are unlikely to survive, persist and clear tumors in vivo. Another recent study proposed dual targeting of ErbB2 and MUC1 in breast cancer by generating dual CAR T cells transduced with both a CD28 containing MUC1 CAR and a CD3t containing ErbB2 CAR (Wilkie et al., 2010, Immunotherapy 4:365-367). In that study, dual CAR T cells were even less efficient than first generation CART cells and failed to secrete IL-2 in response to trans-signaled costimulation upon encounter with second antigen thus rendering the system not applicable for further pre-clinical investigation.

Figure 10:
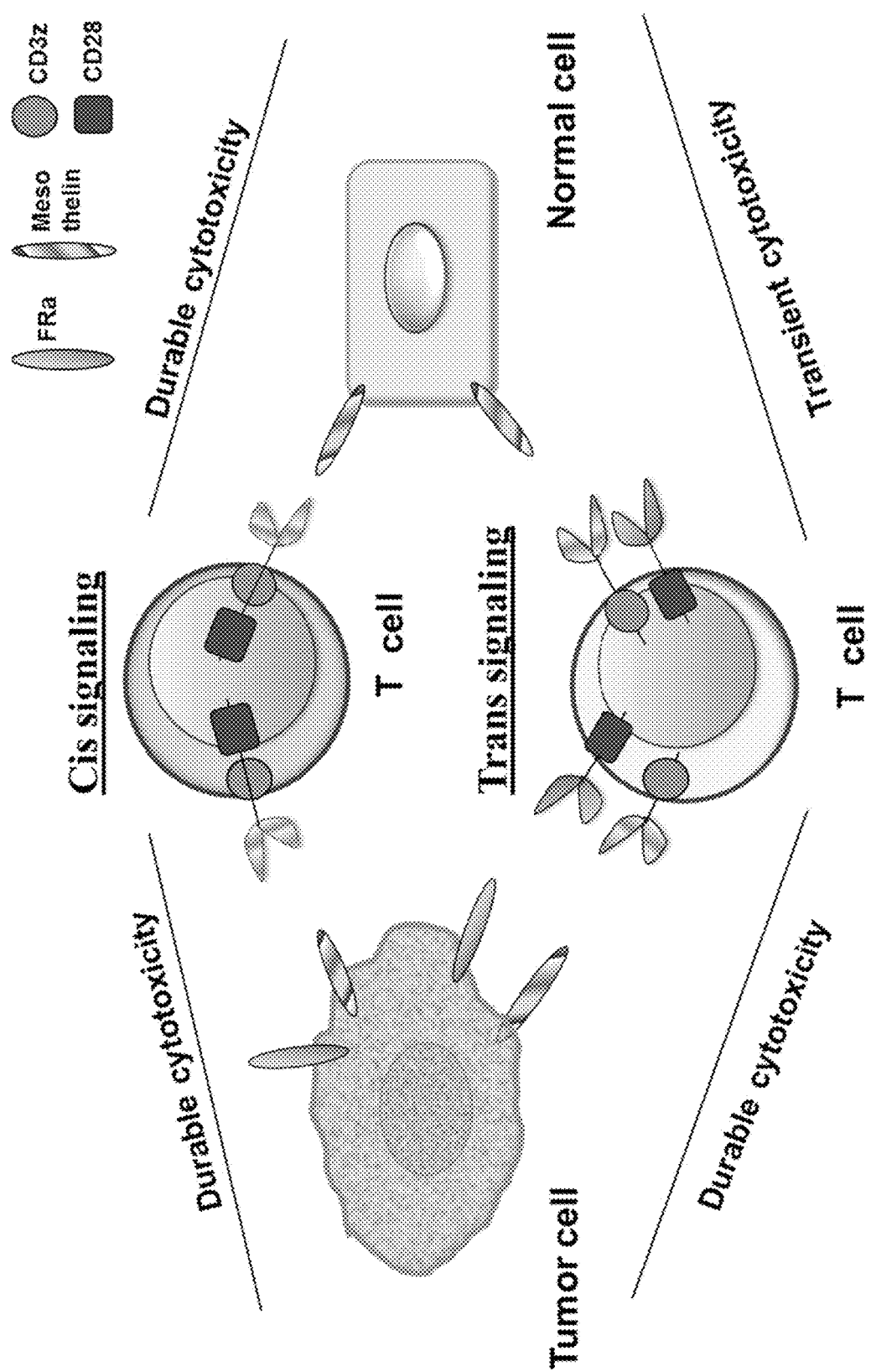
FIG. 10 is a schematic illustration depicting the dissociation of signaling molecules in two distinct CARs.
Figures 11A, 11B, 11C:
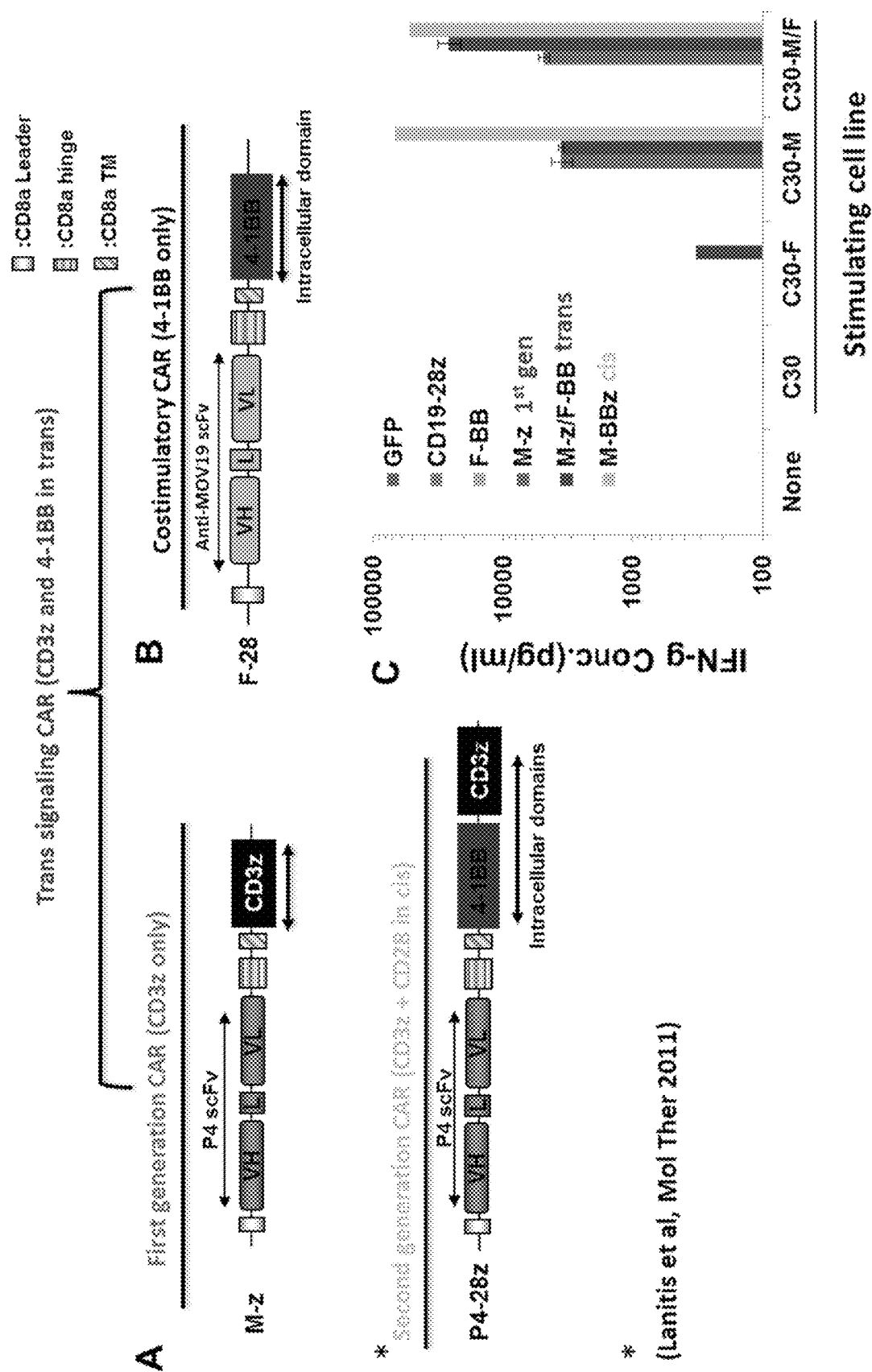
FIGS. 11A-11C, depicts a schematic illustration of the costimulatory domain in trans-signaling CAR T cells bearing 4-1BB exerting superior IFN-g secretion compared with the P4-z CAR T cells against meso/folate expressing tumor cells.

Here, two different CARs redirected against mesothelin and aFR were utilized to test the concept of dissociated CAR signaling for selective anti-tumor activity (FIG. 10). The anti-mesothelin CAR contains the CD3 signaling motif alone whereas the anti-aFR CAR includes only the intracellular domain of the CD28 costimulatory molecule. Proper costimulation of these engineered T cells relies upon the co-expression of both aFR and mesothelin on the tumor cell surface. In comparisons between trans-signaling CAR T cells with conventional first and second generation anti-mesothelin CART cells, trans-signaling CART cells showed similar in vitro potency to cis-signaling CAR T cells and were capable of producing increased levels of Thl cytokines compared to first generation CART cells. Notably, tumor-induced costimulation through the anti-aFR-28 CAR was capable of triggering enhanced secretion of IL-2, a cytokine known to promote T cell proliferation and persistence in vivo (Kowolik et al., 2006, Cancer Res. 66:10995-11004; Sadelain et al., 2009, Curr. Opin. Immunol. 21:215-223). Furthermore, the costimulation delivered in trans was sufficient to protect those CART cells from AICD, similar to the effects seen in cis-signaling second generation CART cells (Song et al., 2012, Blood 119:696-706; Zhong et al., 2010, Mol. Ther. 18:413-420). The cytolytic potential of trans-signaling CART cells in vitro was similar to first and second generation CART cells. This is consistent with previous studies demonstrating no statistically significant difference in specific tumor lysis by CAR T cells that include or lack incorporated costimulatory signaling regions (Savoldo et al., 2011, J. Clin. Invest. 121:1822-1826; Song et al., 2011, Cancer Res. 71:4617-4627; Hombach et al., 2001, Cancer Res. 61:1976-1982).

The significance of a trans-signaling CAR approach is best tested in using preclinical models where the simultaneous targeting of human tumor cells and representative normal human tissue cells by CART cells can be evaluated. Ovarian cancers generally over express both aFR (90%) and mesothelin (70%), making this an attractive cancer type for study (Toffoli et al., 1997, Int. J. Cancer 74:193-198; Hassan et al., 2005, Appl. Immunohistochem. Mol. Mofphol. 13:243-247). Moreover, the pattern of mesothelin and aFR expression on normal tissues is largely non-overlapping. Mesothelin is expressed by normal mesothelial cells lining the pleura, peritoneum and peritoneum and at low levels by epithelial cells of the trachea, tonsils, fallopian tube and the testis (Chang et al., 1992, 50:373-381; Ordonez, 2003, Mod. Pathol. 16:192-197). FRa expression is limited to the apical surface of the proximal tubules of the kidney, choroid plexus, lung epithelium, thyroid and intestinal brush border epithelial cells (Weitman et al., 1992, Cancer Res. 52:3396-3401; Holm et al., 1993, Adv. Exp. Med. Biol. 338:757-760).

In this study, in vivo anti-tumor activity of trans-signaling CART cells was initially tested by adoptively transferring the different CART cell populations into immunodeficient mice with established ovarian cancer, using the A1847 human ovarian cancer cell line expressing both mesothelin and FRa. It was found that trans-signaling CART cells exhibit potent antitumor activity against ovarian cancer in vivo, equivalent to that achieved using conventional cis-signaling CAR T cells. More importantly, the finding that trans-signaling CAR T cells are more selective, potent and localized within cancers which bear both antigens, and comparatively spare normal cells bearing single antigen, may have important translational ramifications. It has been recently shown that mesothelin redirected T cells bearing an anti-mesothelin chimeric antigen receptor and a chemokine receptor (CCR2) increased the localization of the genetically engineered T cells in malignant pleural mesotheliomas secreting the chemokine CCL2 and thus improved the therapeutic outcome in pre-clinical mouse models (Moon et al., 2011, Clin. Cancer Res. 17:4719-4730).

Upon trafficking to the normal tissues expressing mesothelin alone, trans-signaling CART cells receive only signal 1 upon antigen contact, provided through the grafted TCR CD3 domain. This can potentially render the designer T cells susceptible to AICD or drive them into anergy (Zhong et al., 2010, Mol. Ther. 18:413-420; Emtage et al., 2008, Clin. Cancer Res. 14:8112-8122; Berry et al., 2009, Tissue Antigens 74:277-289) and restrict their potential for long term persistence and tumor elimination when applied to patients. Alternatively, recognition of aFR alone and singular transmission of CD28 signal, in the absence of mesothelin-directed CD3ζ-signals, does not activate trans-signaling CART cells. Importantly, equal regression of tumors was observed in the present model using cis- or trans-signaling CAR T cells, illustrating the idea that a dual CART cell approach can modestly improve safety for clinical application without significantly diminishing the antitumor potential of the second generation CAR approach. Dual CART cells which receive combined CD3t and costimulatory signals upon antigen-specific interactions with the tumor did not appear to be rendered costimulation-independent and endowed with the capacity to react strongly against the tissue expressing single antigen. This was apparent in the present preclinical model where there was a significant difference in the control of tumor bearing two antigens versus the more rapid growth of cells with only one antigen following treatment with trans M-z/F-28 CART cells. This was further supported by the statistically higher infiltration and accumulation of trans-signaling CART cells into the tumor sites where both antigens were expressed.

While trans-signaling CARs represent a novel approach to focus CART cells to tumor cells and reduce their impact on single antigen-expressing cells, this method is highly dependent upon identification of two antigens which are nearly uniformly expressed in a particular cancer type, with relatively low and non-overlapping expression in normal tissues. Accordingly, the identification and application of alternative approaches to limit CART-mediated autoimmune effects remains warranted. One approach to limit such toxicity is the careful design of a dose-escalation strategy to better define the optimal T cell dose (Ertl et al., 2011, Cancer Res. 71:3175-3181). Some of the potential side effects of nontumor cell recognition by CART cells can be overcome by the co-expression of conditional suicide genes such as such as incorporation of HSV-TK or the cytoplasmic domain of Fas or an inducible caspase incorporated into genetically engineered T cells to abort any aberrant T-cell responses (Straathof et al., 2005, Blood 105:4247-4254; Cohen et al., 1999, Leuk. Lymphoma 34:473-480; Thomis et al., 2001, Blood 97:1249-1257; Tey et al., 2007, Biol. Blood Marrow Transplant 13:913-924). Indeed the iCasp9 cell-suicide system has been shown to increase the safety of cellular therapies in patients that received T cells depleted of alloreactive progenitor cells (Di Stasi et al., 2011, N. Engl. J. Med. 365:1673-1683). Furthermore electroporation of T cells with optimized RNAs encoding for CARs allows for transient CAR expression as a safety measure, has been proven effective in preclinical mouse models and might bypass the associated safety concerns of integrating gene vectors (Zhao et al., 2010, Cancer Res. 70:9053-9061). Notably, these approaches toward cell product safety are not mutually exclusive and future application of dual CAR T cells engineered with suicide switches as described elsewhere herein may better permit localized T cells accumulation within the tumor microenvironment where they can preferentially exert enhanced anti-tumor potency in a safe manner.

Example 2

CAR Constructs

```
P4-z (amino acid sequence) (SEQ ID NO: 3)
MALPVTALLLPLALLLHAARPGSQVQLQQSGPGLVTPSQTLSLTCAISGDSVSSN

SATWNWIRQSPSRGLEWLGRTYYRSKWYNDYAVSVKSRMSINPDTSKNQFSLQ

LNSVTPEDTAVYYCARGMMTYYYGMDVWGQGTTVTVSSGILGSGGGGSGGGG

SGGGGSQPVLTQSSSLSASPGASASLTCTLRSGINVGPYRIYWYQQKPGSPPQYLL

NYKSDSDKQQGSGVPSRFSGSKDASANAGVLLISGLRSEDEADYYCMIWHSSAA

VFGGGTQLTVLSASTTTPAPRPPTPAPTIASRPLSLRPEACRPAAGGAVHTRGLDF

ACDIYIWAPLAGTCGVLLLSLVITLYCRVKFSRSADAPAYQQGQNQLYNELNLG

RREEYDVLDKRRGRDPEMGGKPRRKNPQEGLYNELQKDKMAEAYSEIGMKGE

RRRGKGHDGLYQGLSTATKDTYDALHMQALPPR

P4-z (nucleotide sequence) (SEQ ID NO: 4)
ATGGCCTTAC CAGTGACCGC CTTGCTCCTG CCGCTGGCCT TGCTGCTCCA

CGCCGCCAGG CCGGGATCTC AGGTACAGCT GCAGCAGTCA GGTCCAGGAC

TCGTGACGCC CTCGCAGACC CTCTCACTCA CCTGTGCCAT CTCCGGGGAC

AGTGTCTCTA GCAACAGTGC TACTTGGAAC TGGATCAGGC AGTCCCCATC

GAGAGGCCTT GAGTGGCTGG GAAGGACATA CTACAGGTCC AAGTGGTATA

ACGACTATGC AGTATCTGTG AAAAGTCGAA TGAGCATCAA CCCAGACACA

TCCAAGAACC AGTTCTCCCT GCAGCTGAAC TCTGTGACTC CCGAGGACAC

GGCTGTGTAT TACTGTGCAA GAGGAATGAT GACTTACTAT TACGGTATGG

ACGTCTGGGG CCAAGGGACC ACGGTCACCG TCTCCTCAGG AATTCTAGGA

TCCGGTGGCG GTGGCAGCGG CGGTGGTGGT TCCGGAGGCG GCGGTTCTCA

GCCTGTGCTG ACTCAGTCGT CTTCCCTCTC TGCATCTCCT GGAGCATCAG

CCAGTCTCAC CTGCACCTTG CGCAGTGGCA TCAATGTTGG TCCCTACAGG

ATATACTGGT ACCAGCAGAA GCCAGGGAGT CCTCCCCAGT ATCTCCTGAA

CTACAAATCA GACTCAGATA AGCAGCAGGG CTCTGGAGTC CCCAGCCGCT

TCTCTGGATC CAAAGATGCT TCGGCCAATG CAGGGGTTTT ACTCATCTCT

GGGCTCCGGT CTGAGGATGA GGCTGACTAT TACTGTATGA TTTGGCACAG

CAGCGCTGCT GTGTTCGGAG GAGGCACCCA ACTGACCGTC CTCTCCGCTA

GCACCACGAC GCCAGCGCCG CGACCACCAA CACCGGCGCC CACCATCGCG

TCGCGGCCCC TGTCCCTGCG CCCAGAGGCG TGCCGGCCAG CGGCGGGGGG

CGCAGTGCAC ACGAGGGGGC TGGACTTCGC CTGTGATATC TACATCTGGG

CGCCCTTGGC CGGGACTTGT GGGGTCCTTC TCCTGTCACT GGTTATCACC

CTTTACTGCA GAGTGAAGTT CAGCAGGAGC GCAGACGCCC CCGCGTACCA

GCAGGGCCAG AACCAGCTCT ATAACGAGCT CAATCTAGGA CGAAGAGAGG

AGTACGATGT TTTGGACAAG AGACGTGGCC GGGACCCTGA GATGGGGGGA
```

-continued

```
AAGCCGAGAA GGAAGAACCC TCAGGAAGGC CTGTACAATG AACTGCAGAA

AGATAAGATG GCGGAGGCCT ACAGTGAGAT TGGGATGAAA GGCGAGCGCC

GGAGGGGCAA GGGGCACGAT GGCCTTTACC AGGGTCTCAG TACAGCCACC

AAGGACACCT ACGACGCCCT TCACATGCAG GCCCTGCCCC CTCGCTAA
```

MOV19-28 (F-28) (amino acid sequence) (SEQ ID NO: 5)
```
MALPVTALLLPLALLLHAARPGSSRAAQPAMAQVQLQQSGAELVKPGASVKISC

KASGYSFTGYFMNWVKQSHGKSLEWIGRIHPYDGDTFYNQNFKDKATLTVDKS

SNTAHMELLSLTSEDFAVYYCTRYDGSRAMDYWGQGTTVTVSSGGGGSGGGGS

GGGGSDIELTQSPASLAVSLGQRAIISCKASQSVSFAGTSLMHWYHQKPGQQPKL

LIYRASNLEAGVPTRFSGSGSKTDFTLNIHPVEEEDAATYYCQQSREYPYTFGGG

TKLEIKRAAASTTTPAPRPPTPAPTIASQPLSLRPEACRPAAGGAVHTRGLDFACD

FWVLVVVGGVLACYSLLVTVAFIIFWVRSKRSRLLHSDYMNMTPRRPGPTRKHY

QPYAPPRDFAAYRS
```

MOV19-28 (F-28) (nucleotide sequence) (SEQ ID NO: 6)
```
ATGGCCTTAC CAGTGACCGC CTTGCTCCTG CCGCTGGCCT TGCTGCTCCA

CGCCGCCAGG CCGGGATCCT CTAGAGCGGC CCAGCCGGCC ATGGCCCAGG

TGCAGCTGCA GCAGTCTGGA GCTGAGCTGG TGAAGCCTGG GGCTTCAGTG

AAGATATCCT GCAAGGCTTC TGGTTACTCA TTTACTGGCT ACTTTATGAA

CTGGGTGAAG CAGAGCCATG GAAAGAGCCT TGAGTGGATT GGACGTATTC

ATCCTTACGA TGGTGATACT TTCTACAACC AGAACTTCAA GGACAAGGCC

ACATTGACTG TAGACAAATC CTCTAACACA GCCCACATGG AGCTCCTGAG

CCTGACATCT GAGGACTTTG CAGTCTATTA TTGTACAAGA TACGACGGTA

GTCGGGCTAT GGACTACTGG GGCCAAGGGA CCACGGTCAC CGTCTCCTCA

GGTGGAGGCG GTTCAGGCGG AGGTGGCTCT GGCGGTGGCG GATCGGACAT

CGAGCTCACT CAGTCTCCAG CTTCTTTGGC TGTGTCTCTA GGGCAGAGGG

CCATCATCTC CTGCAAGGCC AGCCAAAGTG TCAGTTTTGC TGGTACTAGT

TTAATGCACT GGTACCACCA GAAACCAGGA CAGCAACCCA AACTCCTCAT

CTATCGTGCA TCCAACCTAG AAGCTGGGGT TCCTACCAGG TTTAGTGGCA

GTGGGTCTAA GACAGACTTC ACCCTCAATA TCCATCCTGT GGAGGAGGAG

GATGCTGCAA CCTATTACTG TCAGCAAAGT AGGGAATATC CGTACACGTT

CGGAGGGGGG ACAAAGTTGG AAATAAAACG GGCGGCCGCT AGCACCACGA

CGCCAGCGCC GCGACCACCA ACACCGGCGC CACCATCGC GTCGCAGCCC

CTGTCCCTGC GCCCAGAGGC GTGCCGGCCA GCGGCGGGGG GCGCAGTGCA

CACGAGGGGG CTGGACTTCG CCTGTGATTT TTGGGTGCTG GTGGTGGTTG

GTGGAGTCCT GGCTTGCTAT AGCTTGCTAG TAACAGTGGC CTTTATTATT

TTCTGGGTGA GGAGTAAGAG GAGCAGGCTC CTGCACAGTG ACTACATGAA

CATGACTCCC CGCCGCCCCG GCCCCACCCG CAAGCATTAC CAGCCCTATG

CCCCACCACG CGACTTCGCA GCCTATCGCT CCTA A
```

MOV19-BB (F-BB) (amino acid sequence) (SEQ ID NO: 7)
```
MALPVTALLLPLALLLHAARPGSSRAAQPAMAQVQLQQSGAELVKPGASVKISC

KASGYSFTGYFMNWVKQSHGKSLEWIGRIHPYDGDTFYNQNFKDKATLTVDKS

SNTAHMELLSLTSEDFAVYYCTRYDGSRAMDYWGQGTTVTVSSGGGGSGGGGS
```

-continued

```
GGGGSDIELTQSPASLAVSLGQRAIISCKASQSVSFAGTSLMHWYHQKPGQQPKL

LIYRASNLEAGVPTRFSGSGSKTDFTLNIHPVEEEDAATYYCQQSREYPYTFGGG

TKLEIKRAAASTTTPAPRPPTPAPTIASQPLSLRPEACRPAAGGAVHTRGLDFACD

IYIWAPLAGTCGVLLLSLVITLYCKRGRKKLLYIFKQPFMRPVQTTQEEDGCSCRF

PEEEEGGCEL

MOV19-BB (F-BB) (nucleotide sequence) (SEQ ID NO: 8)
ATGGCCTTAC CAGTGACCGC CTTGCTCCTG CCGCTGGCCT TGCTGCTCCA

CGCCGCCAGG CCGGGATCCT CTAGAGCGGC CCAGCCGGCC ATGGCCCAGG

TGCAGCTGCA GCAGTCTGGA GCTGAGCTGG TGAAGCCTGG GGCTTCAGTG

AAGATATCCT GCAAGGCTTC TGGTTACTCA TTTACTGGCT ACTTTATGAA

CTGGGTGAAG CAGAGCCATG GAAAGAGCCT TGAGTGGATT GGACGTATTC

ATCCTTACGA TGGTGATACT TTCTACAACC AGAACTTCAA GGACAAGGCC

ACATTGACTG TAGACAAATC CTCTAACACA GCCCACATGG AGCTCCTGAG

CCTGACATCT GAGGACTTTG CAGTCTATTA TTGTACAAGA TACGACGGTA

GTCGGGCTAT GGACTACTGG GGCCAAGGGA CCACGGTCAC CGTCTCCTCA

GGTGGAGGCG GTTCAGGCGG AGGTGGCTCT GGCGGTGGCG GATCGGACAT

CGAGCTCACT CAGTCTCCAG CTTCTTTGGC TGTGTCTCTA GGGCAGAGGG

CCATCATCTC CTGCAAGGCC AGCCAAAGTG TCAGTTTTGC TGGTACTAGT

TTAATGCACT GGTACCACCA GAAACCAGGA CAGCAACCCA AACTCCTCAT

CTATCGTGCA TCCAACCTAG AAGCTGGGGT TCCTACCAGG TTTAGTGGCA

GTGGGTCTAA GACAGACTTC ACCCTCAATA TCCATCCTGT GGAGGAGGAG

GATGCTGCAA CCTATTACTG TCAGCAAAGT AGGGAATATC CGTACACGTT

CGGAGGGGGG ACAAAGTTGG AAATAAAACG GGCGGCCGCT AGCACCACGA

CGCCAGCGCC GCGACCACCA ACACCGGCGC CCACCATCGC GTCGCAGCCC

CTGTCCCTGC GCCCAGAGGC GTGCCGGCCA GCGGCGGGGG GCGCAGTGCA

CACGAGGGGG CTGGACTTCG CCTGTGATAT CTACATCTGG GCGCCCTTGG

CCGGGACTTG TGGGGTCCTT CTCCTGTCAC TGGTTATCAC CCTTTACTGC

AAACGGGGCA GAAAGAAACT CCTGTATATA TTCAAACAAC CATTTATGAG

ACCAGTACAA ACTACTCAAG AGGAAGATGG CTGTAGCTGC CGATTTCCAG

AAGAAGAAGA AGGAGGATGT GAACTGTAA

C6.5-BB (HER2-BB) (amino acid sequence) (SEQ ID NO: 9)
MALPVTALLLPLALLLHAARPGSQVQLLQSGAELKKPGESLKISCKGSGYSFTSY

WIAWVRQMPGKGLEYMGLIYPGDSDTKYSPSFQGQVTISVDKSVSTAYLQWSSL

KPSDSAVYFCARHDVGYCSSSNCAKWPEYFQHWGQGTLVTVSSGGGGSGGGGS

GGGGSQSVLTQPPSVSAAPGQKVTISCSGSSSNIGNNYVSWYQQLPGTAPKLLIY

GHTNRPAGVPDRFSGSKSGTSASLAISGFRSEDEADYYCAAWDDSLSGWVFGGG

TKLTVLGASTTTPAPRPPTPAPTIASQPLSLRPEACRPAAGGAVHTRGLDFACDIYI

WAPLAGTCGVLLLSLVITLYCKRGRKKLLYIFKQPFMRPVQTTQEEDGCSCRFPE

EEEGGCEL

C6.5-BB (HER2-BB) (nucleotide sequence) (SEQ ID NO: 10)
ATGGCCTTAC CAGTGACCGC CTTGCTCCTG CCGCTGGCCT TGCTGCTCCA

CGCCGCCAGG CCGGGATCCC AGGTGCAGCT GTTGCAGTCT GGGGCAGAGT
```

-continued

```
TGAAAAAACC CGGGGAGTCT CTGAAGATCT CCTGTAAGGG TTCTGGATAC

AGCTTTACCA GCTACTGGAT CGCCTGGGTG CGCCAGATGC CCGGGAAAGG

CCTGGAGTAC ATGGGGCTCA TCTATCCTGG TGACTCTGAC ACCAAATACA

GCCCGTCCTT CCAAGGCCAG GTCACCATCT CAGTCGACAA GTCCGTCAGC

ACTGCCTACT TGCAATGGAG CAGTCTGAAG CCCTCGGACA GCGCCGTGTA

TTTTTGTGCG AGACATGACG TGGGATATTG CAGTAGTTCC AACTGCGCAA

AGTGGCCTGA ATACTTCCAG CATTGGGGCC AGGGCACCCT GGTCACCGTC

TCCTCAGGTG GAGGCGGTTC AGGCGGAGGT GGCTCTGGCG GTGGCGGATC

GCAGTCTGTG TTGACGCAGC CGCCCTCAGT GTCTGCGGCC CCAGGACAGA

AGGTCACCAT CTCCTGCTCT GGAAGCAGCT CCAACATTGG GAATAATTAT

GTATCCTGGT ACCAGCAGCT CCCAGGAACA GCCCCCAAAC TCCTCATCTA

TGGTCACACC AATCGGCCCG CAGGGGTCCC TGACCGATTC TCTGGCTCCA

AGTCTGGCAC CTCAGCCTCC CTGGCCATCA GTGGGTTCCG GTCCGAGGAT

GAGGCTGATT ATTACTGTGC AGCATGGGAT GACAGCCTGA GTGGTTGGGT

GTTCGGCGGA GGGACCAAGC TGACCGTCCT AGGTGCTAGC ACCACGACGC

CAGCGCCGCG ACCACCAACA CCGGCGCCCA CCATCGCGTC GCAGCCCCTG

TCCCTGCGCC CAGAGGCGTG CCGGCCAGCG GCGGGGGGCG CAGTGCACAC

GAGGGGGCTG GACTTCGCCT GTGATATCTA CATCTGGGCG CCCTTGGCCG

GGACTTGTGG GGTCCTTCTC CTGTCACTGG TTATCACCCT TTACTGCAAA

CGGGGCAGAA AGAAACTCCT GTATATATTC AAACAACCAT TTATGAGACC

AGTACAAACT ACTCAAGAGG AAGATGGCTG TAGCTGCCGA TTTCCAGAAG

AAGAAGAAGG AGGATGTGAA CTGTAA
```

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A T cell comprising a first chimeric antigen receptor (CAR) and a second CAR, wherein:
   (a) the first CAR comprises a first antigen binding domain that targets a first antigen and the first CAR comprises SEQ ID NO: 5, SEQ ID NO: 7, or SEQ ID NO: 9;
   (b) the second CAR comprises a second antigen binding domain that targets a second antigen and the second CAR comprises SEQ ID NO: 3;
   (c) the first CAR is not capable of inducing cell activation upon binding to the first antigen and the first CAR increases resistance to antigen-induced cell death (AICD); and
   (d) the T cell is selective for a cancer tissue over a normal tissue thereby reducing "on-target" toxicity, while maintaining potent anti-cancer activity, tumor localization and in vivo persistence when compared to a cell comprising only the first CAR, the second CAR, or a conventional first or second generation CAR comprising the first or the second antigen-binding domain.

2. The T cell of claim 1, wherein activation of the T cell is dependent on the binding of the first antigen binding domain to the first antigen and the binding of the second antigen binding domain to the second antigen.

3. The T cell of claim 1, wherein the T cell exhibits anti-tumor immunity when the first antigen binding domain binds to the first antigen and the second antigen binding domain binds to the second antigen.

4. The T cell of claim 1, wherein the T cell exhibits heightened tumor specificity.

5. The T cell of claim 1, wherein the T cell targets:
   (a) mesothelin and folate receptor alpha on ovarian cancer cells; or
   (b) mesothelin and HER2 on breast cancer cells.

* * * * *

SEQUENCE LISTING

<160> NUMBER OF SEQ ID NOS: 10

<210> SEQ ID NO 1
<211> LENGTH: 26
<212> TYPE: DNA
<213> ORGANISM: Homo sapiens

<400> SEQUENCE: 1
acgcgctagc accacgacgc cagcgc                                          26

<210> SEQ ID NO 2
<211> LENGTH: 36
<212> TYPE: DNA
<213> ORGANISM: Homo sapiens

<400> SEQUENCE: 2
acgcgtcgac ttaggagcga taggctgcga agtcgc                              36

<210> SEQ ID NO 3
<211> LENGTH: 465

```
<212> TYPE: PRT
<213> ORGANISM: Homo sapiens
<220> FEATURE:
<221> NAME/KEY: misc_feature
<223> OTHER INFORMATION: P4-z

<400> SEQUENCE: 3

Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Gln Ser Gly Pro
            20                  25                  30

Gly Leu Val Thr Pro Ser Gln Thr Leu Ser Leu Thr Cys Ala Ile Ser
        35                  40                  45

Gly Asp Ser Val Ser Ser Asn Ser Ala Thr Trp Asn Trp Ile Arg Gln
    50                  55                  60

Ser Pro Ser Arg Gly Leu Glu Trp Leu Gly Arg Thr Tyr Tyr Arg Ser
65                  70                  75                  80

Lys Trp Tyr Asn Asp Tyr Ala Val Ser Val Lys Ser Arg Met Ser Ile
                85                  90                  95

Asn Pro Asp Thr Ser Lys Asn Gln Phe Ser Leu Gln Leu Asn Ser Val
            100                 105                 110

Thr Pro Glu Asp Thr Ala Val Tyr Tyr Cys Ala Arg Gly Met Met Thr
        115                 120                 125

Tyr Tyr Tyr Gly Met Asp Val Trp Gly Gln Gly Thr Thr Val Thr Val
    130                 135                 140

Ser Ser Gly Ile Leu Gly Ser Gly Gly Gly Ser Gly Gly Gly Gly
145                 150                 155                 160

Ser Gly Gly Gly Gly Ser Gln Pro Val Leu Thr Gln Ser Ser Ser Leu
                165                 170                 175

Ser Ala Ser Pro Gly Ala Ser Ala Ser Leu Thr Cys Thr Leu Arg Ser
            180                 185                 190

Gly Ile Asn Val Gly Pro Tyr Arg Ile Tyr Trp Tyr Gln Gln Lys Pro
        195                 200                 205

Gly Ser Pro Pro Gln Tyr Leu Leu Asn Tyr Lys Ser Asp Ser Asp Lys
    210                 215                 220

Gln Gln Gly Ser Gly Val Pro Ser Arg Phe Ser Gly Ser Lys Asp Ala
225                 230                 235                 240

Ser Ala Asn Ala Gly Val Leu Leu Ile Ser Gly Leu Arg Ser Glu Asp
                245                 250                 255

Glu Ala Asp Tyr Tyr Cys Met Ile Trp His Ser Ser Ala Ala Val Phe
            260                 265                 270

Gly Gly Gly Thr Gln Leu Thr Val Leu Ser Ala Ser Thr Thr Thr Pro
        275                 280                 285

Ala Pro Arg Pro Pro Thr Pro Ala Pro Thr Ile Ala Ser Arg Pro Leu
    290                 295                 300

Ser Leu Arg Pro Glu Ala Cys Arg Pro Ala Ala Gly Gly Ala Val His
305                 310                 315                 320

Thr Arg Gly Leu Asp Phe Ala Cys Asp Ile Tyr Ile Trp Ala Pro Leu
                325                 330                 335

Ala Gly Thr Cys Gly Val Leu Leu Leu Ser Leu Val Ile Thr Leu Tyr
            340                 345                 350

Cys Arg Val Lys Phe Ser Arg Ser Ala Asp Ala Pro Ala Tyr Gln Gln
        355                 360                 365

Gly Gln Asn Gln Leu Tyr Asn Glu Leu Asn Leu Gly Arg Arg Glu Glu
    370                 375                 380
```

Tyr Asp Val Leu Asp Lys Arg Arg Gly Arg Asp Pro Glu Met Gly Gly
385                 390                 395                 400

Lys Pro Arg Arg Lys Asn Pro Gln Glu Gly Leu Tyr Asn Glu Leu Gln
            405                 410                 415

Lys Asp Lys Met Ala Glu Ala Tyr Ser Glu Ile Gly Met Lys Gly Glu
        420                 425                 430

Arg Arg Arg Gly Lys Gly His Asp Gly Leu Tyr Gln Gly Leu Ser Thr
    435                 440                 445

Ala Thr Lys Asp Thr Tyr Asp Ala Leu His Met Gln Ala Leu Pro Pro
        450                 455                 460

Arg
465

<210> SEQ ID NO 4
<211> LENGTH: 1398
<212> TYPE: DNA
<213> ORGANISM: Homo sapiens
<220> FEATURE:
<221> NAME/KEY: misc_feature
<223> OTHER INFORMATION: P4-z

<400> SEQUENCE: 4
atggccttac cagtgaccgc cttgctcctg ccgctggcct tgctgctcca cgccgccagg      60
ccgggatctc aggtacagct gcagcagtca ggtccaggac tcgtgacgcc ctcgcagacc     120
ctctcactca cctgtgccat ctccgggggac agtgtctcta gcaacagtgc tacttggaac     180
tggatcaggc agtccccatc gagaggcctt gagtggctgg aaggacata ctacaggtcc      240 aagtggtata cgactatgc agtatctgtg aaaagtcgaa tgagcatcaa cccagacaca      300
tccaagaacc agttctccct gcagctgaac tctgtgactc ccgaggacac ggctgtgtat     360
tactgtgcaa gaggaatgat gacttactat acggtatgg acgtctgggg ccaagggacc      420
acggtcaccg tctcctcagg aattctagga tccgtggcg gtggcagcgg cggtggtggt      480
tccggaggcg gcggttctca gctgtgctg actcagtcgt cttccctctc tgcatctcct      540
ggagcatcag ccagtctcac ctgcaccttg cgcagtggca tcaatgttgg tcctacagg      600 atatactggt accagcagaa gccagggagt cctccccagt atctcctgaa ctacaaatca      660
gactcagata gcagcaggg ctctggagtc cccagccgct tctctggatc caaagatgct      720
tcggccaatg cagggtttt actcatctct gggctccggt ctgaggatga ggctgactat      780
tactgtatga tttggcacag cagcgctgct gtgttcggag gaggcaccca actgaccgtc      840
ctctccgcta gcaccacgac gccagcgccg cgaccaccaa caccggcgcc caccatcgcg     900
tcgcggcccc tgtccctgcg cccagaggcg tgccggccag cggcggggg cgcagtgcac      960 acgagggggc tggacttcgc ctgtgatatc tacatctggg cgcccttggc cgggacttgt    1020 gggtccttc cctgtcact ggttatcacc ctttactgca gagtgaagtt cagcaggagc     1080
gcagacgccc ccgcgtacca gcagggccag aaccagctct ataacgagct caatctagga    1140
cgaagagagg agtacgatgt tttggacaag agacgtggcc gggaccctga gatggggga     1200 aagccgagaa ggaagaaccc tcaggaaggc ctgtacaatg aactgcagaa agataagatg    1260
gcggaggcct acagtgagat tgggatgaaa ggcgagcgcc ggaggggcaa ggggcacgat    1320
ggcctttacc agggtctcag tacagccacc aaggacacct acgacgccct tcacatgcag    1380
gccctgcccc ctcgctaa                                                  1398

```
<210> SEQ ID NO 5
<211> LENGTH: 394
<212> TYPE: PRT
<213> ORGANISM: Homo sapiens
<220> FEATURE:
<221> NAME/KEY: misc_feature
<223> OTHER INFORMATION: MOV19-28 (F-28)

<400> SEQUENCE: 5

Met Ala Leu Pro Val Thr Ala Leu Leu Leu Pro Leu Ala Leu Leu Leu
1               5                   10                  15

His Ala Ala Arg Pro Gly Ser Ser Arg Ala Ala Gln Pro Ala Met Ala
            20                  25                  30

Gln Val Gln Leu Gln Gln Ser Gly Ala Glu Leu Val Lys Pro Gly Ala
        35                  40                  45

Ser Val Lys Ile Ser Cys Lys Ala Ser Gly Tyr Ser Phe Thr Gly Tyr
    50                  55                  60

Phe Met Asn Trp Val Lys Gln Ser His Gly Lys Ser Leu Glu Trp Ile
65                  70                  75                  80

Gly Arg Ile His Pro Tyr Asp Gly Asp Thr Phe Tyr Asn Gln Asn Phe
                85                  90                  95

Lys Asp Lys Ala Thr Leu Thr Val Asp Lys Ser Ser Asn Thr Ala His
            100                 105                 110

Met Glu Leu Leu Ser Leu Thr Ser Glu Asp Phe Ala Val Tyr Tyr Cys
        115                 120                 125

Thr Arg Tyr Asp Gly Ser Arg Ala Met Asp Tyr Trp Gly Gln Gly Thr
    130                 135                 140

Thr Val Thr Val Ser Ser Gly Gly Gly Gly Ser Gly Gly Gly Gly Ser
145                 150                 155                 160

Gly Gly Gly Gly Ser Asp Ile Glu Leu Thr Gln Ser Pro Ala Ser Leu
                165                 170                 175

Ala Val Ser Leu Gly Gln Arg Ala Ile Ile Ser Cys Lys Ala Ser Gln
            180                 185                 190

Ser Val Ser Phe Ala Gly Thr Ser Leu Met His Trp Tyr His Gln Lys
        195                 200                 205

Pro Gly Gln Gln Pro Lys Leu Leu Ile Tyr Arg Ala Ser Asn Leu Glu
    210                 215                 220

Ala Gly Val Pro Thr Arg Phe Ser Gly Ser Gly Ser Lys Thr Asp Phe
225                 230                 235                 240

Thr Leu Asn Ile His Pro Val Glu Glu Asp Ala Ala Thr Tyr Tyr
                245                 250                 255

Cys Gln Gln Ser Arg Glu Tyr Pro Tyr Thr Phe Gly Gly Gly Thr Lys
            260                 265                 270

Leu Glu Ile Lys Arg Ala Ala Ala Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Phe Trp Val Leu Val Val Gly Gly Val
                325                 330                 335

Leu Ala Cys Tyr Ser Leu Leu Val Thr Val Ala Phe Ile Ile Phe Trp
            340                 345                 350

Val Arg Ser Lys Arg Ser Arg Leu Leu His Ser Asp Tyr Met Asn Met
        355                 360                 365
```

```
Thr Pro Arg Arg Pro Gly Pro Thr Arg Lys His Tyr Gln Pro Tyr Ala
    370                 375                 380

Pro Pro Arg Asp Phe Ala Ala Tyr Arg Ser
385                 390
```

<210> SEQ ID NO 6
<211> LENGTH: 1185
<212> TYPE: DNA
<213> ORGANISM: Homo sapiens
<220> FEATURE:
<221> NAME/KEY: misc_feature
<223> OTHER INFORMATION: MOV19-28 (F-28)

<400> SEQUENCE: 6

```
atggccttac cagtgaccgc cttgctcctg ccgctggcct tgctgctcca cgccgccagg     60
ccgggatcct ctagagcggc ccagccggcc atggcccagg tgcagctgca gcagtctgga    120
gctgagctgg tgaagcctgg ggcttcagtg aagatatcct gcaaggcttc tggttactca    180
tttactggct actttatgaa ctgggtgaag cagagccatg aaagagcct tgagtggatt     240 ggacgtattc atccttacga tggtgatact ttctacaacc agaacttcaa ggacaaggcc    300
acattgactg tagacaaatc ctctaacaca gcccacatgg agctcctgag cctgacatct    360
gaggactttg cagtctatta ttgtacaaga tacgacggta gtcgggctat ggactactgg    420
ggccaaggga ccacggtcac cgtctcctca ggtggaggcg gttcaggcgg aggtggctct    480
ggcggtggcg gatcggacat cgagctcact cagtctccag cttctttggc tgtgtctcta    540
gggcagaggg ccatcatctc ctgcaaggcc agccaaagtg tcagttttgc tggtactagt    600
ttaatgcact ggtaccacca gaaaccagga cagcaaccca actcctcat ctatcgtgca     660 tccaacctag aagctggggt tcctaccagg tttagtggca gtgggtctaa gacagacttc    720
accctcaata tccatcctgt ggaggaggag gatgctgcaa cctattactg tcagcaaagt    780
agggaatatc cgtacacgtt cggagggggg acaaagttgg aaataaaacg ggcggccgct    840
agcaccacga cgccagcgcc gcgaccacca acaccggcgc ccaccatcgc gtcgcagccc    900
ctgtccctgc gcccagaggc gtgccggcca cggcggggg gcgcagtgca cacgaggggg    960
ctggacttcg cctgtgattt ttgggtgctg gtggtggttg gtggagtcct ggcttgctat   1020
agcttgctag taacagtggc ctttattatt ttctgggtga ggagtaagag gagcaggctc   1080
ctgcacagtg actacatgaa catgactccc cgccgcccg ggcccacccg caagcattac    1140
cagccctatg ccccaccacg cgacttcgca gcctatcgct cctaa                   1185
```

<210> SEQ ID NO 7
<211> LENGTH: 392
<212> TYPE: PRT
<213> ORGANISM: Homo sapiens
<220> FEATURE:
<221> NAME/KEY: misc_feature
<223> OTHER INFORMATION: MOV19-BB (F-BB)

<400> SEQUENCE: 7

```
Met Ala Leu Pro Val Thr Ala Leu Leu Leu Pro Leu Ala Leu Leu Leu
1               5                   10                  15

His Ala Ala Arg Pro Gly Ser Ser Arg Ala Ala Gln Pro Ala Met Ala
            20                  25                  30

Gln Val Gln Leu Gln Gln Ser Gly Ala Glu Leu Val Lys Pro Gly Ala
        35                  40                  45

Ser Val Lys Ile Ser Cys Lys Ala Ser Gly Tyr Ser Phe Thr Gly Tyr
    50                  55                  60
```

Phe Met Asn Trp Val Lys Gln Ser His Gly Lys Ser Leu Glu Trp Ile
65                  70                  75                  80

Gly Arg Ile His Pro Tyr Asp Gly Asp Thr Phe Tyr Asn Gln Asn Phe
                85                  90                  95

Lys Asp Lys Ala Thr Leu Thr Val Asp Lys Ser Ser Asn Thr Ala His
            100                 105                 110

Met Glu Leu Leu Ser Leu Thr Ser Glu Asp Phe Ala Val Tyr Tyr Cys
        115                 120                 125

Thr Arg Tyr Asp Gly Ser Arg Ala Met Asp Tyr Trp Gly Gln Gly Thr
    130                 135                 140

Thr Val Thr Val Ser Ser Gly Gly Gly Ser Gly Gly Gly Gly Ser
145                 150                 155                 160

Gly Gly Gly Gly Ser Asp Ile Glu Leu Thr Gln Ser Pro Ala Ser Leu
                165                 170                 175

Ala Val Ser Leu Gly Gln Arg Ala Ile Ile Ser Cys Lys Ala Ser Gln
            180                 185                 190

Ser Val Ser Phe Ala Gly Thr Ser Leu Met His Trp Tyr His Gln Lys
        195                 200                 205

Pro Gly Gln Gln Pro Lys Leu Leu Ile Tyr Arg Ala Ser Asn Leu Glu
    210                 215                 220

Ala Gly Val Pro Thr Arg Phe Ser Gly Ser Gly Ser Lys Thr Asp Phe
225                 230                 235                 240

Thr Leu Asn Ile His Pro Val Glu Glu Glu Asp Ala Ala Thr Tyr Tyr
                245                 250                 255

Cys Gln Gln Ser Arg Glu Tyr Pro Tyr Thr Phe Gly Gly Gly Thr Lys
            260                 265                 270

Leu Glu Ile Lys Arg Ala Ala Ala Ser Thr Thr Thr Pro Ala Pro Arg
        275                 280                 285

Pro Pro Thr Pro Ala Pro Thr Ile Ala Ser Gln Pro Leu Ser Leu Arg
    290                 295                 300

Pro Glu Ala Cys Arg Pro Ala Ala Gly Gly Ala Val His Thr Arg Gly
305                 310                 315                 320

Leu Asp Phe Ala Cys Asp Ile Tyr Ile Trp Ala Pro Leu Ala Gly Thr
                325                 330                 335

Cys Gly Val Leu Leu Leu Ser Leu Val Ile Thr Leu Tyr Cys Lys Arg
            340                 345                 350

Gly Arg Lys Lys Leu Leu Tyr Ile Phe Lys Gln Pro Phe Met Arg Pro
        355                 360                 365

Val Gln Thr Thr Gln Glu Glu Asp Gly Cys Ser Cys Arg Phe Pro Glu
    370                 375                 380

Glu Glu Glu Gly Gly Cys Glu Leu
385                 390

<210> SEQ ID NO 8
<211> LENGTH: 1179
<212> TYPE: DNA
<213> ORGANISM: Homo sapiens
<220> FEATURE:
<221> NAME/KEY: misc_feature
<223> OTHER INFORMATION: MOV19-BB (F-BB)

<400> SEQUENCE: 8
atggccttac cagtgaccgc cttgctcctg ccgctggcct tgctgctcca cgccgccagg    60
ccgggatcct ctagagcggc ccagccggcc atggcccagg tgcagctgca gcagtctgga   120

```
gctgagctgg tgaagcctgg ggcttcagtg aagatatcct gcaaggcttc tggttactca    180
tttactggct actttatgaa ctgggtgaag cagagccatg gaaagagcct tgagtggatt    240
ggacgtattc atccttacga tggtgatact ttctacaacc agaacttcaa ggacaaggcc    300
acattgactg tagacaaatc ctctaacaca gcccacatgg agctcctgag cctgacatct    360
gaggactttg cagtctatta ttgtacaaga tacgacggta gtcgggctat ggactactgg    420
ggccaaggga ccacggtcac cgtctcctca ggtggaggcg gttcaggcgg aggtggctct    480
ggcggtggcg gatcggacat cgagctcact cagtctccag cttctttggc tgtgtctcta    540
gggcagaggg ccatcatctc ctgcaaggcc agccaaagtg tcagttttgc tggtactagt    600
ttaatgcact ggtaccacca gaaaccagga cagcaaccca aactcctcat ctatcgtgca    660
tccaacctag aagctggggt tcctaccagg tttagtggca gtgggtctaa gacagacttc    720
accctcaata tccatcctgt ggaggaggag gatgctgcaa cctattactg tcagcaaagt    780
agggaatatc cgtacacgtt cggagggggg acaaagttgg aaataaaacg gcggccgct    840 agcaccacga cgccagcgcc gcgaccacca caccggcgc ccaccatcgc gtcgcagccc    900
ctgtccctgc gcccagaggc gtgccggcca gcggcggggg cgcagtgca cacgagggggg    960 ctggacttcg cctgtgatat ctacatctgg gcgcccttgg ccgggacttg tggggtcctt   1020
ctcctgtcac tggttatcac cctttactgc aaacgggca gaaagaaact cctgtatata   1080
ttcaaacaac catttatgag accagtacaa actactcaag aggaagatgg ctgtagctgc   1140
cgatttccag aagaagaaga aggaggatgt gaactgtaa                          1179
```

<210> SEQ ID NO 9
<211> LENGTH: 391
<212> TYPE: PRT
<213> ORGANISM: Homo sapiens
<220> FEATURE:
<221> NAME/KEY: misc_feature
<223> OTHER INFORMATION: C6.5-BB (HER2-BB)

<400> SEQUENCE: 9

```
Met Ala Leu Pro Val Thr Ala Leu Leu Leu Pro Leu Ala Leu Leu Leu
1               5                   10                  15

His Ala Ala Arg Pro Gly Ser Gln Val Gln Leu Gln Ser Gly Ala
            20                  25                  30

Glu Leu Lys Lys Pro Gly Glu Ser Leu Lys Ile Ser Cys Lys Gly Ser
        35                  40                  45

Gly Tyr Ser Phe Thr Ser Tyr Trp Ile Ala Trp Val Arg Gln Met Pro
    50                  55                  60

Gly Lys Gly Leu Glu Tyr Met Gly Leu Ile Tyr Pro Gly Asp Ser Asp
65                  70                  75                  80

Thr Lys Tyr Ser Pro Ser Phe Gln Gly Gln Val Thr Ile Ser Val Asp
                85                  90                  95

Lys Ser Val Ser Thr Ala Tyr Leu Gln Trp Ser Ser Leu Lys Pro Ser
            100                 105                 110

Asp Ser Ala Val Tyr Phe Cys Ala Arg His Asp Val Gly Tyr Cys Ser
        115                 120                 125

Ser Ser Asn Cys Ala Lys Trp Pro Glu Tyr Phe Gln His Trp Gly Gln
    130                 135                 140

Gly Thr Leu Val Thr Val Ser Ser Gly Gly Gly Gly Ser Gly Gly Gly
145                 150                 155                 160

Gly Ser Gly Gly Gly Gly Ser Gln Ser Val Leu Thr Gln Pro Pro Ser
                165                 170                 175
```

Val Ser Ala Ala Pro Gly Gln Lys Val Thr Ile Ser Cys Ser Gly Ser
            180                 185                 190

Ser Ser Asn Ile Gly Asn Asn Tyr Val Ser Trp Tyr Gln Gln Leu Pro
        195                 200                 205

Gly Thr Ala Pro Lys Leu Leu Ile Tyr Gly His Thr Asn Arg Pro Ala
    210                 215                 220

Gly Val Pro Asp Arg Phe Ser Gly Ser Lys Ser Gly Thr Ser Ala Ser
225                 230                 235                 240

Leu Ala Ile Ser Gly Phe Arg Ser Glu Asp Glu Ala Asp Tyr Tyr Cys
                245                 250                 255

Ala Ala Trp Asp Asp Ser Leu Ser Gly Trp Val Phe Gly Gly Gly Thr
            260                 265                 270

Lys Leu Thr Val Leu Gly Ala Ser Thr Thr Thr Pro Ala Pro Arg Pro
        275                 280                 285

Pro Thr Pro Ala Pro Thr Ile Ala Ser Gln Pro Leu Ser Leu Arg Pro
    290                 295                 300

Glu Ala Cys Arg Pro Ala Ala Gly Gly Ala Val His Thr Arg Gly Leu
305                 310                 315                 320

Asp Phe Ala Cys Asp Ile Tyr Ile Trp Ala Pro Leu Ala Gly Thr Cys
                325                 330                 335

Gly Val Leu Leu Leu Ser Leu Val Ile Thr Leu Tyr Cys Lys Arg Gly
            340                 345                 350

Arg Lys Lys Leu Leu Tyr Ile Phe Lys Gln Pro Phe Met Arg Pro Val
        355                 360                 365

Gln Thr Thr Gln Glu Glu Asp Gly Cys Ser Cys Arg Phe Pro Glu Glu
    370                 375                 380

Glu Glu Gly Gly Cys Glu Leu
385                 390

<210> SEQ ID NO 10
<211> LENGTH: 1176
<212> TYPE: DNA
<213> ORGANISM: Homo sapiens
<220> FEATURE:
<221> NAME/KEY: misc_feature
<223> OTHER INFORMATION: C6.5-BB (HER2-BB)

<400> SEQUENCE: 10

| | | |
|---|---|---|
| atggcttac cagtgaccgc cttgctcctg ccgctggcct tgctgctcca cgccgccagg | 60 |
| ccgggatccc aggtgcagct gttgcagtct ggggcagagt tgaaaaaacc cggggagtct | 120 |
| ctgaagatct cctgtaaggg ttctggatac agctttacca gctactggat cgcctgggtg | 180 |
| cgccagatgc ccgggaaagg cctggagtac atggggctca tctatcctgg tgactctgac | 240 |
| accaaataca gcccgtcctt ccaaggccag gtcaccatct cagtcgacaa gtccgtcagc | 300 |
| actgcctact gcaatggag cagtctgaag ccctcggaca cgccgtgta ttttgtgcg | 360 |
| agacatgacg tgggatattg cagtagttcc aactgcgcaa agtggcctga atacttccag | 420 |
| cattggggcc agggcaccct ggtcaccgtc tcctcaggtg gaggcggttc aggcggaggt | 480 |
| ggctctggcg gtggcggatc gcagtctgtg ttgacgcagc cgccctcagt gtctgcggcc | 540 |
| ccaggacaga aggtcaccat ctcctgctct ggaagcagct ccaacattgg gaataattat | 600 |
| gtatcctggt accagcagct cccaggaaca gcccccaaac tcctcatcta tggtcacacc | 660 |
| aatcggcccg caggggtccc tgaccgattc tctggctcca agtctggcac ctcagcctcc | 720 |
| ctggccatca gtgggttccg gtccgaggat gaggctgatt attactgtgc agcatgggat | 780 |

```
gacagcctga gtggttgggt gttcggcgga gggaccaagc tgaccgtcct aggtgctagc    840
accacgacgc cagcgccgcg accaccaaca ccggcgccca ccatcgcgtc gcagccctg     900 tccctgcgcc cagaggcgtg ccggccagcg gcggggggcg cagtgcacac gaggggctg     960 gacttcgcct gtgatatcta catctgggcg cccttggccg ggacttgtgg ggtccttctc    1020
ctgtcactgg ttatcaccct ttactgcaaa cggggcagaa agaaactcct gtatatattc    1080
aaacaaccat ttatgagacc agtacaaact actcaagagg aagatggctg tagctgccga    1140
tttccagaag aagaagaagg aggatgtgaa ctgtaa                              1176
```